(12) United States Patent
Hohlfeld et al.

(10) Patent No.: US 12,365,698 B2
(45) Date of Patent: Jul. 22, 2025

(54) APPLICATION OF BORON DIPYRROMETHENE DERIVATIVES IN ANTI-TUMOR AND ANTI-BACTERIAL THERAPY

(71) Applicant: biolitec Unternehmensbeteiligungs III AG, Vienna (AT)

(72) Inventors: Benjamin Florian Hohlfeld, Berlin (DE); Arno Wiehe, Berlin (DE); Burkhard Gitter, Jena (DE); Dorika Steen, Jena (DE); Gerhard Wieland, Jena (DE); Volker Albrecht, Nuthetal (DE)

(73) Assignee: BIOLITEC UNTERNEHMENSBETEILIGUNGS III AG, Vienna (AT)

( * ) Notice: Subject to any disclaimer, the term of this patent is extended or adjusted under 35 U.S.C. 154(b) by 405 days.

(21) Appl. No.: 17/774,662

(22) PCT Filed: Nov. 5, 2020

(86) PCT No.: PCT/EP2020/081184
§ 371 (c)(1),
(2) Date: May 5, 2022

(87) PCT Pub. No.: WO2021/089730
PCT Pub. Date: May 14, 2021

(65) Prior Publication Data
US 2022/0380388 A1    Dec. 1, 2022

Related U.S. Application Data

(60) Provisional application No. 62/930,933, filed on Nov. 5, 2019.

(51) Int. Cl.
| | |
|---|---|
| *C07F 5/02* | (2006.01) |
| *A61K 31/69* | (2006.01) |
| *A61K 41/00* | (2020.01) |
| *A61K 47/64* | (2017.01) |
| *A61P 35/00* | (2006.01) |

(52) U.S. Cl.
CPC ............. *C07F 5/022* (2013.01); *A61K 31/69* (2013.01); *A61K 41/0057* (2013.01); *A61K 47/64* (2017.08); *A61P 35/00* (2018.01)

(58) Field of Classification Search
CPC ......... C07F 5/022; A61K 47/64; A61K 31/69; A61K 41/0057; A61P 35/00
See application file for complete search history.

(56) References Cited

PUBLICATIONS

Martinez et al. (ACS Infect. Dis. 2019, 5, 9, 1624-1633) (Year: 2019).*
Correia Pharmaceutics. Sep. 2021; 13(9): 1332. (Year: 2021).*
Hu. Journal of Nanobiotechnology. 2022; 20 (437) (Year: 2022).*
Banfi Stefano et al: "Synthesis and photo-physical properties of a series of BODIPY dyes", Tetrahedron, Elsevier Science Publishers, Amsterdam, NL, vol. 69, No. 24, Apr. 18, 2013 (Apr. 18, 2013) pp. 4845-4856.
PCT Search Report and Written Opinion mailed on May 14, 2021 for PCT Application PCT/EP2020/081184, 5 pages.

* cited by examiner

*Primary Examiner* — Daniel R Carcanague
*Assistant Examiner* — Jerica Katlynn Wilson
(74) *Attorney, Agent, or Firm* — McCormick, Paulding & Huber PLLC

(57) ABSTRACT

Biologically active compounds and their methods of preparation are provided that may be used as photosensitizers for diagnostic and therapeutic applications, particularly for PDT of cancer, infections and other hyperproliferative diseases, fluorescence diagnosis and PDT treatment of non-tumorous indications such as arthritis, inflammatory diseases, viral or bacterial infections, dermatological, otorhinolaryngology disorders, ophthalmological or urological disorders. As the compounds exhibit also toxicity against targets (tumor cells, bacteria, inflammation-related cells) without light these biologically active compounds may also be used for the light-independent treatment of such indications. Embodiments also include methods to synthesize boron dipyrromethene complex structures incorporating a substituted 2,3,5,6-tetrafluorophenyl-dipyrromethene (2,3,5,6-tetrafluorophenyl-dipyrrin) unit or a substituted 3-nitrophenyl-dipyrromethene (3-nitrophenyl-dipyrrin) unit. Amphiphilic compounds with increased anti-tumour and anti-bacterial efficacy are also provided. Specifically, this is achieved by substitution with bromine atoms and sugar moieties.

11 Claims, 14 Drawing Sheets

APPLICATION OF BORON DIPYRROMETHENE DERIVATIVES IN ANTI-TUMOR AND ANTI-BACTERIAL THERAPY

CROSS REFERENCE TO PRIORITY APPLICATION

This patent application claims priority to U.S. patent application No. 62/930,933, filed on Nov. 5, 2019, and International application PCT/EP2020/081184, filed on Nov. 5, 2020, entitled, "Application of boron dipyrromethene derivatives in anti-tumor and anti-bacterial therapy", hereby expressly incorporated by reference in its entirety as part of the present disclosure.

TECHNICAL FIELD

Present disclosure relates to the chemistry of biologically active compounds. More particularly it relates to certain boron dipyrromethene complexes that can be used to treat tumorous diseases as well as bacterial infections and other diseases. The action of these boron dipyrromethene complexes against tumor cells and bacteria may be intensified by light, thus they can also be used as photosensitizers for a wide range of light irradiation treatments such as photodynamic therapy of cancer, infections and other diseases.

BACKGROUND

Cancer is one of the main causes of death worldwide. Though many therapeutic approaches are known there is still need for new active substances and therapies that can be applied to tumors which cannot successfully be treated by conventional chemotherapeutics. One of those newer therapeutic approaches is photodynamic therapy (PDT).

PDT is now being explored for use in a variety of medical applications [1], and particularly is a well-recognized treatment for the destruction of tumors [2]. Photodynamic therapy uses light and a photosensitizer (a dye) to achieve its desired medical effect. A large number of naturally occurring and synthetic dyes have been evaluated as potential photosensitizers for PDT. Perhaps the most widely studied class of photosensitizers is tetrapyrrolic macrocyclic compounds. Among them, especially porphyrins and chlorins have been tested for their PDT efficacy. However, there is constant interest in new photosensitizer structures among them e.g. metal complexes but also other dyes like boron dipyrromethenes (BODIPYs). These BODIPYs were originally invented and are used as fluorescent dyes and labels, thus, by themselves they have only a limited potential for PDT and must be chemically modified to be employed as successful photosensitizers.

The photodynamic effect is only observed where the three necessary components, the photosensitizer, light and oxygen (which is present in the cells) are present at the same time [1]. This makes PDT in itself a local treatment which is opposed to the systemic action of chemotherapeutics. This localized treatment with PDT limits its efficacy mostly to localized tumors though recent reports also suggest a systemic, immunomodulating effect of PDT [3].

Another field of application for PDT is the antibacterial PDT that is the application of photosensitizers and light against localized bacterial infections. Bacteria are generally divided into two main groups based on the different properties and construction of their outer membranes, i.e. Gram-positive and Gram-negative bacteria. For antibacterial other dyes have been employed than for tumor therapy. Whereas for antitumor PDT amphiphilic photosensitizers have proven to be most effective, for antibacterial PDT usually more hydrophilic and water-soluble dyes have been employed [4]. Specifically, for Gram-negative bacteria water-soluble positively charged photosensitizers have been used [4].

SUMMARY

Embodiments include biologically active compounds that can be used as photosensitizers for a wide range of applications including light irradiation treatments such as PDT of cancer, infections and other diseases. One of the limitations of current PDT is the localized effect of the treatment which is due to the fact that light has to be delivered to the treatment site. This could be overcome by compounds which act as photosensitizers but additionally exhibit a light-independent toxicity against e.g. tumor cells or bacteria. Therefore, the structures described herein are active as photosensitizers but may also be used for a systemic treatment due to their light-independent toxicity against e.g. tumor cells or bacteria. In addition, due to their light-absorbing and light-emitting properties these compounds may also be employed for diagnostic purposes e.g. by detecting their fluorescence.

Embodiments include chemically stable boron dipyrromethene complexes useful for various medical applications such as photodynamic therapy. Yet, these compounds may also be used for the treatment of tumorous and other diseases without having to administer light, thereby also enabling a systemic treatment.

Embodiments include boron dipyrromethene complex structures incorporating a substituted 2,3,5,6-tetrafluorophenyl-dipyrromethene (2,3,5,6-tetrafluorophenyl-dipyrrin) unit or a substituted 3-nitrophenyl-dipyrromethene (3-nitrophenyl-dipyrrin) unit that can be used in the photodynamic therapy of tumors and other hyperproliferative diseases, dermatological disorders, viral or bacterial infections, otorhinolaryngology disorders, ophthalmological disorders or urological disorders. These compounds may also be used in the therapy of tumors and other hyperproliferative diseases, dermatological disorders, viral or bacterial infections, otorhinolaryngology disorders, ophthalmological disorders or urological disorders without the necessity to administer light. Still, these compounds may also be used in light-based diagnostics of tumors, hyperproliferative diseases, dermatological disorders, bacterial infections, otorhinolaryngology disorders, ophthalmological disorders or urological disorders. These compounds may also be used for the fluorescence diagnosis and PDT treatment of a non-tumorous indication such as arthritis and similar inflammatory diseases.

Embodiments include amphiphilic compounds that may be used in the PDT-treatment of tumors, dermatological disorders, viral or bacterial infections, otorhinolaryngology disorders, ophthalmological disorders or urological disorders; and also may be used in the treatment of tumors, dermatological disorders, viral or bacterial infections, otorhinolaryngology disorders, ophthalmological disorders or urological disorders without the necessity to administer light.

Embodiments include pharmaceutically acceptable formulations for the biologically active compounds herein described, such as a liposomal formulation to be injected avoiding undesirable effects like precipitation at the injection site or delayed pharmacokinetics of the compounds.

Briefly stated, embodiments include biologically active compounds and methods to obtain biologically active compounds that can be used as photosensitizers for diagnostic and therapeutic applications, particularly for PDT of cancer, infections and other hyperproliferative diseases, fluorescence diagnosis and PDT treatment of non-tumorous indications such as arthritis, inflammatory diseases, viral or bacterial infections, dermatological, otorhinolaryngology disorders, ophthalmological or urological disorders. As the compounds exhibit also toxicity against targets (tumor cells, bacteria, inflammation-related cells) without light these biologically active compounds may also be used for the light-independent treatment of such indications. Embodiments also include methods to synthesize boron dipyrromethene structures incorporating a substituted 2,3,5,6-tetrafluorophenyl-dipyrromethene (2,3,5,6-tetrafluorophenyl-dipyrrin) unit or a substituted 3-nitrophenyl-dipyrromethene (3-nitrophenyl-dipyrrin) unit. These dipyrromethenes (dipyrrins) may carry a variety of different substituents in the 4-position enabling a fine tuning of their biological or amphiphilic/hydrophilic properties. Embodiments also include compounds with increased anti-tumour and anti-bacterial efficacy. Specifically, this is achieved by substitution with bromine atoms and sugar moieties.

The above and other objects, features and advantages of the present invention will become apparent from the following description read in conjunction with the accompanying drawings.

DETAILED DESCRIPTION OF EMBODIMENTS

Figure 1:
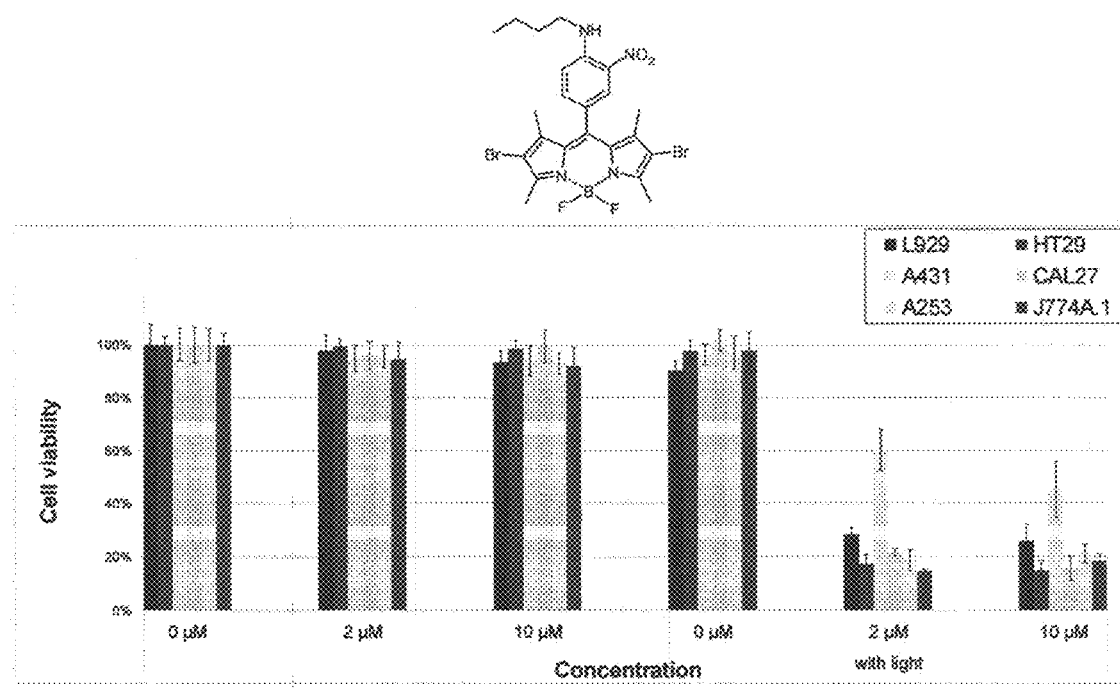
FIG. 1 shows the results of cell tests of 1,3,5,7-Tetramethyl-2,6-dibromo-8-(4-N-butylamino-3-nitrophenyl)-boron dipyrromethene.

Embodiments include biologically active compounds that may be used as photosensitizers for a wide range of light irradiation treatments such as PDT of cancer, hyperproliferative diseases, dermatological disorders, viral or bacterial infectious diseases, otorhinolaryngology disorders, ophthalmological disorders and/or urological disorders. Due to their light-independent toxicity they may also be used for the therapy of such diseases without the necessity to administer light. The compounds described herein have the advantage that they are easily produced and characterized, and allow further functionalization to enhance their activity, stability or make new applications possible. Embodiments also include methods to tailor compounds for desired applications, to increase target tissue selectivity and thus therapeutic efficacy. The compounds herein described enhance the effectiveness of biologically active compounds compared to the compounds described in prior art, by allowing to combine PDT and conventional chemotherapeutic or antibacterial treatment and by enhancing selectivity for target tissues over healthy surrounding tissues due to their tailored molecular structures and custom-made pharmacokinetic behavior depending on the particular application.

Embodiments include biologically active compounds that may be used for different medical indications and treatments, among them PDT, are boron dipyrromethene complex structures incorporating a substituted 2,3,5,6-tetrafluorophenyl-dipyrromethene (2,3,5,6-tetrafluorophenyl-dipyrrin) unit or a substituted 3-nitrophenyl-dipyrromethene (3-nitrophenyl-dipyrrin) unit. In addition, these compounds may be employed for fluorescence diagnosis and the treatment of non-tumorous indications such as arthritis and similar inflammatory diseases, extending their applications.

To obtain the novel compounds, embodiments use substituted dipyrromethanes (dipyrranes) which are converted to the corresponding boron dipyrromethenes (dipyrrins). The conversion is done by treating the corresponding dipyrromethane (dipyrrane) with a suitable oxidizing agent followed by treatment with a base and boron-trifluoride etherate [5]. In one embodiment a 2,3,4,5,6-pentafluorophenyl-dipyrromethane or a 4-fluoro-3-nitrophenyl-dipyrromethane is treated with a suitable nucleophile yielding the 4-substituted 2,3,5,6-tetrafluorophenyl-dipyrromethane or the 4-substituted-3-nitrophenyl-dipyrromethane, which are subsequently converted to the boron dipyrromethenes.

Alternatively, the 2,3,4,5,6-pentafluorophenyl-dipyrromethane or the 4-fluoro-3-nitrophenyl-dipyrromethane, is first converted to the boron dipyrromethene. This complex is then modified via nucleophilic aromatic substitution in the 4-position of the phenyl ring with a suitable nucleophile, specifically oxygen, nitrogen or sulfur nucleophiles carrying sugar moieties.

In a specifically preferred embodiment of the present invention the nucleophile is a sugar thiol compound, e.g. galactosyl-thiol or glucosyl-thiol.

In another step the boron dipyrromethene is modified with one or two bromine atoms in the positions 2 and 6, respectively. Such substitution may influence the photophysical properties of the compounds in a favorable way, e.g. increase their singlet oxygen quantum yields. Compounds modified in this way show a higher anti-tumor and anti-bacterial efficacy (see examples below).

In a specifically preferred embodiment of the invention the boron dipyrromethene is substituted with just one bromine atom. Such compounds exhibit high antibacterial activity.

Acceptable starting materials for the synthesis of the boron dipyrromethene complexes described herein may be dipyrromethanes (dipyrranes) which am readily accessible from the condensation reaction of pyrroles and aldehydes [6]. Suitable methods for this condensation have long been known in the art [6]. The dipyrromethane (dipyrrane) may then be modified with nucleophiles according to the literature [7]. The dipyrromethanes (dipyrranes)—whether modified with nucleophiles of not—may then be converted to the corresponding boron dipyrromethenes [5, 7, 8]. The pyrrole used for the condensation to the dipyrromethane may be unsubstituted or substituted by methyl groups, in a preferred embodiment the pyrrole is 2,4-dimethylpyrrole. The substitution of the boron dipyrromethene with bromine may be done for example with NBS, either in DCM, more slowly and with lower equivalents of NBS, to achieve monosubstitution [9,10] or in hexafluoroisopropanol, more rapidly and with more equivalents of NBS, to achieve disubstitution [11]. Modification of the boron dipyrromethene with sugar moieties may be achieved by the substitution of the para-fluorine atom of the 2,3,4,5,6-pentafluorophenyl or the 4-fluoro-3-nitrophenyl-substituent with suitable sugar nucleophiles which has been described for other pentafluorophenyl-substituted compounds in the literature, e.g. galactosyl-thiol or glucosyl-thiol [12].

The synthesis of compounds described herein is illustrated with the examples given below.

Example 1 shows the synthesis of substituted boron dipyrromethene complexes including amino- as well as glyco-substituted boron dipyrromethenes. For the latter examples given how these can be synthesized by substitution of the para-fluorine atom with sugar thiols. As well it is demonstrated with the examples that the substitution with specific nucleophiles may be done on the 1,3,5,7-tetramethyl as well as on the non-alkylated boron dipyrromethene.

Example 2 shows the synthesis of bromo-substituted boron dipyrromethenes. It is exemplified how by carefully selecting the reaction parameters (solvent, molar equivalents of NBS it is possible to achieve mono- as well disubstitution.

The specifically substituted boron dipyrromethene complexes as herein described are suitable to be used for the chemotherapy of cancer and other (hyper) proliferative diseases and infections as well as for the photodynamic therapy of those diseases, infections and conditions.

In some embodiments, treatment is accomplished by first incorporating the boron dipyrromethenes into a pharmaceutically acceptable application vehicle (e.g. ethanolic solution, liposomal formulation, or another pharmaceutical formulation) for delivery of the derivatives to a specific treatment site. After administering the derivatives in the vehicle to a treatment area, sufficient time is allowed so that the complexes preferentially accumulate in the diseased tissue and exert their effect. In case of PDT treatment, the treatment area is irradiated with light of a proper wavelength and sufficient power to activate the boron dipyrromethene complexes to induce necrosis or apoptosis in the cells of said diseased tissue. Due to their amphiphilic nature, the chemically stable boron dipyrromethene complexes of the present invention can be prepared in various pharmaceutically acceptable and active preparations for different administration methods, e.g. injections. In one embodiment such amphiphilic compounds are formulated into liposomes. This liposomal formulation can then be injected avoiding undesirable effects such as precipitation at the injection site or delayed pharmacokinetics.

Determination of dark toxicity (DT) and phototoxicity (example 3) of the boron dipyrromethenes as described in present disclosure in cell culture experiments with the HT29 tumor cell line and other cell lines shows the excellent properties of the compounds for use in PDT (examples 3.1 to 3.11).

The data presented in examples 3.1 to 3.11 show the results of the photodynamic treatment in a model cell line especially relevant for arthritis (J774A.1, a macrophage cell line) with compounds described in present disclosure, demonstrating the usefulness of the disclosed boron dipyrromethene complexes in the diagnosis and treatment of arthritis and similar inflammatory diseases.

The figures in example 4 (4.1 to 4.11) illustrate the effect of boron dipyrromethenes describe herein against bacteria, the Gram-positive germ *Staphylococcus aureus* as well as the Gram-negative *Pseudomonas aeruginosa*, proving that these compounds may also be used to treat bacterial infections. As can be seen from the examples, selected compounds (4.1, 4.2, 4.4 to 4.10) show a high antibacterial activity against S. aureus even in the absence of light (in the highest tested concentration of 100 µmol) exemplifying their principal suitability for a systemic treatment, especially since the compounds are on the other hand non-toxic to cells in the absence of light (cf. example 3). Also, some compounds may be specifically active against bacteria, whereat they exhibit only a low toxicity in cells (cf. example 4.5 in comparison with 3.12).

The following examples are presented to provide those of ordinary skill in the art with a full and illustrative disclosure and description of how to make the boron dipyrromethene complexes of the invention and show their chemotherapeutic and photodynamic activity and are not intended to limit the scope of what the inventor regards as the invention. Efforts have been made to ensure accuracy with respect to numbers used (e.g. amounts, temperature etc.), but some experimental errors and deviations should be accounted for. Also, best measures have been taken to name the compounds with their systematic IUPAC name, nevertheless the basic reference are the given structural formulas based on the experimental spectroscopic data.

All reactions were performed in standard round bottom flasks. Air-sensitive reactions were carried out under an argon gas protecting atmosphere. DCM, n-pentane, and methanol were purchased and used as received. Other solvents were purchased and distilled at reduced pressure. Purchased chemicals were used as received without further purification. All liquid reagents were added through syringes. Reactions were monitored by thin-layer chromatography (Merck, TLC Silica gel 60 $F_{254}$ and visualized under UV light (254 nm and 366 nm). Flash column chromatography was performed on silica gel (Fluka silica gel 60M, 40-63 µm). NMR spectra were recorded with JEOL ECX400, JEOL ECP500, Bruker Avance500, JEOL ECZ600, and Bruker Avance700. Multiplicity of the signals was assigned as follows: s=singlet, br s=broad singlet, d=doublet, t=triplet, dd=doublet of doublets, dt=doublet of triplets, dq=doublet of quartets, tt=triplet of triplets, ddd=doublet of doublets of doublets, ddt=doublet of doublets of triplets, sept=septet, m=multiplet, $m_c$=centered multiplet. Chemical shifts are reported relative to $CDCl_3$ ($^1H$: δ=7.26 ppm, $^{13}C$: δ=77.2 ppm), $CD_2Cl_2$ ($^1H$: δ=5.32 ppm, $^{13}C$: δ=53.8 ppm), THF-$d_8$ ($^1H$: δ=3.58 ppm, $^{13}C$: δ=67.6 ppm), and DMSO-$d_6$ ($^1H$: δ=2.50 ppm, $^{13}C$: δ=39.5 ppm). All $^{13}C$ NMR spectra are proton-decoupled and coupling constants are given in hertz (Hz). For a detailed peak assignment 2D spectra were measured (COSY, HMBC, and HMQC). HRMS analyses were carried out on an Agilent Technologies 6210 ESI-TOF (electrospray ionization, time of flight) instrument. UV/Vis spectra were recorded on a SPECORD S300 UV/Vis spectrometer (Analytic Jena) in quartz cuvettes (1 cm length). Specified melting points were recorded on a Reichert Thermovar Apparatus and are not corrected.

para-Amino substituted 1,3,5,7-tetramethyl BODIPYs, 8-pentafluorophenyl-1,3,5,7-tetramethyl BODIPY [8], para-alkoxy substituted BODIPYs, 8-pentafluorophenyl BODIPY [7], para-amino substituted BODIPY [13], para-4-amino-3-nitrophenyl substituted BODIPYs, 4-fluoro-3-nitrophenyl BODIPY [14] and par-amino substituted BODIPYs [15] were prepared according to the literature.

Example 1

Preparation of Substituted Boron Dipyrromethenes 1.1 8-(4-Fluoro-3-nitrophenyl)-1,3,5,7-tetramethyl-4,4-difluoro-4-bora-3a,4a-diaza-s-indacene

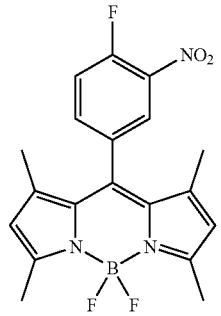

4-Fluoro-3-nitrobenzaldehyde (500 mg, 2.96 mmol) was dissolved in 35 mL of dichloromethane (DCM), 2,4-Dimethylpyrrole (900 µL, 8.87 mmol) and trifluoroacetic acid (37 µL, 0.48 mmol) were added and the mixture was stirred for 2.5 h at room temperature. After the indicated time, 2,3-dichloro-5,6-dicyano-1,4-benzoquinone (671 mg, 2.96 mmol) was added and stirred for additional 1 h at mom temperature. Afterwards, N,N-diisopropylethylamine (5.8 mL, 34.10 mmol) and $BF_3 \cdot OEt_2$ (5.8 mL, 45.70 mmol) were added and stirred for 1.5 h at room temperature. Water was added and the mixture was extracted with DCM several times. The combined organic phases were washed again with water, were concentrated (to about half of the volume), and filtered over a silica gel filled glass frit (DCM). The filtrate was dried with $Na_2SO_4$, filtrated, and evaporated to dryness. The crude product was purified by column chromatography (silica gel, n-hexane/EtOAc=9/1, v/v) to obtain the product as an orange-greenish solid (536 mg, 47%).

Mp: 171-175° C.

$^1H$ NMR (500 MHz, $CDCl_3$): δ (ppm)=1.43 (s, 6H, Me), 2.56 (s, 6H, Me), 6.03 (s, 2H, $H_{pyrrole}$), 7.47 (dd, J=10.3, 8.5 Hz, 1H, Ar—$H_{meta}$), 7.60 (ddd, J=8.5, 4.1, 2.2 Hz, 1H, Ar—$H_{ortho}$), 8.05 (dd, J=6.9, 2.3 Hz, 1H, Ar—$H_{ortho}$).

$^{13}C$ NMR (126 MHz, $CDCl_3$): δ (ppm)=14.8 (Me), 15.2 (Me), 119.7 (d, $J_{C-F}$=21.1 Hz, Ar—$C_{meta}$), 122.2 ($CH_{pyrrole}$), 126.5 (d, $J_{C-F}$+2.4 Hz, Ar—$C_{ortho}$), 131.1 ($C_{pyrrole}$), 132.1*, 135.7 (d, $J_{C-F}$=8.5 Hz, Ar—$C_{ortho}$) 136.7 ($C_{meso}$), 138.1 (d, $J_{C-F}$=8.0 Hz)*, 142.4 ($C_{pyrrole}$), 155.79 (d, $J_{C-F}$=268.0 Hz, Ar—$C_{para}$), 157.1 ($C_{pyrrole}$). *These signals could not be assigned exactly to the corresponding carbon atoms. They belong to the Ar—$C_{ipso}$ and the Ar—$C_{nitro}$ of the aryl moiety.

$^{19}F$ NMR (376 MHz, $CDCl_3$): δ (ppm)=−111.85 (s, 1F, CF), −145.85−−146.23 ($m_c$, 2F, $BF_2$).

HRMS (ESI-TOF): m/z calcd. for $C_{19}H_{18}BF_3N_3O_2^+$ [M+H]$^+$: 388.1439, found: 388.1438.

UV/Vis (DCM): $\lambda_{max}$ (nm) [log (ε/L mol$^{-1}$ cm$^{-1}$)]=507 [4.77].

General procedure for the substitution with amines: The BODIPY was dissolved in DCM, DMF or DMSO and the corresponding amine was added. The mixture was stirred for the indicated time at room temperature. Afterwards, the mixture was diluted with EtOAc and washed with water several times. The organic layer was dried with $Na_2SO_4$, filtered, and evaporated to dryness. The crude product was purified by column chromatography.

1.2 8-[4-(N-Butylamino)-3-nitrophenyl]-1,3,5,7-tetramethyl-4,4-difluoro-4-bora-3a,4a-diaza-s-indacene

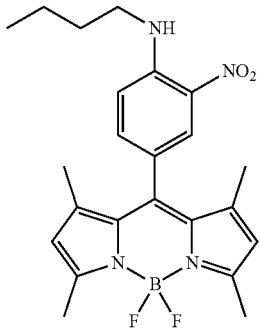

8-[4-(N-Butylamino)-3-nitrophenyl]-1,3,5,7-tetramethyl-4,4-difluoro-4-bora-3a,4a-diaza-s-indacene was prepared according to the general synthetic procedure. 8-(4-Fluoro-3-nitrophenyl)-1,3,5,7-tetramethyl-4,4-difluoro-4-bora-3a,4a-diaza-s-indacene (116 mg, 030 mmol) and n-butylamine (0.6 mL, 5.99 mmol) were dissolved in 10 mL of DCM. The mixture was stirred for 90 min. The crude product was purified by column chromatography (silica gel, EtOAc/n-hexane=1/2, v/v) to obtain the product as an orange solid (116 mg, 88%).

Mp: 133-139° C.

$^1$H NMR (500 MHz, CDCl$_3$): δ (ppm) 1.02 (t, J=7.4 Hz, 3H, Me$_{butyl}$), 1.49-1.58 (m, 8H, CH$_2$+Me), 1.75-1.81 (m, 2H, CH$_2$), 2.55 (s, 3H, Me), 3.36 (td, J=7.2, 4.7 Hz, 2H, CH$_2$), 6.00 (s, 2H, H$_{pyrrole}$), 7.00 (d, J=8.8 Hz, 1H, Ar—H$_{meta}$), 7.31 (dd, J=8.8, 2.1 Hz, 1H, Ar—H$_{ortho}$), 8.13 (d, J=2.1 Hz, 1H, Ar—H$_{ortho}$), 8.14-8.16 (m, 1H, NH).

$^{13}$C NMR (126 MHz, CDCl$_3$): δ (ppm)=13.9 (Me$_{butyl}$), 14.8 (Me), 15.4 (Me), 20.4 (CH$_2$), 31.1 (CH$_2$), 43.1 (CH$_2$), 114.9 (Ar—C$_{meta}$), 120.1 (C$_{meso}$), 121.4*, 121.6 (CH$_{pyrrole}$), 126.9 (Ar—C$_{ortho}$), 131.9 (C$_{pyrrole}$), 136.1 (Ar—C$_{ortho}$), 139.4*, 142.8 (C$_{pyrrole}$), 145.6 (Ar—C$_{para}$), 156.1 (C$_{pyrrole}$). *These signals could not be assigned exactly to the corresponding carbon atoms. They belong to the Ar—C$_{ipso}$ and the Ar—C$_{nitro}$ of the aryl moiety.

$^{19}$F NMR (376 MHz, CDCl$_3$): δ (ppm)=−145.60−−146.69 (m$_c$, 2F, BF$_2$).

HRMS (ESI-TOF): m/z calcd. for C$_{23}$H$_{27}$BF$_2$N$_4$O$_2$Na$^+$ [M+Na]$^+$: 463.2087, found: 463.2120, m/z calcd. for C$_{23}$H$_{27}$BF$_2$N$_4$O$_2$K$^+$ [M+K]$^+$: 479.1827, found: 479.1856, m/z calcd. for C$_{46}$H$_{54}$B$_2$F$_4$N$_8$O$_4$Na$^+$ [2M+Na]$^+$: 903.4282, found: 903.4319.

UV/Vis (DCM): λ$_{max}$ (nm) [log (ε/L mol$^{−1}$ cm$^{−1}$)]=505 [4.75].

1.3 8-[4-(N-2-Hydroxyethylamino)-3-nitrophenyl]-1,3,5,7-tetramethyl-4,4-difluoro-4-bora-3a,4a-diaza-s-indacene

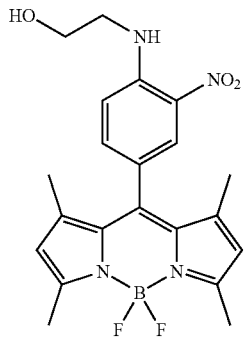

8-[4-(N-2-Hydroxyethylamino)-3-nitrophenyl]-1,3,5,7-tetramethyl-4,4-difluoro-4-bora-3a,4a-diaza-s-indacene was prepared according to the general synthetic procedure. 8-(4-Fluoro-3-nitrophenyl)-1,3,5,7-tetramethyl-4,4-difluoro-4-bora-3a,4a-diaza-s-indacene (100 mg, 0.26 mmol) and ethanolamine (0.3 mL, 5.17 mmol) were dissolved in 10 mL of DCM. The mixture was stirred for 24 h. The crude product was purified by column chromatography (silica gel, EtOAc) to obtain the product as an orange solid (96 mg, 87%).

Mp: 170-175° C.

$^1$H NMR (500 MHz, THF-d$_8$): δ (ppm)=1.57 (s, 6H, Me), 2.49 (s, 6H, Me), 3.48-3.51 (m, 2H, CH$_2$), 3.80-3.83 (m, 2H, CH$_2$), 4.23 (t, J=4.9 Hz, 1H, OH), 6.04 (s, 2H, H$_{pyrrole}$), 7.24 (d, J=8.8 Hz, 1H, Ar—H$_{meta}$), 7.42 (dd, J=8.7, 2.2 Hz, 1H, Ar—H$_{ortho}$), 8.15 (d, J=2.2 Hz, 1H, Ar—H$_{ortho}$), 8.41 (t, J=5.3 Hz, 1H, NH).

$^{13}$C NMR (126 MHz, THF-d$_8$): δ (ppm)=13.9 (Me), 14.9 (Me), 43.8 (CH$_2$), 112.3 (C$_{meso}$), 116.5 (Ar—C$_{meta}$), 121.2 (CH$_{pyrrole}$), 127.9 (Ar—C$_{ortho}$), 132.0 (C$_{pyrrole}$), 133.2*, 136.6 (Ar—C$_{ortho}$), 141.1*, 142.1 (C$_{pyrrole}$), 146.9 (Ar—C$_{para}$), 154.9 (C$_{pyrrole}$). *These signals could not be assigned exactly to the corresponding carbon atoms. They belong to the Ar—C$_{ipso}$ and the Ar—C$_{nitro}$ of the aryl moiety.

$^{19}$F NMR (376 MHz, THF-d$_8$): δ (ppm)=−145.98−−146.84 (m$_c$, 2F, BF$_2$).

HRMS (ESI-TOF): m/z calcd. for C$_{21}$H$_{23}$BF$_2$N$_4$O$_3$Na$^+$ [M+Na]$^+$: 451.1723, found: 451.1789, m/z calcd. for C$_{42}$H$_{46}$B$_2$F$_4$N$_8$O$_6$Na$^+$ [2M+Na]$^+$: 8793555, found: 8793647. UV/Vis (DCM): λ$_{max}$ (nm) [log (ε/L mol$^{−1}$ cm$^{−1}$)]= 505 [4.54].

1.4 8-[3-Nitro-4-(N-2-prop-2-enylamino)phenyl]-1,3,5,7-tetramethyl-4,4-difluoro-4-bora-3a,4a-diaza-s-indacene

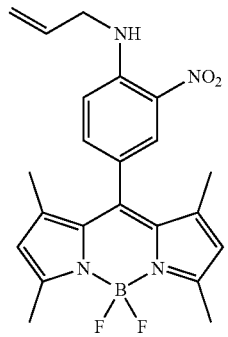

8-[3-Nitro-4-(N-2-prop-2-enylamino)phenyl]-1,3,5,7-tetramethyl-4,4-difluoro-4-bora-3a,4a-diaza-s-indacene was prepared according to the general synthetic procedure. 8-(4-Fluoro-3-nitrophenyl)-1,3,5,7-tetramethyl-4,4-difluoro-4-bora-3a,4a-diaza-s-indacene (132 mg, 0.34 mmol) and allylamine (0.3 mL, 3.40 mmol) were dissolved in 10 mL of DCM. The mixture was stirred for 24 h. The crude product was purified by column chromatography (silica gel, n-hexane/EtOAc=9/1, v/v) to obtain the product as an orange solid (124 mg, 86%).

Mp: 176-179° C.

$^1$H NMR (500 MHz, CDCl$_3$): δ (ppm) 1.53 (s, 6H, Me), 2.54 (s, 6H, Me), 4.05 (t, J=5.0 Hz, 2H, CH$_2$), 5.29-5.36 (m, 2H, H$_2$C=CH—), 5.95-6.02 (m, 3H, H$_{pyrrole}$+H$_2$C=CH—), 6.98 (d, J=8.8 Hz, 1H, Ar—H$_{meta}$), 7.30 (dd, J=8.8, 2.2 Hz, 1H, Ar—H$_{ortho}$), 8.14 (d, J=2.1 Hz, 1H, Ar—H$_{ortho}$), 8.28 (t, J=5.8 Hz, 1H, NH).

$^{13}$C NMR (126 MHz, CDCl$_3$): δ (ppm)=14.7 (Me), 15.3 (Me), 45.6 (CH$_2$), 115.2 (Ar—C$_{meta}$), 117.7 (H$_2$C=CH—), 121.6 (CH$_{pyrrole}$), 121.8*, 126.8 (Ar—C$_{ortho}$), 131.9 (C$_{pyrrole}$), 132.1 (C$_{meso}$), 132.7 (H$_2$C=CH—), 136.0 (Ar—C$_{ortho}$), 139.2*, 142.7 (C$_{pyrrole}$), 145.3 (Ar—C$_{para}$), 156.1 (C$_{pyrrole}$). *These signals could not be assigned exactly to the corresponding carbon atoms. They belong to the Ar—C$_{ipso}$ and the Ar—C$_{nitro}$ of the aryl moiety.

$^{19}$F NMR (376 MHz, CDCl$_3$): δ (ppm)=−145.57−−146.59 (m$_c$, 2F, BF$_2$).

HRMS (ESI-TOF): m/z calcd. for C$_{22}$H$_{23}$BF$_2$N$_4$O$_2$Na$^+$ [M+Na]$^+$: 447.1774, found: 447.1796, m/z calcd. for C$_{22}$H$_{23}$BF$_2$N$_4$O$_2$K$^+$ [M+K]$^+$: 463.1514, found: 463.1543, m/z calcd. for C$_{44}$H$_{46}$B$_2$F$_4$N$_8$O$_4$Na$^+$ [2M+Na]$^+$: 871.3656, found: 871.3699, m/z calcd. for CH$_{44}$H$_{46}$B$_2$F$_4$N$_2$O$_4$K$^+$ [2M+K]$^+$: 887.3396, found: 887.3442.

UV/Vis (DCM): λ$_{max}$ (nm) [log (ε/L mol$^{-1}$ cm$^{-1}$)]=504 [4.83].

1.5 8-[3-Nitro-4-(N-2-prop-2-ynylamino)phenyl]-1,3,5,7-tetramethyl-4,4-difluoro-4-bora-3a,4a-diaza-s-indacene

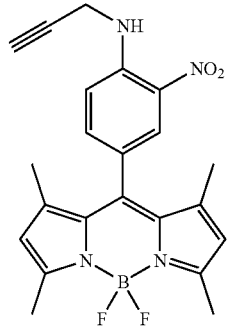

8-[3-Nitro-4-(N-2-prop-2-ynylamino)phenyl]-1,3,5,7-tetramethyl-4,4-difluoro-4-bora-3a,4a-diaza-s-indacene was prepared according to the general synthetic procedure. 8-(4-Fluoro-3-nitrophenyl)-1,3,5,7-tetramethyl-4,4-difluoro-4-bora-3a,4a-diaza-s-indacene (116 mg, 0.30 mmol) and propargylamine (0.4 mL, 5.99 mmol) were dissolved in 10 mL of DCM. The mixture was stirred for 24 h. The crude product was purified by column chromatography (silica gel, n-hexane/EtOAc=9/1, v/v) to obtain the product as an orange solid (56 mg, 44%).

Mp: 130-135° C.

$^1$H NMR (500 MHz, CDCl$_3$): δ (ppm)=1.51 (s, 6H, Me), 2.34 (t, J=2.5 Hz, 1H, CH), 2.55 (s, 6H, Me), 4.20 (dd, J=5.7, 2.5 Hz, 22H, CH$_2$), 6.00 (s, 2H, H$_{pyrrole}$), 7.12 (d, J=8.7 Hz, 1H, Ar—H$_{meta}$), 7.40 (dd, J=8.7, 2.1 Hz, 1H, Ar—H$_{ortho}$), 8.17 (d, J=2.1 Hz, 1H, Ar—H$_{ortho}$), 8.23 (t, J=5.6 Hz, 1H, NH).

$^{13}$C NMR (126 MHz, CDCl$_3$): δ (ppm)=14.8 (Me), 15.3 (Me), 32.97 (CH$_2$), 72.99 (CH), 78.4 (C), 115.1 (Ar—C$_{meta}$), 121.7*, 122.9 (CH$_{pyrrole}$), 126.9 (Ar—C$_{ortho}$), 131.8 (C$_{meso}$), 132.9 (C$_{pyrrole}$), 136.1 (Ar—C$_{ortho}$), 138.9*, 142.8 (C$_{pyrrole}$), 144.3 (Ar—C$_{para}$), 156.3 (C$_{pyrrole}$). *These signals could not be assigned exactly to the corresponding carbon atoms. They belong to the Ar—C$_{ipso}$ and the Ar—C$_{nitro}$ of the aryl moiety.

$^{19}$F NMR (376 MHz, CDCl$_3$): δ (ppm)=−145.56−−146.60 (m$_c$, 2F, BF$_2$).

HRMS (ESI-TOF): m/z calcd. for C$_2$H$_{21}$BF$_2$N$_4$O$_2$Na$^+$ [M+Na]$^+$: 445.1618, found: 445.1634, m/z calcd. for C$_{22}$H$_{21}$BF$_2$N$_4$O$_2$Na$^+$ [M+K]$^+$: 461.1357, found: 461.1492, m/z calcd. for C$_{44}$H$_{42}$B$_2$F$_4$N$_8$O$_4$Na$^+$ [2M+Na]$^+$: 867.3343, found: 867.3348.

UV/Vis (DCM): λ$_{max}$ (nm) [log (ε/L mol$^{-1}$ cm$^{-1}$)]=505 [4.47].

1.6 8-[4-(N-6-Methoxy-6-oxohexylamino)-3-nitrophenyl]-1,3,5,7-tetramethyl-4,4-difluoro-4-bora-3a,4a-diaza-s-indacene

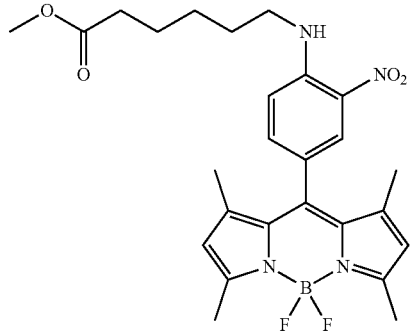

8-[4-(N-6-Methoxy-6-oxohexylamino)-3-nitrophenyl]-1,3,5,7-tetramethyl-4,4-difluoro-4-bora-3a,4a-diaza-s-indacene was prepared according to the general synthetic procedure. 8(4-Fluoro-3-nitrophenyl)-1,3,5,7-tetramethyl-4,4-difluoro-4-bora-3a,4a-diaza-s-indacene (200 mg, 0.52 mmol), methyl-6-aminohexanoate hydrochloride (939 mg, 5.17 mmol), and N-diisopropylamine (1.8 mL, 10.33 mmol) were dissolved in 20 mL DCM. The mixture was stirred for 72 h. The crude product was purified by column chromatography (silica gel, n-hexane/EtOAc=9/1, v/v, then n-hexane/EtOAc=4/1, v/v) to obtain the product as an orange solid (80 mg, 30%).

Mp: 123-125° C.

$^1$H NMR (500 MHz, CDCl$_3$): δ (ppm)=1.49-1.57 (m, 8H, Me+CH$_2$), 1.70-1.76 (m, 2H, CH$_2$), 1.77-1.83 (m, 2H, CH$_2$), 2.36 (t, J=7.4 Hz, 2H, CH$_2$), 2.54 (s, 6H, Me), 3.36 (td, J=7.1, 5.0 Hz, 2H, CH$_2$), 3.67 (s, 3H, Me$_{OMe}$), 5.99 (s, 2H, H$_{pyrrole}$), 6.98 (d, J=8.8 Hz, 1H, Ar—H$_{meta}$), 7.31 (dd, J=8.7, 2.2 Hz, 1H, Ar—H$_{ortho}$), 8.11-8.14 (m, 2H, Ar—H$_{ortho}$+NH).

$^{13}$C NMR (126 MHz, CDCl$_3$): δ (ppm)=14.7 (Me), 15.3 (Me), 24.6 (CH$_2$), 26.7 (CH$_2$), 28.7 (CH$_2$), 33.9 (CH$_2$), 43.1 (CH$_2$), 51.7 (Me$_{OMe}$), 114.8 (Ar—C$_{meta}$), 121.5*, 121.6 (CH$_{pyrrole}$), 126.9 (Ar—C$_{ortho}$), 131.9 (C$_{pyrrole}$), 131.9 (C$_{meso}$), 136.1 (Ar—C$_{ortho}$), 139.3*, 142.7 (C$_{pyrrole}$), 145.5 (Ar—C$_{para}$), 156.1 (C$_{pyrrole}$), 173.95 (CO). *These signals could not be assigned exactly to the corresponding carbon atoms. They belong to the Ar—C$_{ipso}$ and the Ar—C$_{nitro}$ of the aryl moiety.

$^{19}$F NMR (376 MHz, CDCl$_3$): δ (ppm)=−145.57−−146.63 (m$_c$, 2F, BF$_2$).

HRMS (ESI-TOF): m/z calcd. for C$_{26}$H$_{31}$BFN$_4$O$_4$$^+$ [M−F]$^+$: 493.2417, found: 493.2410, m/z calcd. for C$_{26}$H$_{31}$BF$_2$N$_4$O$_4$Na$^+$ [M+Na]$^+$: 535.2299, found: 535.2298.

UV/Vis (DCM): λ$_{max}$ (nm) [log (ε/L mol$^{-1}$ cm$^{-1}$)]=504 [4.66].

1.7 8-[4-(N,N-Dibutylamino)-3-nitrophenyl]-1,3,5,7-tetramethyl-4,4-difluoro-4-bora-3a,4a-diaza-s-indacene

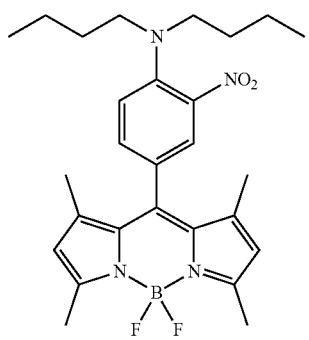

8-[4-(N,N-Dibutylamino)-3-nitrophenyl]-1,3,5,7-tetramethyl-4,4-difluoro-4-bora-3a,4a-diaza-s-indacene was prepared according to the general synthetic procedure. 8-(4-Fluoro-3-nitrophenyl)-1,3,5,7-tetramethyl-4,4-difluoro-4-bora-3a,4a-diaza-s-indacene (200 mg, 0.52 mmol) and N,N-dibutylamine (1.60 mL, 9.66 mmol) were dissolved in 10 mL of DCM. The mixture was stirred for 24 h. The crude product was purified by column chromatography (silica gel, n-hexane/EtOAc=9/1, v/v) to obtain the product as an orange solid (90 mg, 35%).

Mp: 95-99° C.

$^1$H NMR (500 MHz, CDCl$_3$): δ (ppm)=0.87 (t, J=7.4 Hz, 61H, Me$_{butyl}$), 1.25-1.32 (m, 4H, CH$_2$), 1.50-1.56 (m, 10H, CH$_2$+Me), 2.55 (s, 6H, Me), 3.20 (t, J=7.3 Hz, 4H, CH$_2$), 6.00 (s, 2H, H$_{pyrrole}$), 7.28 (br s, 2H, Ar—H$_{meta}$+Ar—H$_{ortho}$), 7.65 (t, J=1.2 Hz, 1H, Ar—H$_{ortho}$).

$^{13}$C NMR (126 MHz, CDCl$_3$): δ (ppm)=13.9 (Me$_{butyl}$), 14.8 (Me), 14.99 (Me), 20.2 (CH$_2$), 29.5 (CH$_2$), 52.2 (CH$_2$), 121.7 (CH$_{pyrrole}$), 122.6 (Ar—C$_{meta}$), 126.3 (Ar—C$_{ortho}$), 131.7 (132.7 (Ar—C$_{ortho}$), 138.96*. 142.1*, 142.8 (C$_{pyrrole}$), 144.9 (Ar—C$_{para}$), 156.2 (C$_{pyrrole}$). *These signals could not be assigned exactly to the corresponding carbon atoms. They belong to the Ar—C$_{ipso}$ and the Ar—C$_{nitro}$ of the aryl moiety.

$^{19}$F NMR (376 MHz, CDCl$_3$): δ (ppm)=−145.61−−146.64 (m$_c$, 2F, BF).

HRMS (ESI-TOF): m/z calcd. for C$_{27}$H$_{35}$BF$_2$N$_4$O$_2$Na$^+$ [M+Na]$^+$: 519.2713, found: 519.2713.

UV/Vis (DCM): λ$_{max}$ (nm) [log (ε/L mol$^{-1}$ cm$^{-1}$)]=505 [4.62].

1.8 8-[4-(N-1-Hydroxymethyl-2-hydroxyethyl-amino)-3-nitrophenyl]-1,3,5,7-tetramethyl-4,4-difluoro-4-bora-3a,4a-diaza-s-indacene

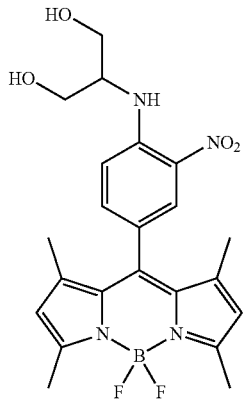

8-[4-(N-1-Hydroxymethyl-2-hydroxyethylamino)-3-nitrophenyl]-1,3,5,7-tetramethyl-4,4-difluoro-4-bora-3a,4a-diaza-s-indacene was prepared according to the general synthetic procedure. 8(4-Fluoro-3-nitrophenyl)-1,3,5,7-tetramethyl-4,4-difluoro-4-bora-3a,4a-diaza-s-indacene (200 mg, 0.52 mmol) and 2-amino-1,3-dihydroxypropane (706 mg, 7.75 mmol) were dissolved in 20 mL DMSO. The mixture was stirred for 24 h. The crude product was purified by column chromatography (silica gel, EtOAc) to obtain the product as an orange-green solid (40 mg, 23%).

Mp: 110-116° C.

$^1$H NMR (500 MHz, THF-$d_8$): δ (ppm) 1.58 (s, 6H, Me), 2.48 (s, 6H, Me), 3.72-3.76 (m, 2H, $CH_2$), 3.80-3.82 (m, 3H, $CH_2$+CH), 4.25 (br s, 2H, OH), 6.04 (s, 2H, $H_{pyrrole}$), 7.33 (d, J=8.9 Hz, 1H, Ar—$H_{meta}$), 7.39 (dd, J=8.8, 2.1 Hz, 1H, Ar—$H_{ortho}$), 8.14 (d, J=2.0 Hz, 1H, Ar—$H_{ortho}$), 8.59 (d, J=7.3 Hz, 1H, NH).

$^{13}$C NMR (126 MHz, THF-$d_8$): δ (ppm) 14.7 (Me), 15.5 (Me), 56.9 (CH), 61.5 ($CH_2$), 116.9 (Ar—$C_{meta}$), 122.0 ($CH_{pyrrole}$), 122.1*, 127.8 (Ar—$C_{ortho}$), 132.9 ($C_{pyrrole}$), 133.2*, 136.7 (Ar—$C_{ortho}$), 141.2 ($C_{meso}$), 143.5 ($C_{pyrrole}$), 146.5 (Ar—$C_{para}$), 156.5 ($C_{pyrrole}$). *These signals could not be assigned exactly to the corresponding carbon atoms. They belong to the Ar—$C_{ipso}$ and the Ar—$C_{nitro}$ of the aryl moiety.

$^{19}$F NMR (376 MHz, THF-$d_8$): δ (ppm)=−146.71−−147.02 ($m_c$, 2F, $BF_2$).

HRMS (ESI-TOF): m/z calcd. for $C_{22}H_{25}BFN_4O_4^+$ [M−F]$^+$: 439.1947, found: 439.1957, m/z calcd. for $C_{22}H_{26}BF_2N_4O_4^+$ [M+H]$^+$: 459.2010, found: 459.2016, m/z calcd. for $C_{22}H_{25}BF_2N_4O_4Na^+$ [M+Na]$^+$: 481.1829, found: 481.1837, m/z calcd. for $C_{22}H_{25}BF_2N_4O_4K^+$ [M+K]$^+$: 497.1569. found: 497.1575.

UV/Vis (MeOH): $\lambda_{max}$ (nm) [log (ε/L mol$^{-1}$ cm$^{-1}$)]=501 [4.80].

1.9 8-[4-(N-Prop-2-ynylamino)-2,3,5,6-tetrafluorophenyl]-1,3,5,7-tetramethyl-4,4-difluoro-4-bora-3a,4a-diaza-s-indacene

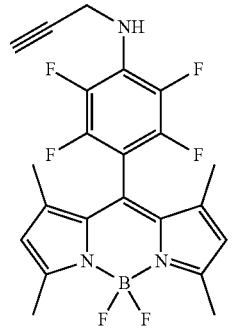

8-[4-(N-Prop-2-ynylamino)-2,3,5,6-tetrafluorophenyl]-1,3,5,7-tetramethyl-4,4-difluoro-4-bora-3a,4a-diaza-s-indacene was prepared according to the general synthetic procedure. 8-Pentafluorophenyl-1,3,5,7-tetramethyl-4,4-difluoro-4-bora-3a,4a-diaza-s-indacene (which was prepared according to the literature: [8]) (200 mg, 0.48 mmol) and propargylamine (0.31 mL, 4.83 mmol) were dissolved in 5 mL of DMF. The mixture was stirred for 24 h. The crude product was purified by column chromatography (silica gel, EtOAc/n-hexane=119, v/v) to obtain the product as an orange solid (53 mg, 23%).

Mp: 215-221° C.

$^1$H NMR (500 MHz, CDCl$_3$): δ (ppm)=1.66 (s, 6H, Me), 2.27-2.28 (m, 1H, CH), 2.56 (s, 6H, Me), 4.22 (br s, 2H, $CH_2$), 6.02 (s, 2H, $H_{pyrrole}$).

$^{13}$C NMR (126 MHz, CDCl$_3$): δ (ppm) 13.6 (Me), 14.9 (Me), 35.8 ($CH_2$), 72.9 (C), 121.95 ($CH_{pyrrole}$), 131.8 ($C_{pyrrole}$), 133.8 (Ar—$C_{para}$), 142.1 ($C_{pyrrole}$), 157.1 ($C_{pyrrole}$).

$^{19}$F NMR (376 MHz, CDCl$_3$): δ (ppm)=−142.41 (d, J=18.8 Hz, 2F, $CF_{meta}$), −145.89−−146.15 ($m_c$, 2F, $BF_2$), −157.16 (d, J=18.0 Hz, 2F, $CF_{ortho}$).

HRMS (ESI-TOF): m/z calcd. for $C_{22}H_{18}BF_6N_3Na^+$ [M+Na]$^+$: 472.1390, found: 472.1407, m/z calcd. for $C_{22}H_{18}BF_6N_3K^+$ [M+K]$^+$: 488.1130, found: 488.1130, m/z calcd. for $C_{44}H_{36}B_2F_{12}N_6Na^+$ [2M+Na]$^+$: 921.2888, found: 921.2910.

UV/Vis (DCM): $\lambda_{max}$ (nm) [log (ε/L mol$^{-1}$ cm$^{-1}$)]=515 [4.72].

1.10 8-[4-(N-2-Hydroxyethylamino)-2,3,5,6-tetrafluorophenyl]-1,3,5,7-tetramethyl-4,4-difluoro-4-bora-3a,4a-diaza-s-indacene

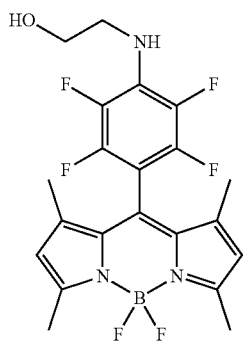

8-[4-(N-2-Hydroxyethylamino)-2,3,5,6-tetrafluorophenyl]-1,3,5,7-tetramethyl-4,4-difluoro-4-bora-3a,4a-diaza-s-indacene was prepared according to the general synthetic procedure. 8-Pentafluorophenyl-1,3,5,7-tetramethyl-4,4-difluoro-4-bora-3a,4a-diaza-s-indacene (which was prepared according to the literature: [8]) (200 mg, 0.48 mmol) and ethanolamine (0.50 mL, 8.93 mmol) were dissolved in 5 mL of DMF. The mixture was stirred for 4 h. The crude product was purified by column chromatography (silica gel, EtOAc/n-hexane=1/1, v/v) to obtain the product as an orange-green solid (81 mg, 41%).

Mp: 154-157° C.

$^1$H NMR (500 MHz, THF-d$_8$): δ (ppm) 1.70 (s, 6H, Me), 2.49 (s, 6H, Me), 3.52-3.56 (m, 2H, CH$_2$), 3.69 (t, J=5.5 Hz, 2H, CH$_2$), 4.06 (br s, 1H, OH), 5.57 (s, 1H, NH), 6.09 (s, 2H, H$_{pyrrole}$).

$^{13}$C NMR (126 MHz, THF-d$_8$): δ (ppm)=13.8 (Me), 14.8 (Me), 48.7 (CH$_2$), 62.2 (CH$_2$), 100.03 (t, J$_{C-F}$=19.8 Hz, Ar—C$_{ipso}$), 122.5 (CH$_{pyrrole}$), 126.5 (C$_{meso}$), 131.4-131.6 (m, Ar—C$_{para}$), 132.95 (C$_{pyrrole}$), 139.03 (dd, J$_{C-F}$=242.1, 25.0 Hz, Ar—C$_{meta}$), 142.9 (C$_{pyrrole}$) 145.27 (ddt, J$_{C-F}$=242.3, 8.6, 4.1 Hz, Ar—C$_{ortho}$), 157.8 (C$_{pyrrole}$).

$^{19}$F NMR (376 MHz, THF-d$_8$): δ (ppm)=-145.87 (d, J=17.7 Hz, 2F, CF$_{meta}$), -146.58--146.84 (m$_C$, 2F, BF$_2$), -161.12 (d, J=18.3 Hz, 2F, CF$_{ortho}$).

HRMS (ESI-TOF): m/z calcd. for C$_{21}$H$_{20}$BF$_6$N$_3$ONa$^+$ [M+Na]$^+$: 478.1496, found: 478.1524, m/z calcd. for C$_{21}$H$_{20}$BF$_6$N$_3$OK$^+$ [M+K]$^+$: 494.1235, found: 494.1267, m/z calcd. for C$_{42}$H$_{40}$B$_2$F$_{12}$N$_6$O$_2$Na$^+$ [2M+Na]$^+$: 933.3099, found: 933.3149.

UV/Vis (DCM): λ$_{max}$ (nm) [log (ε/L mol$^{-1}$ cm$^{-1}$)]=515 [4.89].

General procedure for the substation with thio-carbohydrates: The BODIPY was dissolved in DMF and the corresponding thio-carbohydrate was added. The mixture was stirred for the indicated time at room temperature. Afterwards, 5 mL of water was added and then evaporated to dryness. The crude product was purified by column chromatography and recrystallization.

1.11 8-[3-Nitro-4-(1'-thio-β-D-glucosyl)phenyl]-1,3,5,7-tetramethyl-4,4-difluoro-4-bora-3a,4a-diaza-s-indacene

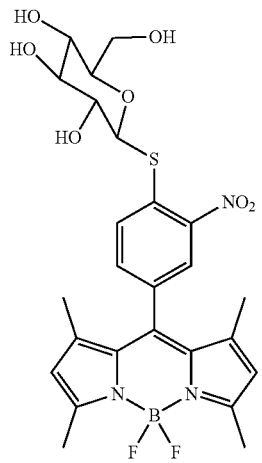

8-[3-Nitro-4-(1'-thio-D-glucosyl)phenyl]-1,3,5,7-tetramethyl-4,4-difluoro-4-bora-3a,4a-diaza-s-indacene was prepared according to the general synthetic procedure. 8-(4-Fluoro-3-nitrophenyl)-1,3,5,7-tetramethyl-4,4-difluoro-4-bora-3a,4a-diaza-s-indacene (100 mg, 0.26 mmol) and 1'-thio-β-D-glucose sodium salt (67 mg, 0.31 mmol) were dissolved in 5 mL of DMF. The mixture was stirred for 15 min. The crude product was purified by column chromatography (silica gel, DCM/MeOH=6/1, v/v) and recrystallization (DCM+a few drops of MeOH/n-hexane) to obtain the product as an orange solid (67 mg, 46%).

Mp: 158-163° C.

$^1$H NMR (600 MHz, THF-d$_8$): δ (ppm) 1.48 (d, J=6.6 Hz, 6H, Me), 2.50 (s, 6H, Me), 3.31-3.37 (m, 3H, 2'-H+3'-H+4'-H), 3.42 (ddd, J=8.9, 5.9, 2.5 Hz, 1H, 5'-H), 3.57-3.60 (m, 4H, 6'-H+THF), 3.81 (dd, J=12.0, 2.5 Hz, 1H, 6'-H), 3.88 (br s, 1H, OH), 4.61 (br s, 1H, OH), 4.84 br s, 1H, OH), 4.88-4.89 (m, 1H, 1'-H), 5.07 (br s, 1H, OH), 6.07 (d, J=3.6 Hz, 2H, H$_{pyrrole}$), 7.65 (dd, J=8.3, 2.0 Hz, 1H, Ar—H$_{ortho}$), 8.12 (d, J=8.3 Hz, 1H, Ar—H$_{meta}$), 8.23 (d, J=1.9 Hz, 1H, Ar—H$_{ortho}$).

$^{13}$C NMR (151 MHz, THF-d$_8$): δ (ppm)=14.4 (Me), 15.1 (Me), 62.7 (6'-C), 70.9 (4'-C), 73.6 (2'-C), 79.9 (3'-C), 81.9 (5'-C), 86.4 (1'-C), 121.99 (CH$_{pyrrole}$), 126.3 (Ar—C$_{ortho}$), 130.7 (Ar—C$_{meta}$), 131.9 (C$_{pyrrole}$), 132.9 (Ar—C$_{para}$), 134.3 (Ar—C$_{ortho}$), 138.1*, 139.3*, 143.2 (C$_{pyrrole}$), 148.0 (C$_{meso}$), 156.7 (C$_{pyrrole}$). *These signals could not be assigned exactly to the corresponding carbon atoms. They belong to the Ar—C$_{ipso}$ and the Ar—C$_{nitro}$ of the aryl moiety.

$^{19}$F NMR (376 MHz, THF-d$_8$): δ (ppm)=-146.71--146.89 (m$_c$, 2F, BF$_2$).

HRMS (ESI-TOF): m/z calcd. for C$_{25}$H$_{30}$N$_3$O$_7$S$^+$ [M−BF$_2$+H]$^+$: 516.1799, found: 516.1802, m/z calcd. for C$_{25}$H$_{28}$BF$_2$N$_3$O$_7$SNa$^+$ [M+Na]$^+$: 586.1601, found: 586.1614.

UV/Vis (MeOH): λ$_{max}$ (nm) [log (ε/L mol$^{-1}$ cm$^{-1}$)]=382 [3.58], 503 [4.52].

1.12 8-[3-Nitro-4-(1'-thio-β-D-galactosyl)phenyl]-1,3,5,7-tetramethyl-4,4-difluoro-4-bora-3a,4a-diaza-s-indacene

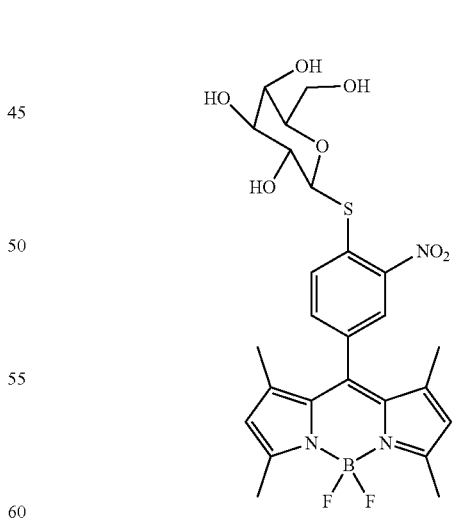

8-[3-Nitro-4-(1'-thio-β-D-galactosyl)phenyl]-1,3,5,7-tetramethyl-4,4-difluoro-4-bora-3a,4a-diaza-s-indacene was prepared according to the general synthetic procedure. 8-(4-Fluoro-3-nitrophenyl)-1,3,5,7-tetramethyl-4,4-difluoro-4-bora-3a,4a-diaza-s-indacene (100 mg, 0.26 mmol) and 1'-thio-β-D-galactose sodium salt (68 mg, 0.31 mmol) were dissolved in 5 mL of DMF. The mixture was stirred for 15 min. The crude product was purified by column chromatography (silica gel, DCM/MeOH=9/1, v/v) and recrystallization (DCM+a few drops of MeOH/n-hexane) to obtain the product as an orange-red solid (116 mg, 80%).

Mp: 151-158° C.

$^1$H NMR (500 MHz, THF-d$_8$): δ (ppm)=1.48 (d, J=5.3 Hz, 6H, Me), 2.50 (s, 6H, Me), 3.46 (d, J=8.4 Hz, 1H, 3'-H), 3.64-3.67 (m, 2H, 5'-H+6'-H), 3.70-3.74 (m, 2H, 2'-H+6'-H), 3.89 (br s, 1H, 4'-H), 4.00 (br s, 1H, OH), 4.53 (br s, 1H, OH), 4.79 (d, J=9.7 Hz, 1H, 1'-H), 4.89 (br s, 1H, OH), 6.06 (s, 2H, H$_{pyrrole}$), 7.62 (dd, J=8.3, 1.9 Hz, 1H, Ar—H$_{ortho}$), 8.19 (d, J=8.4 Hz, 1H, Ar—H$_{meta}$), 8.21 (d, J=1.9 Hz, 1H, Ar—H$_{ortho}$).

$^{13}$C NMR (126 MHz, THF-d$_8$): δ (ppm)=14.8 (Me), 15.4 (Me), 62.7 (6'-C), 70.1 (4'-C), 70.9 (2'-C), 79.6 (3'-C), 80.95 (5'-C), 87.3 (1'-C), 122.6 (CH$_{pyrrole}$), 126.3 (Ar—C$_{ortho}$), 131.5 (Ar—C$_{meta}$), 133.2 (C$_{pyrrole}$), 134.4 (Ar—C$_{ortho}$), 138.5*, 139.7 (Ar—C$_{para}$), 143.5*, 143.6 (C$_{pyrrole}$), 148.5 (C$_{meso}$), 157.1 (C$_{pyrrole}$). *These signals could not be assigned exactly to the corresponding carbon atoms. They belong to the Ar—C$_{ipso}$ and the Ar—C$_{nitro}$ of the aryl moiety.

$^{19}$F NMR (376 MHz, THF-d$_8$): δ (ppm)=−146.68−−146.94 (m$_c$, 2F, BF$_2$).

HRMS (ESI-TOF): m/z calcd. for $C_{25}H_{30}N_3O_7S^+$ [M−BF$_2$+H]$^+$: 516.1799, found: 516.1836, m/z calcd. for $C_{25}H_{28}BF_2N_3O_7SNa^+$ [M+Na]$^+$: 586.1601, found: 586.1642, m/z calcd. for $C_{25}H_{28}BF_2N_3O_7SK^+$ [M+K]$^+$: 602.1341, found: 602.1380.

UV/Vis (MeOH): λ$_{max}$ (nm) [log (ε/L mol$^{-1}$ cm$^{-1}$)]=359 [3.89], 502 [4.77].

1.13 8-[2,3,5,6-Tetrafluoro-4-(1'-thio-β-D-glucosyl)phenyl]-1,3,5,7-tetramethyl-4,4-difluoro-4-bora-3a,4a-diaza-s-indacene

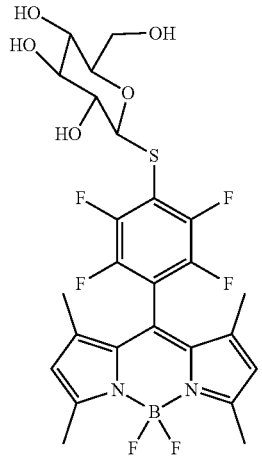

8-[2,3,5,6-Tetrafluoro-4-(1'-thio-β-D-glucosyl)phenyl]-1,3,5,7-tetramethyl-4,4-difluoro-4-bora-3a,4a-diaza-s-indacene was prepared according to the general synthetic procedure. 8-Pentafluorophenyl-1,3,5,7-tetramethyl-4,4-difluoro-4-bora-3a,4a-diaza-s-indacene (which was prepared according to the literature: [8]) (100 mg, 0.24 mmol) and 1'-thio-β-D-glucose sodium salt (63 mg, 0.29 mmol) were dissolved in 5 mL of DMF. The mixture was stirred for 30 min. The crude product was purified by column chromatography (silica gel, DCM/MeOH=6/1, v/v) and recrystallization (DCM+a few drops of MeOH/n-hexane) to obtain the product as an orange solid (98 mg, 69%).

Mp: 180-183° C.

$^1$H NMR (500 MHz, THF-d$_8$): δ (ppm) 1.66 (s, 6H, Me), 2.51 (s, 6H, Me), 3.16-3.20 (m, 1H, 3'-H), 3.25-3.29 (m, 2H, 2'-H+5'-H), 3.43 (dd, J=7.2, 4.9 Hz, 1H, 4-H), 3.50 (ddd, J=11.7, 7.1, 5.1 Hz, 1H, 6'-H), 3.63 (ddd, J=11.5, 4.8, 2.7 Hz, 1H, 6'-H), 4.50 (s, 1H, OH), 4.77 (s, 1H, OH), 4.88 (d, J=8.6 Hz, 1H, 1'-H), 4.97 (s, 1H, OH), 6.12 (s, 2H, H$_{pyrrole}$).

$^{13}$C NMR (126 MHz, THF-d$_8$): δ (ppm) 13.9 (Me), 14.8 (Me), 62.9 (6'-C), 71.5 (2'-C), 76.2 (4'-C), 79.98 (3'-C), 82.7 (5'-C), 85.8 (1'-C), 119.4 (Ar—C$_{ipso}$), 122.9 (CH$_{pyrrole}$), 125.0 (Ar—C$_{para}$), 131.8 (C$_{pyrrole}$), 142.95 (C$_{pyrrole}$), 158.5 (C$_{pyrrole}$).

$^{19}$F NMR (376 MHz, THF-d$_8$): δ (ppm)=−132.29−−132.39 (m, 2F, CF$_{ortho}$), −142.89 (dd, J=24.8, 11.1 Hz, 2F, CF$_{meta}$), −146.50−−146.75 (m, 2F, BF$_2$).

HRMS (ESI-TOF): m/z calcd. for $C_{25}H_{26}BF_6N_2O_5S^+$ [M+H]$^+$: 591.1554, found: 591.1565, m/z calcd. for $C_{25}H_{25}BF_6N_2O_5SNa^+$ [M+Na]$^+$: 613.1374, found: 613.1390, m/z calcd. for $C_{25}H_{25}BF_6N_2O_5SK^+$ [M+K]$^+$: 629.1113, found: 629.1137, m/z calcd. for $C_{50}H_{50}B_2F_2N_6O_{10}S_2Na^+$ [2M+Na]$^+$: 1203.2855, found: 1203.2887.

UV/Vis (MeOH): λ$_{max}$ (nm) [log (ε/L mol$^{-1}$ cm$^{-1}$)]=513 [4.72].

1.14 8-[2,3,5,6-Tetrafluoro-4-(1'-thio-β-D-galactosyl)phenyl]-1,3,5,7-tetramethyl-4,4-difluoro-4-bora-3a,4a-diaza-s-indacene

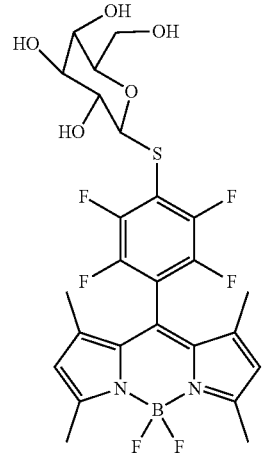

8-[2,3,5,6-Tetrafluoro-4-(1'-thio-β-D-galactosyl)phenyl]-1,3,5,7-tetramethyl-4,4-difluoro-4-bora-3a,4a-diaza-s-indacene was prepared according to the general synthetic procedure. 8-Pentafluorophenyl-1,3,5,7-tetramethyl-4,4-difluoro-4-bora-3a,4a-diaza-s-indacene (which was prepared according to the literature: [8]) (200 mg, 0.48 mmol) and 1'-thio-β-D-galactose sodium salt (126 mg, 0.58 mmol) were dissolved in 5 mL of DMF. The mixture was stirred for 20 min. The crude product was purified by column chromatography (silica gel, DCM/MeOH=9/1, v/v) and recrystallization (DCM+a few drops of MeOH/n-hexane) to obtain the product as a red solid (130 mg, 46%).

Mp: 213-216° C.

$^1$H NMR (500 MHz, THF-d$_8$): δ (ppm)=1.66 (s, 6H, Me), 2.51 (s, 6H, Me), 3.37 (ddd, J=9.2, 6.3, 3.3 Hz, 1H, 3'-H), 3.43 (dd, J=6.6, 6.0 Hz, 1H, 5-H), 3.47 (dd, J=10.6, 5.6 Hz, 1H, 6'-H), 3.56-3.61 (m, 2H, 4'-H+6'-H), 3.66 (t, J=5.5 Hz, 1H, OH), 3.82 (t, J=3.3 Hz, 1H, 2'-H), 3.95 (d, J=4.1 Hz, 1H, OH), 4.39 (d, J=6.3 Hz, 1H, OH), 4.76-4.77 (m, 1H, 1'-H), 4.79 (d, 1H, OH), 6.12 (s, 2H$_{pyrrole}$).

$^{13}$C NMR (126 MHz, THF-d$_8$): δ (ppm)=13.9 (Me), 14.8 (Me), 62.0 (6'-C), 70.0 (2'-C), 73.3 (4'-C), 76.5 (3'-C), 81.3 (5'-C), 86.3 (1'-C), 115.0 (Ar—C$_{ipso}$), 122.9 (CH$_{pyrrole}$), 125.1 (C$_{meso}$), 131.8 (C$_{pyrrole}$), 131.9 (Ar—C$_{para}$), 142.97 (C$_{pyrrole}$), 158.5 (C$_{pyrrole}$).

$^{19}$F NMR (376 MHz, THF-d$_8$): δ (ppm)=−131.26 (dd, J=25.4, 11.7 Hz, 2F, CF$_{ortho}$), −142.24 (dd, J=25.5, 11.7 Hz 2F, CF$_{meta}$), −145.71--145.96 ((m$_c$, 2F, BF$_2$).

HRMS (ESI-TOF): m/z calcd. for C$_{25}$H$_{25}$BF$_6$N$_2$O$_5$SNa$^+$ [M+Na]$^+$: 613.1374, found: 613.1402.

UV/Vis (MeOH): λ$_{max}$ (nm) [log (ε/L mol$^{-1}$ cm$^{-1}$)]=513 [4.54].

1.15 8-[3-Nitro-4-(1'-thio-β-D-glucosyl)phenyl]-4,4-difluoro-4-bora-3a,4a-diaza-s-indacene

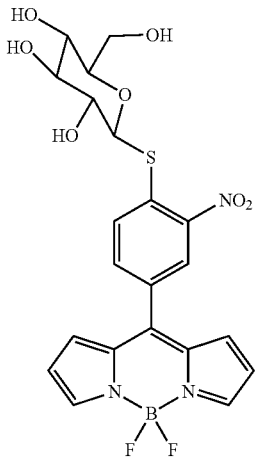

8-[3-Nitro-4-(1'-thio-β-D-glucosyl)phenyl]-4,4-difluoro-4-bora-3a,4a-diaza-s-indacene was prepared according to the general synthetic procedure. 8-(4-Fluoro-3-nitrophenyl)-4,4-difluoro-4-bora-3a,4a-diaza-s-indacene (which was prepared according to the literature: [14]) (100 mg, 0.30 mmol) and 1'-thio-β-D-glucose sodium salt (79 mg, 0.36 mmol) were dissolved in 5 mL of DMF. The mixture was stirred for 15 min. The crude product was purified by column chromatography (silica gel, DCM/MeOH=6/1, v/v) and recrystallization (DCM+a few drops of MeOH/n-hexane) to obtain the product as an orange-red solid (140 mg, 91%).

Mp: >250° C.

$^{1}$H-NMR (500 MHz, DMSO-d$_6$): δ (ppm)=3.19-3.21 (m, 1H, 4'-H), 3.27-3.33 (m, 2H, 2'-H+3'-H), 3.42-3.48 (m, 2H, 5'-H+6'-H), 3.73 (d, J=10.4 Hz, 1H, 6'-H), 4.63 (br s, 1H, OH), 4.98 (d, J=9.3 Hz, 1H, 1'-H), 5.13 (br s, 1H, OH), 5.26 (br s, 1H, OH), 5.67 (br s, 1H, OH), 6.72 (dd, J=4.3, 1.9 Hz, 2H, H$_{pyrrole}$), 7.18 (d, J=4.2 Hz, 2H, H$_{pyrrole}$), 7.92 (dd, J=8.5, 2.0 Hz, 1H, Ar—H$_{ortho}$), 8.01 (d, J=8.5 Hz, 1H, Ar—H$_{meta}$), 8.19 (s, 2H, H$_{pyrrole}$), 8.39 (d, J=2.0 Hz, 1H, Ar—H$_{ortho}$).

$^{13}$C-NMR (126 MHz, DMSO-d$_8$): δ (ppm)=60.9 (6'-C), 69.7 (4'-C), 72.4 (2'-C), 78.2 (3'-C), 81.1 (5'-C), 84.4 (1'-C), 119.7 (C$_{pyrrole}$), 127.5 (Ar—C$_{ortho}$), 129.8 (Ar—C$_{para}$), 128.95 (Ar—C$_{meta}$), 131.8 (C$_{pyrrole}$), 134.1 (C$_{pyrrole}$), 135.3 (Ar—C$_{ortho}$), 138.8*, 143.6*, 145.0 (C$_{pyrrole}$), 145.7 (C$_{meso}$). *These signals could not be assigned exactly to the corresponding carbon atoms. They belong to the Ar—C$_{ipso}$ and the Ar—C$_{nitro}$ of the aryl moiety.

$^{19}$F-NMR (376 MHz, DMSO-d$_6$): δ (ppm)=141.06--141.29 (m$_c$, 2F, BF$_2$).

HRMS (EST-TOF): m/z calcd. for C$_{21}$H$_{20}$BF$_2$N$_3$O$_7$SNa$^+$ [M+Na]$^+$: 530.0975, found: 530.0988.

UV/Vis (MeOH): λ$_{max}$ (nm) [log (ε/L mol$^{-1}$ cm$^{-1}$)]=373 [4.24], 504 [4.68].

1.16 8-[3-Nitro-4-(1'-thio-β-D-galactosyl)phenyl]-4,4-difluoro-4-bora-3a,4a-diaza-s-indacene

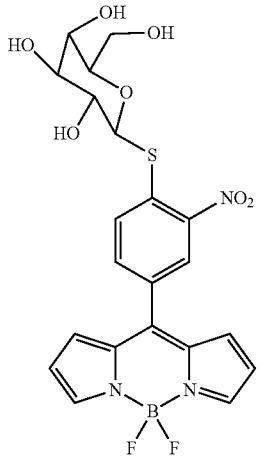

8-[3-Nitro-4-(1'-thio-β-D-galactosyl)phenyl]-4,4-difluoro-4-bora-3a,4a-diaza-s-indacene was prepared according to the general synthetic procedure. 8-(4-Fluoro-3-nitrophenyl)-4,4-difluoro-4-bora-3a,4a-diaza-s-indacene (which was prepared according to the literature: [14]) (100 mg, 0.30 mmol) and 1'-thio-β-D-galactose sodium salt (79 mg, 0.36 mmol) were dissolved in 5 mL of DMF. The mixture was stirred for 15 min. The crude product was purified by column chromatography (silica gel, DCM/MeOH=6/1, v/v) and recrystallization (DCM+a few drops of MeOH/n-hexane) to obtain the product as an orang-red solid (125 mg, 82%).

Mp: 221-225° C.

$^{1}$H-NMR (600 MHz, DMSO-d$_6$): δ (ppm)=3.44-3.46 (m, 1H, 3'-H), 3.54 (d, J=5.9 Hz, 2H, 6'-H), 3.63 (t, J=9.1 Hz, 1H, 2'-H), 3.68 (t, J=6.0 Hz, 1H, 5'-H), 3.78-3.79 (m, 1H, 4'-H), 4.64 (br s, 1H, OH), 4.73 (br s, 1H, OH), 4.92 (d, J=9.7 Hz, 1'-H), 5.04 (br s, 1H, OH), 5.50 (br s, 1H, OH), 6.71-6.72 (m, 2H, H$_{pyrrole}$), 7.17 (d, J=4.2 Hz, 2H, H$_{pyrrole}$), 7.92 (dd, J=8.4, 2.1 Hz, 1H, Ar—H$_{ortho}$), 8.05 (d, J=8.5 Hz, 1H, Ar—H$_{meta}$), 8.17 (s, 2H, H$_{pyrrole}$), 8.38 (d, J=2.1 Hz, 1H, Ar—H$_{ortho}$).

$^{13}$C-NMR (151 MHz, DMSO-d$_6$): δ (ppm)=−60.6 (6'-C), 68.4 (4'-C), 69.0 (2'-C), 74.7 (3'-C), 79.4 (5'-C), 85.0 (1'-C), 119.8 (C$_{pyrrole}$), 127.5 (Ar—C$_{ortho}$), 128.8 (Ar—C$_{para}$), 128.99 (Ar—C$_{meta}$), 131.8 (C$_{pyrrole}$), 134.1 (C$_{pyrrole}$), 135.2 (Ar—C$_{ortho}$), 139.1, 143.6*, 145.5 (C$_{pyrrole}$), 145.8 (C$_{meso}$). *These signals could not be assigned exactly to the corresponding carbon atoms. They belong to the Ar—C$_{ipso}$ and the Ar—C$_{nitro}$ of the aryl moiety.

$^{19}$F-NMR (376 MHz, DMSO-d$_6$): δ (ppm)=−141.12--141.35 (m$_c$, 2F, BF$_2$).

HRMS (ESI-TOF): m/z calcd. for C$_{21}$H$_{20}$BF$_2$N$_3$O$_7$SNa$^+$ [M+Na]$^+$: 530.0975, found: 530.0985, m/z calcd. for C$_{21}$H$_{20}$BF$_2$N$_3$O$_7$SK$^+$ [M+K]$^+$: 546.0715, found: 546.0712.

UV/Vis (MeOH): λ$_{max}$ (nm) [log (ε/L mol$^{-1}$ cm$^{-1}$)]=371 [4.14], 503 [4.57].

1.17 8-[2,3,5,6-Tetrafluoro-4-(1'-thio-β-D-glucosyl)phenyl]-4,4-difluoro-4-bora-3a,4a-diaza-s-indacene

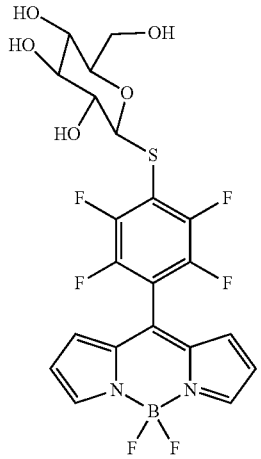

8-[2,3,5,6-Tetrafluoro-4-(1'-thio-β-D-glucosyl)phenyl]-4,4-difluoro-4-bora-3a,4a-diaza-s-indacene was prepared according to the general synthetic procedure. 8-pentafluorophenyl-4,4-difluoro-4-bora-3a,4a-diaza-s-indacene (which was prepared according to the literature: [7]) (100 mg, 0.28 mmol) and 1'-thio-β-D-glucose sodium salt (73 mg, 0.34 mmol) were dissolved in 5 mL of DMF. The mixture was stirred for 15 min. The crude product was purified by column chromatography (silica gel, DCM/MeOH 8/1, v/v) and recrystallization (DCM+a few drops of MeOH/n-hexane) to obtain the product as an orange-red solid (130 mg, 88%).

Mp: 100-109° C.

$^1$H NMR (500 MHz, THF-$d_6$): δ (ppm)=3.21-3.26 (m, 2H, 2'-H+5'-H), 3.27-3.30 (m, 2H, 3'-H+4-H), 3.46-3.51 (m, 1H, 6'-H), 3.72-3.75 (m, 1H, 6'-H), 4.43 (s, 1H, OH) 4.82 ((s, 1H, OH), 4.93 (d, J=9.0 Hz, 1H, 1'-H), 6.60-6.61 (m, 2H, H$_{pyrrole}$), 7.05 (s, 2H, H$_{pyrrole}$), 8.04 (s, 2H, H$_{pyrrole}$).

$^{13}$C NMR (126 MHz, THF-$d_6$): δ (ppm)=63.2 (6'-C), 71.8 (2'-C), 76.1 (4'-C), 80.1 (3'-C), 82.8 (5'-C), 85.8 (1'-C), 120.5 (C$_{pyrrole}$), 131.8 (C$_{pyrrole}$), 136.0 (C$_{pyrrole}$), 147.8 (C$_{pyrrole}$).

$^{19}$F NMR (376 MHz, CDCl$_3$): δ (ppm)=−133.29 (dd, J=23.5, 10.6 Hz, 2F, CF$_{ortho}$), −140.54-−140.63 (m, 2F, CF$_{meta}$), −145.33-−145.56 (m$_c$, 2F, BF$_2$).

HRMS (ESI-TOF): m/z calcd. for C$_{21}$H$_{17}$BF$_5$N$_2$O$_5$S$^+$ [M−F]$^+$: 515.0866, found: 515.0844, m/z calcd. for C$_{21}$H$_{17}$BF$_6$BF$_6$N$_2$O$_5$SNa$^+$ [M+Na]$^+$: 557.0748, found: 557.0729.

UV/Vis (MeOH): λ$_{max}$ (nm) [log (ε/L mol$^{-1}$ cm$^{-1}$)]=356 [3.84], 513 [4.58].

1.18 8-[2,3,5,6-Tetrafluoro-4-(1'-thio-β-D-galactosyl)phenyl]-4,4-difluoro-4-bora-3a,4a-diaza-s-indacene

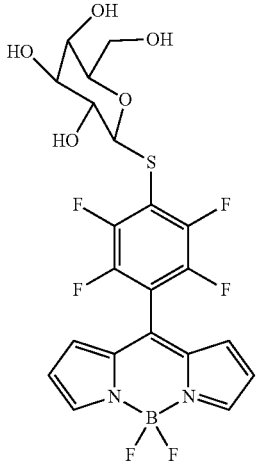

8-[2,3,5,6-Tetrafluoro-4-(1'-thio-β-D-galactosyl)phenyl]-4,4-difluoro-4-bora-3a,4a-diaza-s-indacene was prepared according to the general synthetic procedure. 8-pentafluorophenyl-4,4-difluoro-4-bora-3a,4a-diaza-s-indacene (which was prepared according to the literature: [7]) (100 mg, 0.28 mmol) and 1'-thio-β-D-galactose sodium salt (73 mg, 0.34 mmol) were dissolved in 5 mL of DMF. The mixture was stirred for 15 min. The crude product was purified by column chromatography (silica gel, DCM/MeOH=8/1, v/v) and recrystallization (DCM+a few drops of MeOH/n-hexane) to obtain the product as an orange-red solid (91 mg, 61%).

Mp: 110-115° C.

$^1$H NMR (600 MHz THF-$d_6$): δ (ppm)=3.39 (dd, J=8.7, 4.1 Hz, K, 3'-H), 3.45 (dd, J=5.9, 5.6 Hz, 1H, 5'-H), 3.60-3.63 (m, 3H, 4'-H+6'-H), 3.73 (br s, 1H, OH), 3.82 (br s, 1H, 2'-H), 3.99 (br s, 1H, OH), 4.43 (br s, 1H, OH), 4.86 (dd, J=9.5, 4.8 Hz, 2H, 1'-H+OH), 6.60 (s, 2H, H$_{pyrrole}$), 7.04 (s, 2H, H$_{pyrrole}$), 8.04 (s, 2H, H$_{pyrrole}$).

$^{13}$C NMR (151 MHz, THF-$d_6$): δ (ppm)=62.0 (6'-C), 69.9 (2'-C), 72.9 (4'-C), 76.2 (3'-C), 81.1 (5'-C), 86.1 (1'-C), 112.86 (t, J$_{C−F}$=18.7 Hz, Ar—C$_{ipso}$), 116.61 (t, J$_{C−F}$=203 Hz, Ar—C$_{para}$), 120.2 (C$_{pyrrole}$), 131.0 (C$_{meso}$), 131.4 (C$_{pyrrole}$), 135.6 (C$_{pyrrole}$), 144.73 (ddt, J$_{C−F}$=250.2, 15.8, 4.5 Hz, Ar—C$_{meta}$), 147.4 (C$_{pyrrole}$), 147.95 (ddt, J$_{C−F}$=245.5, 13.1, 4.5 Hz, Ar—C$_{ortho}$).

$^{19}$F NMR (376 MHz, CDCl$_3$): δ (ppm)=−133.09 (dd, J=24.7, 10.6 Hz, 2F, CF$_{ortho}$), −140.54-−140.74 (m, 2F, CF$_{meta}$), −145.40-−145.62 (m$_c$, 2F, BF$_2$).

HRMS (ESI-TOF): m/z calcd. for C$_{21}$H$_{17}$BF$_5$N$_2$O$_5$S$^+$ [M−F]$^+$: 515.0866. found: 515.0856, m/z calcd. for C$_2$H$_{17}$BF$_6$N$_2$O$_5$Na$^+$ [M+Na]$^+$: 557.0748, found: 557.0749, m/z calcd. for C$_{42}$H$_{34}$B$_2$F$_{12}$N$_4$O$_{10}$S$_2$Na$^+$ [2M+Na]$^+$: 1091.1603, found: 1091.1615.

UV/Vis (MeOH): λ$_{max}$ (nm) [log (ε/L mol$^{-1}$ cm$^{-1}$)]=352 [3.69], 513 [4.45].

1.19 8-(4-Butyloxy-2,3,5,6-tetrafluorophenyl)]-4,4-difluoro-4-bora-3a,4a-diaza-s-indacene

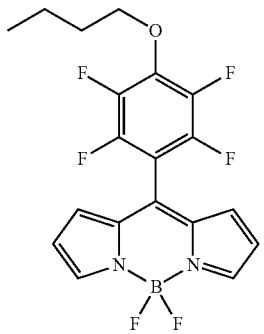

5-(Butyloxy-2,3,5,6-tetrafluorophenyl)dipyrromethane (which was prepared according to the literature: [7])(843 mg, 2.33 mmol) was dissolved in 40 mL DCM. 2,3-dichloro-5,6-dicyano-1,4-benzoquinone (534 mg, 2.33 mmol, suspended in 5 mL DCM) was added and the reaction mixture was stirred for 5 min at rt. After the indicated time, N,N-diisopropylethylamine (3.60 ml, 21.17 mmol) was added and stirred for 15 min. Afterwards, $BF_3 \cdot OEt_2$ (2.80 ml, 21.17 mmol) was added and the reaction mixture was stirred for additional 20 min to 1 h at rt. Water was added to the mixture and extracted with DCM several times. The combined organic phases were washed again with water. The organic layer was dried with $Na_2SO_4$, filtrated, and evaporated to dryness. The crude product was purified by column chromatography (silica gel, DCM/n-hexane=1/1, v/v) to obtain the product as a dark reddish-green solid (203 mg, 11%).

$^1$H NMR (500 MHz, $CDCl_3$): δ (ppm)=1.01 (t, J=7.4 Hz, 3H, Me), 1.52-1.58 (m, 2H, $CH_2$), 1.80-1.86 (m, 2H, $CH_2$), 4.38 (t, J=6.5 Hz, 2H, $CH_2$), 6.55 (d, J=4.0 Hz, 2H, $H_{pyrrole}$), 6.85 (d, J=4.0 Hz, 2H, $H_{pyrrole}$), 7.95 (s, $2H_{pyrrole}$).

$^{13}$C NMR (500 MHz, $CDCl_3$): δ (ppm)=−13.8 (Me), 18.9 ($CH_2$), 32.1 ($CH_2$), 75.4 ($CH_2$), 105.64 (t, $J_{C-F}$=18.1 Hz, Ar—$C_{ipso}$), 119.6 ($C_{pyrrole}$), 130.8 ($C_{pyrrole}$), 131.1 (Ar—$C_{para}$), 135.3 ($C_{pyrrole}$), 141.14 (dd, $J_{C-F}$=249.4, 19.1 Hz, Ar—$C_{meta}$), 144.73 (dd, $J_{C-F}$=251.2, 19.4 Hz, Ar—$C_{ortho}$), 146.2 ($C_{pyrrole}$).

$^{19}$F NMR (376 MHz, $CDCl_3$): δ (ppm)=−138.19 (d, J=16.4 Hz, 2F, Ar—$CF_{meta}$), −144.66−−144.89 (m, 2F, $BF_2$) −153.63 (d, J=23.4 Hz, 2F, Ar—$CF_{ortho}$).

HRMS (ESI-TOF): m/z calcd. for $C_{19}H_{15}BF_6N_2ONa^+$ [M+Na]$^+$: 435.1074, found: 435.1107, m/z calcd. for $C_{38}H_{30}BF_{12}N_4O_2Na^+$ [2M+Na]$^+$: 8472255, found: 847.2309.

UV/Vis (DCM): $\lambda_{max}$ (nm) [log (ε/L mol$^{-1}$ cm$^{-1}$)]=348 [4.03], 517 [4.73].

Example 2

Preparation of Bromo-Substituted Boron Dipyrromethenes

General procedure for the halogenation of 1,3,5,7-tetramethyl BODIPYs: The BODIPY was dissolved in 1,1,1,3,3,3-hexafluoroisopropanol (HFIP) and N-bromosuccinimide (NBS) was added. The mixture was stirred for the indicated time at room temperature. Afterwards, the reaction mixture was diluted with EtOAc and washed with water several times. The organic layer was dried with $Na_2SO_4$, filtered, and evaporated to dryness. The crude product was purified by column chromatography.

2.1 2,6-Dibromo-8-(4-fluoro-3-nitrophenyl)-1,3,5,7-tetramethyl-4,4-difluoro-4-bora-3a, 4a-diaza-s-indacene

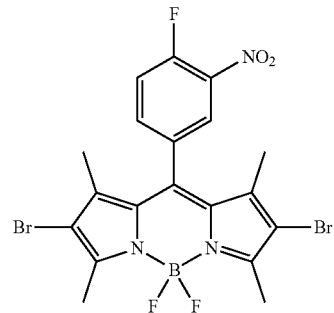

2,6-Dibromo-8-(4-fluoro-3-nitrophenyl)-1,3,5,7-tetramethyl-4,4-difluoro-4-bora-3a, 4a-diaza-s-indacene was prepared according to the general synthetic procedure. 8-(4-fluoro-3-nitrophenyl)-1,3,5,7-tetramethyl-4,4-difluoro-4-bora-3a, 4a-diaza-s-indacene (60 mg, 0.16 mmol) and NBS (66 mg, 037 mmol) were dissolved in 2 mL of HFIP. The mixture was stirred for 1 min. The crude product was purified by column chromatography (silica gel, EtOAc/n-hexane=1/4, v/v) to obtain the product as a reddish-green solid (48 mg, 57%).

Mp: >250° C.

$^1$H NMR (500 MHz, THF-$d_8$): δ (ppm)=1.48 (s, 6H, Me), 2.58 (s, 6H, Me), 7.71 (dd, J=10.8, 8.5 Hz, 1H, Ar—$H_{meta}$), 7.81 (ddd, J=8.5, 4.2, 2.2 Hz, 1H, Ar—$H_{ortho}$), 8.30 (dd, J=7.0, 2.3 Hz, 1H, Ar—$H_{ortho}$).

$^{13}$C NMR (126 MHz, THF-$d_8$): δ (ppm)=13.96 (Me), 14.7 (Me), 112.6-122.7 (m, CBr), 120.99 (d, $J_{C-F}$=20.9 Hz, Ar—$C_{meta}$), 127.9 (d, $J_{C-F}$=2.1 Hz, Ar—$C_{ortho}$), 131.4 ($C_{pyrrole}$), 132.2*, 136.9 (d, $J_{C-F}$=9.3 Hz, Ar—$C_{ortho}$), 139.9*, 141.2 ($C_{pyrrole}$), 155.7 ($C_{pyrrole}$), 157.10 (d, $J_{C-F}$=266.0 Hz, Ar—$C_{para}$). *These signals could not be assigned exactly to the corresponding carbon atoms. They belong to the Ar—$C_{ipso}$ and the Ar—$C_{nitro}$ of the aryl moiety.

$^{19}$F NMR (376 MHz, THF-$d_8$): δ (ppm)=−117.54 (s, 1F, CF), −146.26−−146.51 ($m_c$, 2F, $BF_2$).

UV/Vis (DCM): $\lambda_{max}$ (nm) [log (ε/L mol$^{-1}$ cm$^{-1}$)]= 53814.661.

2.2 2,6-Dibromo-8-pentafluorophenyl-1,3,5,7-tetramethyl-4,4-difluoro-4-bora-3a, 4a-diaza-s-indacene

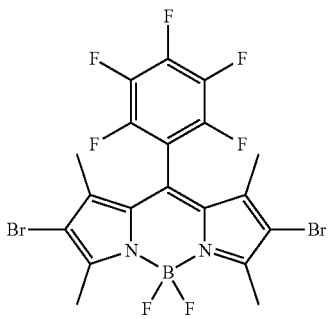

2,6-Dibromo-8-pentafluorophenyl-1,3,5,7-tetramethyl-4,4-difluoro-4-bora-3a, 4a-diaza-s-indacene was prepared according to the general synthetic procedure. 8-Pentafluorophenyl-1,3,5,7-tetramethyl-4,4-difluoro-4-bora-3a,4a-diaza-s-indacene (which was prepared according to the literature: [8]) (100 mg, 0.24 mmol) and NBS (107 mg, 0.60 mmol) were dissolved in 2 mL of HFIP. The mixture was stirred for 1 min. The crude product was purified by column chromatography (silica gel, EtOAc/n-hexane=1/9, v/v) to obtain the product as an orange-red solid (85 mg, 62%).

Mp: >250° C. ° C.

$^1$H NMR (500 MHz, CDCl$_3$): δ (ppm)=1.62 (s, 6H, Me), 2.63 (s, 6H, Me).

$^{13}$C NMR (126 MHz, CDCl$_3$): δ (ppm)=13.1 (Me), 14.1 (Me), 113.2 (CBr), 114.0 (Ar—C$_{ipso}$), 121.2 (C$_{meso}$), 130.2 (C$_{pyrrole}$), 139.1 (C$_{pyrrole}$), 156.6 (C$_{pyrrole}$).

$^{19}$F NMR (376 MHz, CDCl$_3$): δ (ppm)=−138.79--−138.87 (m, 2F, CF$_{meta}$), −145.62--−145.87 (m, 2F, BF$_2$), −148.83 (t, J=20.8 Hz, 1F, CF$_{para}$), −158.36--−158.49 (m, 2F, CF$_{meta}$).

HRMS (ESI-TOF): m/z calcd. for C$_{19}$H$_{11}$BF$_7$N$_2^+$ [M−H]$^+$: 570.9255, found: 570.9248.

UV/Vis (DCM): λ$_{max}$ (nm) [log (ε/L mol$^{-1}$ cm$^{-1}$)]=551 [4.79].

2.3 2,6-Dibromo-8-[4-(N-butylamino)-3-nitrophenyl]-1,3,5,7-tetramethyl-4,4-difluoro-4-bora-3a,4a-diaza-s-indacene

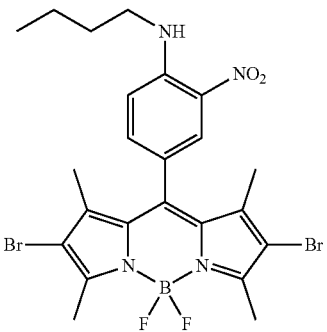

2,6-Dibromo-8-[4-(N-butylamino)-3-nitrophenyl]-1,3,5,7-tetramethyl-4,4-difluoro-4-bora-3a,4a-diaza-s-indacene was prepared according to the general synthetic procedure. 8-[4-(N-Butylamino)-3-nitrophenyl]-1,3,5,7-tetramethyl-4,4-difluoro-4-bora-3a,4a-diaza-s-indacene (95 mg, 0.22 mmol) and NBS (96 mg, 0.54 mmol) were dissolved in 2 mL of HFIP. The mixture was stirred for 1 min. The crude product was purified by column chromatography (silica gel, EtOAc/n-hexane=1/9, v/v) to obtain the product as a red solid (81 mg, 63%).

Mp: 191-194° C.

$^1$H NMR (500 MHz, THF-d$_8$): δ (ppm)=1.02 (t, J=7.4 Hz, 3H, Me$_{butyl}$), 1.49-1.55 (m, 2H, CH$_2$), 1.59 (s, 6H, Me), 1.75-1.79 (m, 2H, CH$_2$), 2.56 (s, 6H, Me), 3.45 (td, J=7.3, 5.4 Hz, 1H, CH$_2$), 7.27 (d, J=8.8 Hz, 1H, Ar—H$_{meta}$), 7.43 (dd, J=8.7, 2.1 Hz, 1H, Ar—H$_{ortho}$), 8.18 (d, J=2.2 Hz, 1H, Ar—H$_{ortho}$), 8.26 (t, J=5.5 Hz, 1H, NH).

$^{13}$C NMR (126 MHz, THF-d$_8$): δ (ppm)=13.9 (Me), 14.3 (Me), 14.9 (Me$_{butyl}$), 21.3 (CH$_2$), 32.1 (CH$_2$), 43.8 (CH$_2$), 112.3 (CBr), 116.5 (Ar—C$_{meta}$) 121.1 (C$_{meso}$), 127.9 (Ar—C$_{ortho}$), 132.0 (C$_{pyrrole}$), 133.2*, 136.6 (Ar—C$_{ortho}$), 141.1 (C$_{pyrrole}$), 146.9 (Ar—C$_{para}$), 154.9 (C$_{pyrrole}$). *These signals could not be assigned exactly to the corresponding carbon atoms. They belong to the Ar—C$_{ipso}$ and the Ar—C$_{nitro}$ of the aryl moiety.

$^{19}$F NMR (376 MHz, THF-d$_8$): δ (ppm)=−145.98--−146.84 (m$_c$, 2F, BF$_2$).

HRMS (ESI-TOF): m/z calcd. for C$_{23}$H$_{25}$BBr$_2$F$_2$N$_4$O$_2$Na$^+$ [M+Na]$^+$: 621.0277, found: 621.0314, m/z calcd. for C$_{46}$H$_{50}$B$_2$Br$_4$F$_4$N$_8$O$_4$Na$^+$ [2M+Na]$^+$: 1219.0662, found: 1219.0712.

UV/Vis (DCM): λ$_{max}$ (nm) [log (ε/L mol$^{-1}$ cm$^{-1}$)]=397 [4.19], 533 [4.87].

2.4 2,6-Dibromo-8-[4-(N-2-hydroxyethylamino)-3-nitrophenyl]-1,3,5,7-tetramethyl-4,4-difluoro-4-bora-3a,4a-diaza-s-indacene

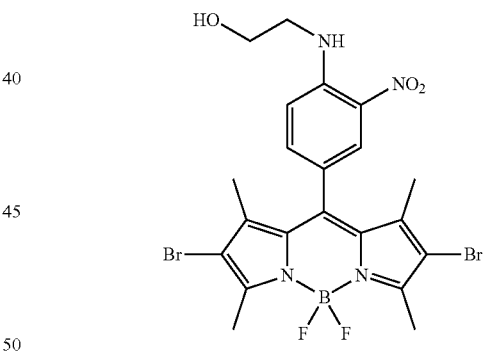

2,6-Dibromo-8-[4-N-2-hydroxyethylamino)-3-nitrophenyl]-1,3,5,7-tetramethyl-4,4-difluoro-4-bora-3a,4a-diaza-s-indacene was prepared according to the general synthetic procedure. 8-[4-(N-2-Hydroxyethylamino)-3-nitrophenyl]-1,3,5,7-tetramethyl-4,4-difluoro-4-bora-3a,4a-diaza-s-indacene (90 mg, 0.21 mmol) and NBS (94 mg, 0.53 mmol) were dissolved in 2 mL of HFIP. The mixture was stirred for 1 min. The crude product was purified by column chromatography (silica gel, EtOAc/n-hexane=4/1, v/v) to obtain the product as a red solid (39 mg, 32%).

Mp: >250° C.

$^1$H NMR (500 MHz, THF-d$_8$): δ (ppm)=1.59 (s, 6H, Me), 2.56 (s, 6H, Me), 3.52 (t, J=5.4 Hz, 2H, CH$_2$), 3.82 (t, J=5.4 Hz, 2H, CH$_2$), 7.30 (d, J=8.8 Hz, 1H, Ar—H$_{meta}$), 7.42 (dd, J=8.8, 2.2 Hz, 1H, Ar—H$_{ortho}$), 8.17 (d, J=2.1 Hz, 1H, Ar—H$_{ortho}$).

$^{13}$C NMR (126 MHz, THF-d$_8$): δ (ppm)=13.9 (Me), 14.9 (Me), 46.2 (CH$_2$), 60.7 (CH$_2$), 112.2 (CBr), 116.7 (Ar—C$_{meta}$), 121.2*, 127.8 (Ar—C$_{ortho}$), 132.0 (C$_{pyrrole}$), 133.3*, 136.5 (Ar—C$_{ortho}$), 141.1 (C$_{pyrrole}$), 142.1 (Ar—C$_{para}$), 154.8 (C$_{pyrrole}$). *These signals could not be assigned exactly to the corresponding carbon atoms. They belong to the Ar—C$_{ipso}$ and the Ar—C$_{nitro}$ of the aryl moiety.

$^{19}$F NMR (376 MHz, THF-d$_8$): δ (ppm)=−146.26-− 146.57 (m, 2F, BF$_2$).

HRMS (ESI-TOF): m/z calcd, for C$_{21}$H$_{21}$BBr$_2$F$_2$N$_4$O$_3$Na$^+$ [M+Na]$^+$: 608.9913, found: 608.9924, m/z calcd. for C$_{21}$H$_{21}$BBr$_2$F$_2$N$_4$O$_3$K$^+$ [M+K]$^+$: 624.9653. found: 624.9670, m/z calcd. for C$_{42}$H$_{42}$B$_2$Br$_4$F$_4$N$_8$O$_6$K$^+$ [2M+K]$^+$: 1210.9674, found: 1210.9682.

UV/Vis (MeOH): λ$_{max}$ (nm) [log (ε/L mol$^{-1}$ cm$^{-1}$)]=401 [3.76], 528 [4.36].

2.5 2,6-Dibromo-8-[3-nitro-4-(N-2-prop-2-enylamino)phenyl]-1,3,5,7-tetramethyl-4,4-difluoro-4-bora-3a,4a-diaza-s-indacene

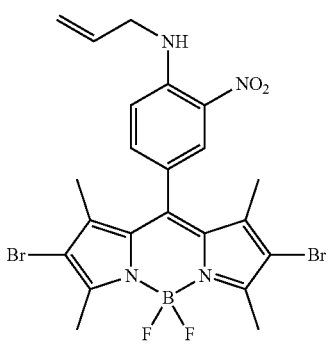

2,6-Dibromo-8-[3-nitro-4-(N-2-prop-2-enylamino)phenyl]-1,3,5,7-tetramethyl-4,4-difluoro-4-bora-3a,4a-diaza-s-indacene was prepared according to the general synthetic procedure. 8-[3-Nitro-4-(N-2-prop-2-enylamino)phenyl]-1,3,5,7-tetramethyl-4,4-difluoro-4-bora-3a,4a-diaza-s-indacene (87 mg, 0.21 mmol) and NBS (91 mg, 0.51 mmol) were dissolved in 2 mL of HFIP. The mixture was stirred for 1 min. The crude product was purified by column chromatography (silica gel, EtOAc/n-hexane=1/9, v/v) to obtain the product as a red solid (53 mg, 44%).

Mp: 209-214° C.

$^1$H NMR (500 MHz, THF-d$_8$): δ (ppm)=1.58 (m, 6H, Me), 2.56 (s, 6H, Me), 4.12-4.15 (m, 2H, CH$_2$), 5.23 (ddd, J=10.4, 1.5 Hz, 1H, H$_2$C=CH—), 5.31 (ddd, J=17.2, 1.6 Hz, 1H, H$_2$C=CH—), 6.01 (ddt, J=17.2, 10.1, 4.9 Hz, 1H, H$_2$C=CH—), 7.20 (d, J=8.8 Hz, 1H, Ar—H$_{meta}$), 7.41 (dd, J=8.8, 2.1 Hz, 1H, Ar—H$_{ortho}$), 8.19 (d, J=2.2 Hz, 1H, Ar—H$_{ortho}$), 8.45 (t, J=5.9 Hz, 1H, NH).

$^{13}$C NMR (126 MHz, THF-d$_8$): δ (ppm)=13.9 (Me), 14.8 (Me), 46.1 (CH$_2$), 112.3 (CBr), 116.9 (H$_2$C=CH—), 117.0 (Ar—C$_{meta}$), 121.5*, 127.7 (Ar—C$_{ortho}$), 131.99 (C$_{pyrrole}$), 133.5*, 134.9 (H$_2$C=CH—), 136.4 (Ar—C$_{ortho}$), 141.1 (C$_{pyrrole}$), 142.1 (C$_{meso}$), 146.8 (Ar—C$_{para}$), 154.9 (C$_{pyrrole}$), *These signals could not be assigned exactly to the corresponding carbon atoms. They belong to the Ar—C$_{ipso}$ and the Ar—C$_{nitro}$ of the aryl moiety.

$^{19}$F NMR (376 MHz, THF-d$_8$): δ (ppm)=−146.27-− 146.56 (m$_c$, 2F, BF$_2$).

HRMS (ESI-TOF): m/z calcd. for C$_{22}$H$_{21}$BBr$_2$FN$_4$O$_2$$^+$ [M−F]$^+$: 563.0082, found: 563.0083, m/z calcd. for C$_{22}$H$_{21}$BBr$_2$F$_2$N$_4$O$_2$Na$^+$ [M+Na]$^+$: 604.9964, found: 604.9968, m/z calcd. for C$_{22}$H$_{21}$BBr$_2$F$_2$N$_4$O$_2$K$^+$ [M+K]$^+$: 620.9703, found: 620.9707, m/z calcd. for C$_{44}$H$_{24}$B$_2$Br$_4$F$_4$N$_8$O$_4$Na$^+$ [2M+Na]$^+$: 1187.0036, found: 1187.0044.

UV/Vis (DCM): λ$_{max}$ (nm) [log (ε/L mol$^{-1}$ cm$^{-1}$)]=399 [4.17], 528 [4.85].

2.6 2,6-Dibromo-8-[3-nitro-4-(N-2-prop-2-ynylamino)phenyl]-1,3,5,7-tetramethyl-4,4-difluoro-4-bora-3a,4a-diaza-s-indacene

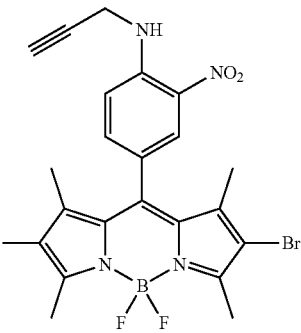

2,6-Dibromo-8-[3-nitro-4-(N-2-prop-2-ynylamino)phenyl]-1,3,5,7-tetramethyl-4,4-difluoro-4-bora-3a,4a-diaza-s-indacene was prepared according to the general synthetic procedure. 8-[3-Nitro-4-(N-2-prop-2-ynylamino)phenyl]-1,3,5,7-tetramethyl-4,4-difluoro-4-bora-3a,4a-diaza-s-indacene (90 mg, 021 mmol) and NBS (95 mg, 0.53 mmol) were dissolved in 2 mL of HFIP. The mixture was stirred for 1 min. The crude product was purified by column chromatography (silica gel, EtOAc/n-hexane=1/9, v/v) to obtain the product as a red solid (35 mg, 28%).

Mp: 229-235° C.

$^1$H NMR (500 MHz, THF-d$_8$): δ (ppm)=1.57 (m, 6H, Me), 2.56 (s, 6H, Me), 2.76 (t, J=2.4 Hz, 1H, CH), 4.30 (dd, J=5.9, 2.5 Hz, 2H, CH$_2$), 7.36 (d, J=8.8 Hz, 1H, Ar—H$_{meta}$), 7.50 (dd, J=8.8, 2.1 Hz, 1H, Ar—H$_{ortho}$), 8.21 (d, J=2.2 Hz, 1H, Ar—H$_{ortho}$), 8.43 (t, J=5.9 Hz 1H, NH).

$^{13}$C NMR (126 MHz, THF-d$_8$): δ (ppm)=13.99 (Me), 14.8 (Me), 33.2 (CH$_2$), 73.5 (CH), 80.2 (C), 112.4 (CBr), 117.1 (Ar—C$_{meta}$), 122.5*, 127.7 (Ar—C$_{ortho}$), 131.98 (C$_{pyrrole}$), 134.1*, 136.4 (Ar—C$_{ortho}$), 141.2 (C$_{pyrrole}$), 141.9 (C$_{meso}$), 145.9 (Ar—C$_{para}$), 154.95 (C$_{pyrrole}$). *These signals could not be assigned exactly to the corresponding carbon atoms. They belong to the Ar—C$_{ipso}$ and the Ar—C$_{nitro}$ of the aryl moiety.

$^{19}$F NMR (376 MHz, THF-d$_8$): δ (ppm)=−146.27-− 146.56 (m$_c$, 2F, BF$_2$).

HRMS (ESI-TOF): m/z calcd. for C$_{22}$H$_{19}$BBr$_2$FN$_4$O$_2$$^+$ [M−F]$^+$: 560.9926, found: 560.9975, m/z calcd. for C$_{22}$H$_{19}$BBr$_2$F$_2$N$_4$O$_2$Na$^+$ [M+Na]$^+$: 602.9808, found: 602.9862, m/z calcd. for C$_{22}$H$_{19}$BBr$_2$F$_2$N$_4$O$_2$K$^+$ [M−K]$^+$: 618.9547, found: 618.9608, m/z calcd. for C$_{44}$H$_{38}$B$_2$Br$_4$F$_4$N$_8$O$_4$Na$^+$ [2M+Na]$^+$: 1182.9723, found: 1182.9824.

UV/Vis (DCM): λ$_{max}$ (nm) [log (ε/L mol$^{-1}$ cm$^{-1}$)]=397 [4.25], 533 [4.87].

2.7 2,6-Dibromo-8-[4-(N-6-methoxy-6-oxohexylamino)-3-nitrophenyl]-1,3,5,7-tetramethyl-4,4-difluoro-4-bora-3a,4a-diaza-s-indacene

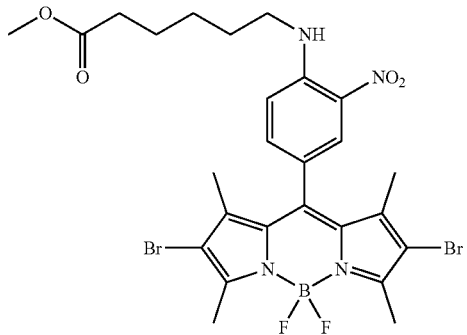

2,6-Dibromo-3-[4-(N-6-methoxy-6-oxohexylamino)-3-nitrophenyl]-1,3,5,7-tetramethyl-4,4-difluoro-4-bora-3a,4a-diaza-s-indacen was prepared according to the general synthetic procedure. 8-[4-(N-6-Methoxy-6-oxohexylamino)-3-nitrophenyl]-1,3,5,7-tetramethyl-4,4-difluoro-4-bora-3a,4a-diaza-s-indacen (95 mg, 0.19 mmol) and NBS (83 mg, 0.46 mmol) were dissolved in 2 mL of HFIP. The mixture was stirred for 1 min. The crude product was purified by column chromatography (silica gel, EtOAc/n-hexane=1/9, v/v) to obtain the product as a red solid (67 mg, 54%).

Mp: 152-155° C.

$^1$H NMR (500 MHz, THF-d$_8$): δ (ppm)=1.48-1.54 (m, 2H, CH$_2$), 1.59 (s, 6H, Me), 1.67-1.71 (m, 2H, CH$_2$), 1.76-1.82 (m, 2H, CH), 2.33 (t, J=7.3 Hz, 2H, CH$_2$), 2.56 (s, 6H, Me), 3.46 (td, J=7.3, 5.6 Hz, 2H, CH$_2$), 3.60 (s, 3H, Me$_{OMe}$), 7.27 (d, J=8.8 Hz, 1H, Ar—H$_{meta}$), 7.43 (dd, J=8.8, 2.2 Hz, 1H, Ar—H$_{ortho}$), 8.18 (d, J=2.1 Hz, 1H, Ar—H$_{ortho}$), 3.27 (t, J=5.5 Hz, 1H, NH).

$^{13}$C NMR (126 MHz, THF-d$_8$): δ (ppm)=13.9 (Me), 14.9 (Me), 25.98 (CH$_2$), 27.6 (CH$_2$), 29.4 (CH$_2$), 34.3 (CH$_2$), 43.9 (CH$_2$), 51.5 (Me$_{OMe}$), 112.6 (CBr), 116.5 (Ar—C$_{meta}$), 121.2*, 127.9 (Ar—C$_{ortho}$), 132.0 (C$_{pyrrole}$), 1332*, 136.6 (Ar—C$_{ortho}$), 141.1 (C$_{pyrrole}$), 142.1 (C$_{meso}$), 146.9 (Ar—C$_{para}$), 154.9 (C$_{pyrrole}$), 173.8 (CO). *These signals could not be assigned exactly to the corresponding carbon atoms. They belong to the Ar—C$_{ipso}$, and the Ar—C$_{nitro}$ of the aryl moiety.

$^{19}$F NMR (376 MHz, THF-d$_8$): δ (ppm)=−146.25--−146.56 (m$_c$, 2F, BF$_2$).

HRMS (ESI-TOF): m/z calcd. for C$_{26}$H$_{29}$BBr$_2$F$_2$N$_4$O$_4$Na$^+$ [M+Na]$^+$: 693.0488, found: 693.0503, m/z calcd. for C$_{26}$H$_{29}$BBr$_2$F$_2$N$_4$O$_4$K$^+$ [M+K]$^+$: 709.0228, found: 709.0235, m/z calcd. for C$_{52}$H$_{58}$B$_2$Br$_4$F$_4$N$_8$O$_8$Na$^+$ [2M+Na]$^+$: 1363.1085, found: 1363.1112.

UV/Vis (DCM): λ$_{max}$ (nm) [log (ε/L mol$^{-1}$ cm$^{-1}$)]=404 [4.19], 532 [4.87].

2.8 2,6-Dibromo-8-[44N,N-dibutylamino)-3-nitrophenyl]-1,3,5,7-tetramethyl-4,4-difluoro-4-bora-3a,4a-diaza-s-indacene

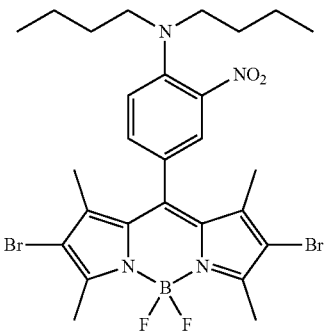

2,6-Dibromo-8-[4-(N,N-butylamino)-3-nitrophenyl]-1,3,5,7-tetramethyl-4,4-difluoro-4-bora-3a,4a-diaza-s-indacene was prepared according to the general synthetic procedure. 8-[4-(N,N-Dibutylamino)-3-nitrophenyl]-1,3,5,7-tetramethyl-4,4-difluoro-4-bora-3a,4a-diaza-s-indacene (90 mg, 0.18 mmol) and NBS (80 mg, 0.45 mmol) were dissolved in 2 mL of HFIP. The mixture was stirred for 1 min. The crude product was purified by column chromatography (silica gel, EtOAc/n-hexane=1/9, v/v) to obtain the product as a red solid (68 mg, 57%).

Mp: 157-159° C.

$^1$H NMR (500 MHz, THF-d$_8$): δ (ppm)=0.89 (t, J=7.3 Hz, 6H, Me$_{butyl}$), 1.28-1.35 (m, 4H, CH$_2$), 1.53-1.59 (m, 10H, Me+CH$_2$), 2.56 (s, 6H, Me), 3.25 (t, J=7.1 Hz, 4H, CH), 7.39 (dd. J=8.7, 2.0 Hz, H, Ar—H$_{meta}$), 7.46 (dd, J=8.7, 1.4 Hz, 1H, Ar—H$_{ortho}$), 7.77 (d, J=2.0 Hz, 1H, Ar—H$_{ortho}$).

$^{13}$C NMR (126 MHz, THF-d$_8$): δ (ppm)=13.99 (Me$_{butyl}$), 14.3 (Me), 14.6 (Me), 21.0 (CH$_2$), 30.6 (CH$_2$), 52.8 (CH$_2$), 112.3-112.4 (m, CBr), 123.7 (Ar—C$_{meta}$), 125.4*, 127.2 (Ar—C$_{ortho}$), 131.8 (C$_{pyrrole}$), 133.2 (Ar—C$_{ortho}$), 141.1 (C$_{pyrrole}$), 141.7 (C$_{meso}$), 143.9, 146.4 (Ar—C$_{para}$), 154.97 (C$_{pyrrole}$). *These signals could not be assigned exactly to the corresponding carbon atoms. They belong to the Ar—C$_{ipso}$ and the Ar—C$_{nitro}$ of the aryl moiety.

$^{19}$F NMR (376 MHz, THF-d$_8$): δ (ppm)=−146.31--−146.52 (m$_c$, 2F, BF$_2$).

HRMS (ESI-TOF): m/z calcd. for C$_{27}$H$_{34}$BBr$_2$F$_2$N$_4$O$_2^+$ [M+H]$^+$: 655.1084, found: 655.1087, m/z calcd. for C$_{27}$H$_{33}$BBr$_2$F$_2$N$_4$O$_2$Na$^+$ [M+Na]$^+$: 677.0903, found: 677.0899, m/z calcd. for C$_{54}$H$_{66}$B$_2$Br$_4$F$_4$N$_2$O$_4$Na$^+$ [2M+Na]$^+$: 1331.1914, found: 1331.1930.

UV/Vis (DCM): λ$_{max}$ (nm) [log (ε/L mol$^{-1}$ cm$^{-1}$)]=389 [4.03], 533 [4.86].

2.9 2,6-Dibromo-8-[4-(N-1-hydroxymethyl-2-hydroxyethylamino)-3-nitrophenyl]-1,3,5,7-tetramethyl-4,4-difluoro-4-bora-3a,4a-diaza-s-indacene

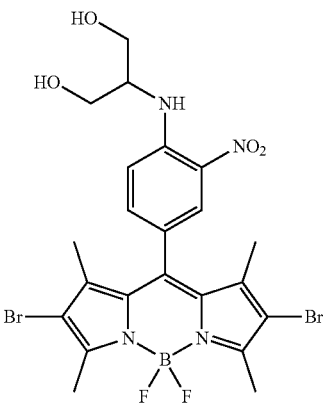

2,6-Dibromo-8-[4-(N-1-hydroxymethyl-2-hydroxyethylamino)-3-nitrophenyl]-1,3,5,7-tetramethyl-4,4-difluoro-4-bora-3a,4a-diaza-s-indacene was prepared according to the general synthetic procedure. 8-[4-(N-1-Hydroxymethyl-2-hydroxyethylamino)-3-nitrophenyl]-1,3,5,7-tetramethyl-4,4-difluoro-4-bora-3a,4a-diaza-s-indacene (94 mg, 0.21 mmol) and NBS (91 mg, 0.51 mmol) were dissolved in 2 mL of HFIP. The mixture was stirred for 1 min. The crude product was purified by column chromatography (silica gel, EtOAc/n-hexane=9/1, v/v) to obtain the product as a red solid (61 mg, 48%).

Mp: >250° C.

$^{1}$H NMR (500 MHz, THF-$d_8$): δ (ppm) 1.61 (s, 6H, Me), 2.56 (s, 6H, Me), 3.73-3.78 (m, 2H, CH$_2$), 3.81-3.84 (m, 3H, CH$_2$+CH), 4.28 (t, J=5.1 Hz, 2H, OH), 7.39-7.40 (m, 2H, Ar—H$_{meta}$+Ar—H$_{ortho}$), 8.17 (dd, J=1.5, 1.0 Hz, 1H, Ar—H$_{ortho}$), 8.65 (d, J=7.8 Hz, 1H, NH).

$^{13}$C NMR (126 MHz, THF-$d_8$): δ (ppm) 13.9 (Me), 14.9 (Me), 56.96 (CH), 61.6 (CH$_2$), 112.2-112.3 (m$_c$, CBr), 117.3 (Ar—C$_{meta}$), 121.0*, 127.9 (Ar—C$_{ortho}$), 132.0 (C$_{pyrrole}$), 133.2*, 136.3 (Ar—C$_{ortho}$), 141.1 (C$_{pyrrole}$), 142.2 (C$_{meso}$), 146.8 (Ar—C$_{para}$), 154.8 (C$_{pyrrole}$). *These signals could not be assigned exactly to the corresponding carbon atoms. They belong to the Ar—C$_{ipso}$ and the Ar—C$_{nitro}$ of the aryl moiety.

$^{19}$F NMR (376 MHz, THF-$d_8$): δ (ppm)=−146.12-−146.72 (m$_c$, 2F, BF$_2$).

HRMS (ESI-TOF): m/z calcd. for C$_{22}$H$_{23}$BBr$_2$FN$_4$O$_4^+$ [M−F]$^+$: 597.0137, found: 597.0165, m/z calcd. for C$_{22}$H$_{23}$BBr$_2$F$_2$N$_4$O$_4$Na$^+$ [M+Na]$^+$: 639.0019, found: 639.0050.

UV/Vis (MeOH): λ$_{max}$ (nm) [log (ε/L mol$^{-1}$ cm$^{-1}$)]=402 [4.03], 528 [4.72].

2.10 2,6-Dibromo-8-[4-(N-butylamino)-2,3,5,6-tetrafluorophenyl]-1,3,5,7-tetramethyl-4,4-difluoro-4-bora-3a,4a-diaza-s-indacene

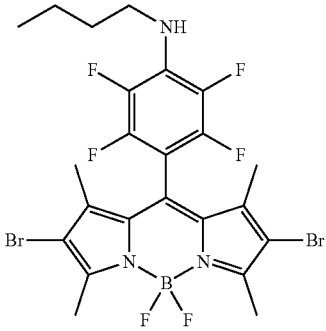

2,6-Dibromo-8-[4-(N-butylamino)-2,3,5,6-tetrafluorophenyl]-1,3,5,7-tetramethyl-4,4-difluoro-4-bora-3a,4a-diaza-s-indacene was prepared according to the general synthetic procedure. 8-[4-(N-Butylamino)-2,3,5,6-tetrafluorophenyl]-1,3,5,7-tetramethyl-4,4-difluoro-4-bora-3a,4a-diaza-s-indacene (which was prepared according to the literature: [8]) (95 mg, 0.20 mmol) and NBS (90 mg, 0.51 mmol) were dissolved in 2 mL of HFIP. The mixture was stirred for 1 min. The crude product was purified by column chromatography (silica gel, EtOAc/n-hexane=1/9, v/v) to obtain the product as a red solid (68 mg, 54%).

Mp: 133-135° C.

$^{1}$H NMR (500 MHz, THF-$d_8$): δ (ppm)=0.96 (t, J=7.4 Hz, 3H, Me$_{butyl}$), 1.39-1.46 (m, 2H, CH$_2$), 1.61-1.67 (m, 2H, CH$_2$), 1.73 (s, 6H, Me), 2.57 (s, 6H, Me), 3.45-3.50 (m, 2H, CH$_2$), 5.83 (s, 1H, NH).

$^{13}$C NMR (126 MHz, THF-$d_8$): δ (ppm)=13.1 (Me), 14.0 (Me), 14.3 (Me$_{butyl}$), 20.9 (CH$_2$), 33.9 (CH$_2$), 45.96 (CH$_2$), 98.61 (t, J$_{C—F}$=19.9 Hz, Ar—C$_{ipso}$), 112.9-112.99 (m, CBr), 127.5 (C$_{meso}$), 131.9 (Ar—C$_{para}$), 132.0 (C$_{pyrrole}$), 138.82 (dd, J$_{C—F}$=241.3, 26.0 Hz, Ar—C$_{meta}$), 140.5 (C$_{pyrrole}$), 145.26 (dd, J$_{C—F}$=242.0, 11.9 Hz, Ar—C$_{ortho}$), 156.2 (C$_{pyrrole}$).

$^{19}$F NMR (376 MHz, CDCl$_3$): δ (ppm)=−145.65 (d, J=17.6 Hz, 2F, CF$_{meta}$), −146.17-−146.42 (m$_c$, 2F, BF$_2$), −161.13 (d, J=17.6 Hz, 2F, CF$_{meta}$).

HRMS (ESI-TOF): m/z calcd. for C$_{23}$H$_{22}$BBr$_2$F$_6$N$_3$Na$^+$ [M+Na]$^+$: 648.0049, found: 648.0058, m/z calcd. for C$_{46}$H$_{44}$B$_2$Br$_4$F$_{12}$N$_6$Na$^+$ [2M+Na]$^+$: 1237.0207, found: 1237.0221.

UV/Vis (DCM): λ$_{max}$ (nm) [log (ε/L mol$^{-1}$ cm$^{-1}$)]=391 [4.12], 545 [4.93].

2.11 2,6-Dibromo-8-[4-(N-prop-2-ynylamino)-2,3,5,6-tetrafluorophenyl]-1,3,5,7-tetramethyl-4,4-difluoro-4-bora-3a,4a-diaza-s-indacene

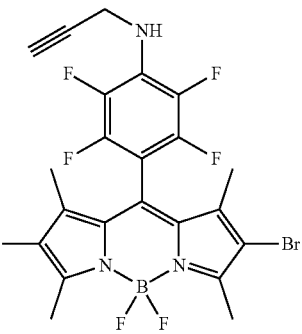

2,6-Dibromo-8-[4-(N-prop-2-ynylamino)-2,3,5,6-tetrafluorophenyl]-1,3,5,7-tetramethyl-4,4-difluoro-4-bora-3a,4a-diaza-s-indacene was prepared according to the general synthetic procedure. 8-[4-(N-Prop-2-ynylamino)-2,3,5,6-tetrafluorophenyl]-1,3,5,7-tetramethyl-4,4-difluoro-4-bora-3a,4a-diaza-s-indacene (87 mg, 0.19 mmol) and NBS (86 mg, 0.48 mmol) were dissolved in 2 mL of HFIP. The mixture was stirred for 1 min. The crude product was purified by column chromatography (silica gel, EtOAc/n-hexane=1/9, v/v) to obtain the product as a green solid (54 mg, 44%).

Mp: 184-188° C.

$^1$H NMR (500 MHz, THF-$d_8$): δ (ppm) 1.72 (s, 6H, Me), 2.58 (s, 6H, Me), 2.72 (t, J=2.4 Hz, 1H, CH), 4.19-4.21 (m, 2H, $CH_2$), 6.20-6.23 (s, 1H, NH).

$^{13}$C NMR (126 MHz, THF-$d_8$): δ (ppm)=13.1 (Me), 14.1 (Me), 35.6 ($CH_3$), 73.5 (C), 81.0 (CH), 101.20 (t, $J_{C-F}$=18.7 Hz, Ar—$C_{ipso}$), 113.0-113.1 (m, CBr), 127.1 ($C_{meso}$), 130.8-131.0 (m, Ar—$C_{para}$), 131.8 ($C_{pyrrole}$), 139.85 (ddd, $J_{C-F}$=242.5, 15.8, 10.5 Hz, Ar—$C_{meta}$), 140.5 ($C_{pyrrole}$), 145.03 (dd, $J_{C-F}$=244.1, 16.7 Hz, Ar—$C_{ortho}$), 156.4 ($C_{pyrrole}$).

$^{19}$F NMR (376 MHz, CDCl$_3$): δ (ppm)=−145.33 (d, J=14.5 Hz, 2F, $CF_{meta}$), −146.14-−146.29 ($m_c$, 2F, $BF_2$), −158.57 (d, J=15.4 Hz, 2F, $CF_{meta}$).

HRMS (ESI-TOF): m/z calcd. for $C_{22}H_{15}BBr_2F_6N_3^-$ [M−H]$^-$: 605.9615, found: 605.9587.

UV/Vis (DCM): $\lambda_{max}$ (nm) [log (ε/L mol$^{-1}$ cm$^{-1}$)]=391 [3.97], 546 [4.76].

2.12 2,6-Dibromo-8-[4-(N-2-hydroxyethylamino)-2,3,5,6-tetrafluorophenyl]-1,3,5,7-tetramethyl-4,4-difluoro-4-bora-3a,4a-diaza-s-indacene

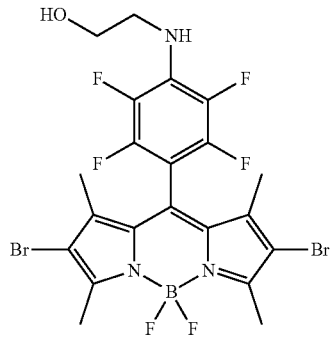

2,6-Dibromo-8-[4-(N-2-hydroxyethylamino)-2,3,5,6-tetrafluorophenyl]-1,3,5,7-tetramethyl-4,4-difluoro-4-bora-3a,4*-diaza-s-indacene was prepared according to the general synthetic procedure. 8-[4-(N-2-Hydroxyethylamino)-2,3,5,6-tetrafluorophenyl]-1,3,5,7-tetramethyl-4,4-difluoro-4-bora-3a,4a-diaza-s-indacene (94 mg, 0.21 mmol) and NBS (92 mg, 0.52 mmol) were dissolved in 2 mL of HFIP. The mixture was stirred for 1 min. The crude product was purified by column chromatography (silica gel, EtOAc/n-hexane=1/9, v/v) to obtain the product as a red solid (56 mg, 44%).

Mp: 103-108° C.

$^1$H NMR (500 MHz, THF-$d_8$): δ (pp)=1.73 (s, 6H, Me), 2.57 (s, 6H, Me), 3.54-3.58 (m, 2H, $CH_2$), 3.69-3.72 (m, 2H, $CH_2$), 4.05 (t, J=5.2 Hz, 1H, OH), 5.715-5.74 (NH).

$^{13}$C NMR (126 MHz, THF-$d_8$): δ (ppm)=13.2 (Me), 14.0 (Me), 48.7 ($CH_2$), 62.3 ($CH_2$), 112.9-113.0 (m, CBr), 124.7 ($C_{meso}$), 132.0 (Ar—$C_{para}$), 132.0 ($C_{pyrrole}$), 140.5 ($C_{pyrrole}$), 156.2 ($C_{pyrrole}$).

$^{19}$F NMR (376 MHz, CDCl$_3$): δ (ppm)=−145.76 (d, J=15.7 Hz, 2F, $CF_{meta}$), −146.21-−146.38 ($m_c$, 2F, $BF_2$), −160.61 (d, J=15.4 Hz, 2F, $CF_{meta}$).

HRMS (ESI-TOF): m/z calcd. for $C_4H_{18}BBr_2F_6N_3ONa^+$ [M+Na]$^+$: 635.9686, found: 635.9687, m/z calcd. for $C_{24}H_{18}BBr_2F_6N_3OK^+$ [M+K]$^+$: 651.9425, found: 651.9436, m/z calcd. for $C_{48}H_{36}B_2Br_4F_2N_4O_2Na^+$ [2M+Na]$^+$: 1248.9479, found: 1248.9480.

UV/Vis (DCM): $\lambda_{max}$ (nm) [log (ε/L mol$^{-1}$ cm$^{-1}$)]=391 [4.03], 546 [4.83].

2.13 2,6-Dibromo-8-[3-nitro-4-(1'-thio-β-D-glucosyl)phenyl]-1,3,5,7-tetramethyl-4,4-difluoro-4-bora-3a,4a-diaza-s-indacene

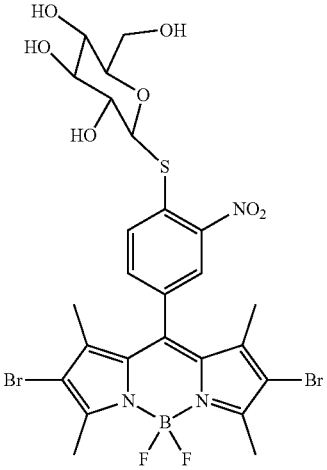

2,6-Dibromo-8-[3-nitro-4-(1'-thio-β-D-glucosyl)phenyl]-1,3,5,7-tetramethyl-4,4-difluoro-4-bora-3a,4a-diaza-s-indacene was prepared according to the general synthetic procedure. 8-[3-Nitro-4-(1'-thio-β-D-glucosyl)phenyl]-1,3,5,7-tetramethyl-4,4-difluoro-4-bora-3a,4a-diaza-s-indacene (100 mg, 0.18 mmol) and NBS (79 mg, 0.44 mmol) were dissolved in 2 mL of HFIP. The mixture was stirred for 1 min. The crude product was purified by column chromatography (silica gel, DCM/MeOH=9/1, v/v) to obtain the product as a red-brown solid (44 mg, 35%).

Mp: >250° C.

$^1$H NMR (500 MHz, THF-$d_8$): δ (ppm)=1.50 (d, J=6.1 Hz, 6H, Me), 2.57 (s, 6H, Me), 3.34-3.38 (m, 3H, 2'-H+3'-H+4'-H), 3.43 (ddd, J=8.6, 5.7, 2.1 Hz, 1H, 5'-H), 3.56 (d, J=7.1 Hz, 1H, 6'-H), 3.81 (dd J=11.9, 2.5 Hz, 1H, 6'-H), 4.57 (br s, 1H, OH), 4.81 (br s, 1H, OH), 4.90-4.92 (m, 1H, 1'-H), 5.06 (br s, 1H, OH), 7.66 (dd, J=8.3, 2.0 Hz, 1H, Ar—H$_{meta}$), 8.16 (d, J=8.3 Hz, 1H, Ar—H$_{ortho}$) 8.26 (d, J=2.0 Hz, 1H, Ar—H$_{ortho}$).

$^{13}$C NMR (126 MHz, THF-$d_8$): δ (ppm)=13.9 (Me), 14.8 (Me), 63.1 (6'-C), 71.3 (4'-C), 73.96 (2'-C), 80.3 (3'-C), 83.3 (5'-C), 86.6 (1'-C), 112.6 (CBr), 126.6 (Ar—C$_{ortho}$), 131.5 (Ar—C$_{meta}$), 132.4 (C$_{pyrrole}$), 134.3 (Ar—C$_{ortho}$), 139.3 (Ar—C$_{para}$), 140.5*, 141.2 (C$_{pyrrole}$), 141.3*, 148.5 (C$_{meso}$), 155.4 (C$_{pyrrole}$). *These signals could not be assigned exactly to the corresponding carbon atoms. They belong to the Ar—C$_{ipso}$ and the Ar—C$_{nitro}$ of the aryl moiety.

$^{19}$F NMR (376 MHz, THF-$d_8$): δ (ppm)=−146.22−−146.46 (m$_c$, 2F, BF$_2$).

HRMS (ESI-TOF): m/z calcd. for C$_{25}$H$_{26}$BBr$_2$F$_2$N$_3$O$_7$SNa$^+$ [M+Na]$^+$: 743.9791. found: 743.9789.

UV/Vis (MeOH): λ$_{max}$ (nm) [log (ε/L mol$^{-1}$ cm$^{-1}$)]=372 [4.04], 530 [4.72].

2.14 2,6-Dibromo-8-[3-nitro-4-(1'-thio-β-D-galactosyl)phenyl]-1,3,5,7-tetramethyl-4,4-difluoro-4-bora-3a,4a-diaza-s-indacene

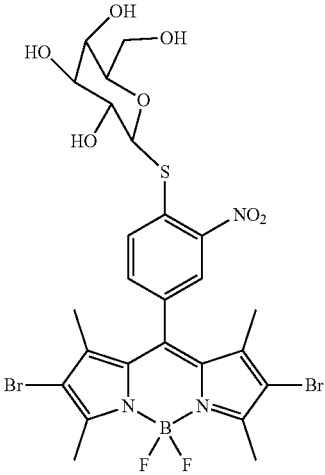

2,6-Dibromo-8-[3-nitro-4-(1'-thio-β-D-galactosyl)phenyl]-1,3,5,7-tetramethyl-4,4-difluoro-4-bora-3a,4a-diaza-s-indacene was prepared according to the general synthetic procedure. 8-[3-nitro-4-(1'-thio-β-D-galactosyl)phenyl]-1,3,5,7-tetramethyl-4,4-difluoro-4-bora-3a,4a-diaza-s-indacene (100 mg, 0.18 mmol) and NBS (79 mg, 0.44 mmol) were dissolved in 2 mL of HFIP. The mixture was stirred for 1 min. The crude product was purified by column chromatography (silica gel, DCM/MeOH=9/1, v/v) to obtain the product as a red solid (58 mg, 45%).

Mp: >250° C.

$^1$H NMR (500 MHz, DMSO-$d_6$): δ (ppm)=1.40 (s, 6H, Me), 2.47 (s, 6H, Me), 3.39-3.46 (m, 3H, 3'-H+6'-H), 3.54-3.62 (m, 3H, 2'-H+5'-H), 3.72 (br s, 1H, 4'-H), 4.90 (d, J=9.4 Hz, 1H, 1'-H), 7.73 (d, J=7.0 Hz, 1H, Ar—H$_{ortho}$), 8.03 (d, J=8.0 Hz, 1H, Ar—H$_{meta}$), 8.27 (br s, 1H, Ar—H$_{ortho}$).

$^{13}$C NMR (126 MHz, DMSO-$d_6$): δ (ppm)=13.5 (Me), 14.1 (Me), 60.3 (6'-C), 68.2 (4'-C), 69.1 (2'-C), 74.6 (3-C), 79.2 (5'-C), 84.9 (1'-C), 111.5-111.6 (m, CBr), 125.4 (Ar—C$_{ortho}$), 129.9*, 130.1 (Ar—C$_{meta}$), 130.3 (C$_{pyrrole}$), 133.3 (Ar—C$_{ortho}$), 136.99*, 139.4 (Ar—C$_{para}$), 140.2 (C$_{pyrrole}$), 146.8 (C$_{meso}$), 153.7 (C$_{pyrrole}$). *These signals could not be assigned exactly to the corresponding carbon atoms. They belong to the Ar—C$_{ipso}$ and the Ar—C$_{nitro}$ of the aryl moiety.

$^{19}$F NMR (376 MHz, DMSO-$d_8$): δ (ppm)=−143.15−−143.36 (m$_c$, 2F, BF$_2$).

HRMS (ESI-TOF): m/z calcd. for C$_{25}$H$_{26}$BBr$_2$F$_2$N$_3$O$_7$SNa$^+$ [M+Na]$^+$: 743.9791. found: 743.9849.

UV/Vis (MeOH): λ$_{max}$ (nm) [log (ε/L mol$^{-1}$ cm$^{-1}$)]=371 [4.08], 530 [4.80].

2.15 2,6-Dibromo-8-[2,3,5,6-tetrafluoro-4-(1'-thio-β-D-glucosyl)phenyl]-1,3,5,7-tetramethyl-4,4-difluoro-4-bora-3a,4a-diaza-s-indacene

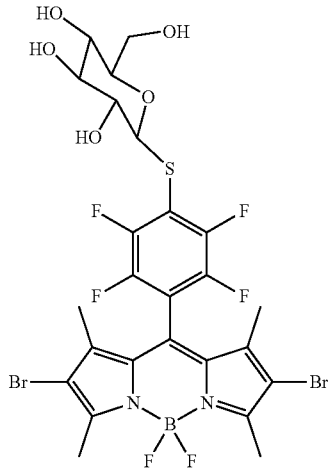

2,6-Dibromo-8-[2,3,5,6-tetrafluoro-4-(1'-thio-β-D-glucosyl)phenyl]-1,3,5,7-tetramethyl-4,4-difluoro-4-bora-3a,4a-diaza-s-indacene was prepared according to the general synthetic procedure. 8-[2,3,5,6-Tetrafluoro-4-(1'-thio-f D-glucosyl)phenyl]-1,3,5,7-tetramethyl-4,4-difluoro-4-bora-3a,4a-diaza-s-indacene (100 mg, 0.17 mmol) and NBS (75 mg, 0.42 mmol) were dissolved in 2 mL of HFIP. The mixture was stirred for 1 min. The crude product was purified by column chromatography (silica gel, DCM/MeOH=9/1, v/v) to obtain the product as a dark yellow solid (79 mg, 62%).

Mp: 162-169° C.

$^1$H NMR (500 MHz, THF-$d_8$): δ (ppm)=−1.69 (s, 6H, Me), 2.58 (s, 6H, Me), 3.21 (dd, J=5.4, 2.6 Hz, 1H, 5'-H), 3.26-3.29 (m, 2H, 2'-H+3'-H+4'-H), 3.50 (dd, J=11.7, 5.3 Hz, 1H, 6'-H), 3.67 (dd, J=11.7, 2.6 Hz, 1H, 6'-H), 4.89-4.90 (m, 1H, 1'-H), 4.91 (s, 1H, OH).

$^{13}$C NMR (126 MHz, THF-$d_8$): δ (ppm)=13.3 (Me), 14.1 (Me), 62.9 (6'-C), 71.5 (2'-C), 76.3 (4'-C), 79.97 (3'-C), 82.9 (5'-C), 85.7 (1'-C), 113.4 (CBr), 117.1 (Ar—$C_{ipso}$), 130.9 ($C_{pyrrole}$), 140.6 ($C_{pyrrole}$), 157.0 ($C_{pyrrole}$).

$^{19}$F NMR (376 MHz, THF-$d_8$): δ (ppm)=−131.51 (dd, J=24.2, 10.3 Hz, 2F, $CF_{ortho}$), −142.80 (dd, J=24.1, 10.7 Hz, 2F, $CF_{meta}$), −146.07--146.32 (m, 2F, $BF_2$).

HRMS (ESI-TOF): m/z calcd. for $C_{25}H_{23}BBr_2F_6N_2O_5SNa^+$ [M+Na]$^+$: 770.9563, found: 770.9560, m/z calcd. for $C_{50}H_{46}B_2Br_4F_{12}N_4O_{10}SNa^+$ [2M+Na]$^+$: 1518.9235, found: 1518.9218.

UV/Vis (DCM): $\lambda_{max}$ (nm) [log (ε/L mol$^{-1}$ cm$^{-1}$)]=544 [4.63].

2.16 2,6-Dibromo-8-[2,3,5,6-tetrafluoro-4-(1'-thio-β-D-galactosyl)phenyl]-1,3,5,7-tetramethyl-4,4-difluoro-4-bora-3a,4a-diaza-s-indacene

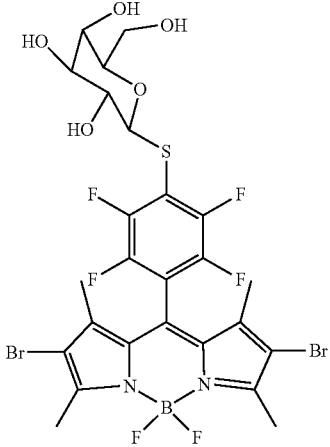

2,6-Dibromo-8-[2,3,5,6-tetrafluoro-4-(1'-thio-β-D-galactosyl)phenyl]-1,3,5,7-tetramethyl-4,4-difluoro-4-bora-3a, 4a-diaza-s-indacene was prepared according to the general synthetic procedure. 8-[2,3,5,6-Tetrafluoro-4-(1'-thio-β-D-galactosyl)phenyl]-1,3,5,7-tetramethyl-4,4-difluoro-4-bora-3a,4a-diaza-s-indacene (100 mg, 0.17 mmol) and NBS (75 mg, 0.42 mmol) were dissolved in 2 mL of HFIP. The mixture was stirred for 1 min. The crude product was purified by column chromatography (silica gel, DCM/MeOH=9/1, v/v) to obtain the product as a dark yellow solid (73 mg, 58%).

Mp: 173-180° C.

$^1$H NMR (500 MHz, THF-$d_8$): δ (ppm) 1.68 (s, 6H, Me), 2.58 (s, 6H, Me), 3.38 (dd, J=8.5, 3.7 Hz, 1H, 3'-H), 3.45 (t, J=6.0 Hz, 1H, 5'-H), 3.47 (dd, J=10.6, 5.6 Hz, 1H, 6'-H), 3.50 (dd, J=10.6, 6.0 Hz, 1H, 6'-H), 3.59-3.61 (m, 2H, 4'-H, 6'-H), 3.83 (d, J=2.7 Hz, 1H, 2'-H), 4.79 (d, J=9.3 Hz, 1H, 1'-H).

$^{13}$C NMR (126 MHz, THF-$d_8$): δ (ppm)=13.3 (Me), 14.1 (Me), 62.1 (6'-C), 70.0 (2'-C), 73.4 (4'-C), 76.5 (3'-C), 81.4 (5'-C), 86.2 (1-C), 113.3-113.4 (m, CBr), 114.00 (t, $J_{C-F}$=18.3 Hz, Ar—$C_{ipso}$), 116.90 (t, $J_{C-F}$=20.6 Hz, Ar—$C_{para}$), 125.9 ($C_{meso}$), 130.9 ($C_{pyrrole}$), 140.6 ($C_{pyrrole}$), 144.33 (dd, $J_{C-F}$=247.6, 18.1 Hz, Ar—$C_{meta}$), 14927 (dd, $J_{C-F}$=246.0, 14.9 Hz, Ar—$C_{ortho}$), 157.0 ($C_{pyrrole}$).

$^{19}$F NMR (376 MHz, THF-$d_8$): δ (ppm)=−131.09 (dd, J=25.2, 11.9 Hz, 2F, $CF_{ortho}$), −142.89 (dd, J=24.3, 10.8 Hz, 2F, $CF_{meta}$), −146.07--146.32 ($m_c$, 2F, $BF_2$).

HRMS (ESI-TOF): m/z calcd. for $C_{25}H_{23}BBr_2F_6N_2O_5SNa^+$ [M+Na]$^+$: 770.9563, found: 770.9550, m/z calcd. for $C_{50}H_{46}B_2Br_4F_{12}N_4O_{10}S_2Na^+$ [2M+Na]$^+$: 1518.9235, found: 1518.9208.

UV/Vis (DCM): $\lambda_{max}$ (nm) [log (ε/L mol$^{-1}$ cm$^{-1}$)]=393 [3.96], 544 [4.83].

2.17 2-Bromo-8-pentafluorophenyl-4,4-difluoro-4-bora-3a,4a-diaza-s-indacene

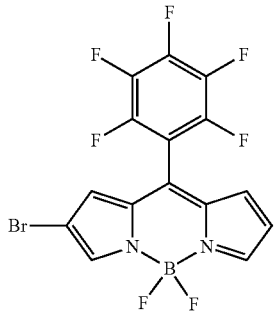

and 2,6-Dibromo-8-pentafluorophenyl-4,4-difluoro-4-bora-3a,4a-diaza-s-indacene

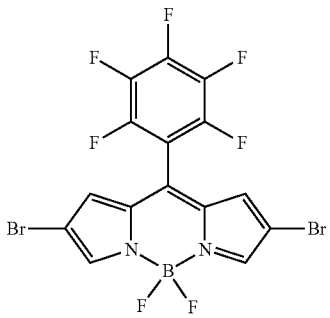

8-Pentafluorophenyl-4,4-difluoro-4-bora-3a,4a-diaza-s-indacene (which was prepared according to the literature: [7]) (257 mg, 0.72 mmol) was dissolved in 6 mL of DCM. NBS (286 mg, 1.61 mmol) was added and the mixture was stirred for 2.5 h at room temperature. Afterwards, the reaction mixture was diluted with EtOAc and washed with water several times. The organic layer was dried with $Na_2SO_4$, filtrated and evaporated to dryness. The crude product was purified by column chromatography (silica gel, DCM/n-hexane, 2/1, v/v) to obtain the 2,6-Dibromo-8-pentafluorophenyl-4,4-difluoro-4-bora-3a,4a-diaza-s-indacene as a greenish-red solid (31 mg, 8%) and the 2-Bromo-8-pentafluorophenyl-4,4-difluoro-4-bora-3a,4a-diaza-s-indacene as a red solid (148 mg, 47%).

2,6-Dibromo-8-pentafluorophenyl-4,4-difluoro-4-bora-3a,4a-diaza-s-indacene $^1$H NMR (400 MHz, $CDCl_3$): δ (ppm)=6.54 (s, 2H, $H_{pyrrole}$), 7.89 (s, 2H, $H_{pyrrole}$).

$^{13}$C NMR (126 MHz, $CDCl_3$): δ (ppm)=107.1 (t, $J_{C-F}$=17.6 Hz, Ar—$C_{ipso}$), 108.95-109.0 (m, $C_{Br}$), 128.9 (Ar—$C_{para}$), 130.6 ($C_{pyrrole}$), 134.9 ($C_{pyrrole}$), 138.1 (dd, $J_{C-F}$=254.9, 6.2 Hz, Ar—$C_{meta}$), 144.5 (dd, $J_{C-F}$=253.2, 8.4 Hz, Ar—$C_{ortho}$) 147.0 ($C_{pyrrole}$).

$^{19}$F NMR (376 MHz, $CDCl_3$): δ (ppm)=–136.30 (d, J=19.3 Hz, 2F, $CF_{meta}$), –144.63--144.85 (m$_c$, 2F, $BF_2$), –148.23 (t, J=20.8 Hz, $CF_{para}$), –158.58 (t, J=19.0 Hz (m, 2F, $CF_{ortho}$).

2-Bromo-8-pentafluorophenyl-4,4-difluoro-4-bora-3a,4a-diaza-s-indacene

M.P. (° C.): 141-146.
$^1$H NMR (700 MHz, $CDCl_3$): δ (ppm)=6.63-4.64 (m, 1H, $H_{pyrrole}$), 6.77 (s, 1H, $H_{pyrrole}$), 6.88 (d, J=4.5 Hz, 1H, $H_{pyrrole}$), 7.82 (s, 1H, $H_{pyrrole}$) 8.05 (s, 1H, $H_{pyrrole}$).
$^{13}$C NMR (176 MHz, $CDCl_3$): δ (ppm)=107.5-107.7 (m, Ar—$C_{ipso}$+CBr), 121.1 ($C_{pyrrole}$), 129.2 ($C_{pyrrole}$), 129.2 (Ar—$C_{para}$), 132.1 ($C_{pyrrole}$), 134.2 ($C_{pyrrole}$), 135.7 ($C_{pyrrole}$), 138.0 (ddd, $J_{C-F}$=255.2, 28.7, 5.2 Hz, Ar—$C_{meta}$), 144.6 (dd, $J_{C-F}$=253.0, 10.9 Hz, Ar—$C_{ortho}$) 144.8 ($C_{pyrrole}$), 149.1 ($C_{pyrrole}$).
$^{19}$F NMR (376 MHz, $CDCl_3$): δ (ppm)=–140.15 (dt, J=21.0, 5.5 Hz, 2F, $CF_{meta}$), –144.51--144.73 (m$_c$, 2F, $BF_2$), –153.67 (tt, J=20.7, 2.9 Hz, 1F, $CF_{para}$), –162.35--162.50 (m, 2F, $CF_{ortho}$).
HRMS (ESI-TOF): m/z calcd. for $C_{15}H_5BBrF_6N_2^+$ [M–F]$^+$: 416.9628, found: 416.9636, m/z calcd. for $C_{15}H_5BBrF_7N_2Na^+$ [M+Na]$^+$: 458.9510. found: 458.9516.
UV/Vis (DCM): $\lambda_{max}$ (nm) [log (ε/L mol$^{-1}$ cm$^{-1}$)]=536 [4.75].

General procedure for the halogenation of BODIPYs: The BODIPY was dissolved in DCM and NBS was added. The mixture was stirred for the indicated time at room temperature. Afterwards, the reaction mixture was diluted with EtOAc and washed with water several times. The organic layer was dried with $Na_2SO_4$, filtrated and evaporated to dryness. The crude product was purified by column chromatography.

2.18 2-Bromo-8-(4-Fluoro-3-nitrophenyl)-4,4-difluoro-4-bora-3a,4a-diaza-s-indacene

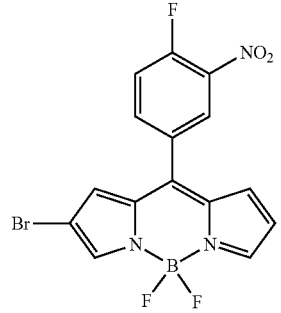

2-Bromo-8-(4-Fluoro-3-nitrophenyl)-4,4-difluoro-4-bora-3a,4a-diaza-s-indacen was prepared according to the general synthetic procedure. 8-(4-Fluoro-3-nitrophenyl)-4,4-difluoro-4-bora-3a,4a-diaza-s-indacene (which was prepared according to the literature: [14]) (100 mg, 0.30 mmol) and NBS (129 mg, 0.75 mmol) were dissolved in 5 mL of DCM. The mixture was stirred for 3 h. The crude product was purified by column chromatography (silica gel, DCM/n-hexane=1/1, v/v) to obtain the product as a reddish-green solid (79 mg, 64%).

M.P. (° C.): 165-167.
$^1$H-NMR (700 MHz, $CDCl_3$): δ (ppm)=6.66-6.67 (m, 1H, $H_{pyrrole}$), 6.81 (s, 1H, $H_{pyrrole}$), 6.93 (d, J=4.4 Hz, 1H, $H_{pyrrole}$), 7.53 (dd, J=10.1, 8.5 Hz, 1H, Ar—$H_{meta}$), 7.83-7.85 (m, 2H, $H_{pyrrole}$, Ar—$H_{ortho}$), 8.06 (s, 1H, $H_{pyrrole}$), 8.27 (dd, J=6.8, 2.3 Hz, 1H, Ar—$H_{ortho}$).
$^{13}$C-NMR (176 MHz, $CDCl_3$): δ (ppm)=107.2 (CBr), 119.5 (d, $J_{C-F}$=21.4 Hz, Ar $C_{meta}$), 120.8 ($C_{pyrrole}$), 127.8

(Ar—$C_{ortho}$), 129.8 ($C_{pyrrole}$), 130.1*, 132.6 ($C_{pyrrole}$), 134.0 ($C_{pyrrole}$), 135.3 ($C_{pyrrole}$), 136.9 (d, $J_{C-F}$=9.1 Hz, Ar—$C_{ortho}$), 137.7 (d, $J_{C-F}$=8.2 Hz)*, 142.0 ($C_{meso}$), 143.96 ($C_{pyrrole}$), 147.98 ($C_{pyrrole}$), 156.89 (d, $J_{C-F}$=271.0 Hz, Ar—$C_{para}$). *These signals could not be assigned exactly to the corresponding carbon atoms. They belong to the Ar—$C_{ipso}$ and the Ar—$C_{nitro}$ of the aryl moiety.

$^{19}$F-NMR (376 MHz, CDCl$_3$): δ (ppm)=−116.83 (s, 1F, CF), −144.18−−144.63 (m, 2F, BF$_2$).

HRMS (ESI-TOF): m/z calcd. for $C_{15}H_8BBrF_3N_3O_2Na^+$ [M+Na]$^+$: 431.9737, found 431.9743.

UV/Vis (DCM): $λ_{max}$ (nm) [log (ε/L mol$^{-1}$ cm$^{-1}$)]=527 [4.69].

2.19 2,6-Dibromo-8-(4-fluoro-3-nitrophenyl)-4,4-difluoro-4-bora-3a,4a-diaza-s-indacene

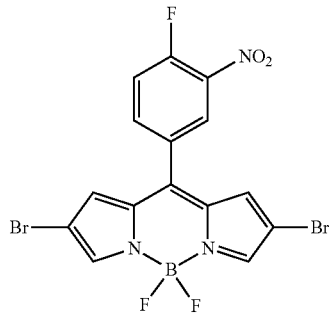

2,6-Dibromo-8-(4-fluoro-3-nitrophenyl)-4,4-difluoro-4-bora-3a,4a-diaza-s-indacene was prepared to the general synthetic procedure. 8-(4-Fluoro-3-nitrophenyl)-4,4-difluoro-4-bora-3a,4a-diaza-s-indacene (which was prepared according to the literature: (141) (50 mg, 0.15 mmol) and NBS (67 mg, 0.38 mmol) were dissolved in 5 mL of DCM. The mixture was stirred for 4 d. The crude product was purified by column chromatography (silica gel, DCM/n-hexane=1/1, v/v) to obtain the product as a dark yellow solid (15 mg, 20%).

M.P. (° C.): 170-179.

$^1$H-NMR (700 MHz, CDCl$_3$): δ (ppm)=6.88 (s, 2H, $H_{pyrrole}$), 7.54 (dd, J=10.0, 8.6 Hz, 1H, Ar—$H_{meta}$), 7.82 (ddd, J=8.6, 4.1, 2.3 Hz, 1H, Ar—$H_{ortho}$), 7.91 (s, 2H, $H_{pyrrole}$), 8.26 (dd, J=6.8, 2.3 Hz, 1H, Ar—$H_{ortho}$).

$^{13}$C-NMR (176 MHz, CDCl$_3$): δ (ppm)=108.5-108.6 (m, CBr), 119.7 (d, $J_{C-F}$=21.2 Hz, Ar—$C_{meta}$), 127.8 (Ar—$C_{ortho}$), 130.7 ($C_{pyrrole}$), 131.1*, 134.5 ($C_{pyrrole}$), 136.8 (d, $J_{C-F}$=9.3 Hz, Ar—$C_{ortho}$), 137.8 (d, $J_{C-F}$=6.6 Hz)*, 141.7 ($C_{meso}$), 146.1 ($C_{pyrrole}$), 157.06 (d, J=271.7 Hz, Ar—$C_{para}$). *These signals could not be assigned exactly to the corresponding carbon atoms. They belong to the Ar—$C_{ipso}$ and the Ar—$C_{nitro}$ of the aryl moiety.

$^{19}$F-NMR (376 MHz, CDCl$_3$): δ (ppm)=−111.98 (s, 1F, CF), −144.36−−144.98 (m, 2F, BF$_2$).

HRMS (ESI-TOF): m/z calcd. for $C_{15}H_7BBr_2F_3N_3O_2^-$ [M]$^-$: 488.8935, found: 488.8920.

UV/Vis (DCM): $λ_{max}$ (nm) [log (ε/L mol$^{-1}$ cm$^{-1}$)]=554 [4.78].

2.20 2-Bromo-[4-(N-butylamino)-3-nitrophenyl]-4,4-difluoro-4-bora-3a,4a-diaza-indacene

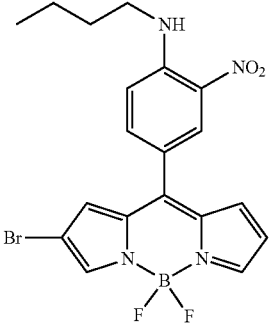

2-Bromo-8-[4-(N-butylamino)-3-nitrophenyl]-4,4-difluoro-4-bora-3a,4a-diaza-s-indacene was prepared according to the general synthetic procedure. 8-[4-(N-Butylamino)-3-nitrophenyl]-4,4-difluoro-4-bora-3a,4a-diaza-s-indacene (which was prepared according to the literature: [14]) (100 mg, 0.26 mmol) and NBS (116 mg, 0.65 mmol) were dissolved in 10 mL of DCM. The mixture was stirred for 3 h. The crude product was purified by column chromatography (silica gel, DCM/n-hexane=4/1, v/v) to obtain the product as a red solid (58 mg, 48%).

Mp: 129-132° C.

$^1$H-NMR (500 MHz, THF-d8): δ (ppm)=1.02 (t, J=7.4 Hz, 3H, Me), 1.48-1.55 (m, 2H, CH$_2$), 1.75-1.80 (m, 2H, CH$_2$), 3.48-3.52 (m, 2H, CH), 6.68 (d, J=4.3 Hz, 1H, $H_{pyrrole}$), 7.07 (s, 1H, $H_{pyrrole}$), 7.18 (d, J=4.1 Hz, 1H, $H_{pyrrole}$), 7.23 (d, J=9.0 Hz, 1H, Ar—$H_{meta}$), 7.80 (dd, J=8.9, 2.2 Hz, 1H, Ar—$H_{ortho}$), 7.89 (s, 1H, $H_{pyrrole}$), 8.06 (s, 1H, $H_{pyrrole}$), 8.46-8.48 (m, 1H, NH), 8.49 (d, J=22 Hz, 1H, Ar—$H_{ortho}$).

$^{13}$C-NMR (126 MHz, THF-d8): δ (ppm)=14.3 (Me), 21.2 (CH$_2$), 32.0 (CH$_2$), 43.8 (CH$_2$), 106.3 (CBr), 115.7 (Ar—$C_{meta}$), 120.5, 121.1 ($C_{pyrrole}$), 130.1 ($C_{pyrrole}$), 131.1 (Ar—$C_{ortho}$), 133.1 ($C_{pyrrole}$), 133.2*, 135.0 ($C_{pyrrole}$), 136.2 ($C_{pyrrole}$), 138.7 (Ar—$C_{ortho}$), 142.5 ($C_{pyrrole}$), 146.5 (Ar—$C_{para}$), 147.0 ($C_{pyrrole}$), 148.0 ($C_{meso}$). *These signals could not be assigned exactly to the corresponding carbon atoms. They belong to the Ar—$C_{ipso}$ and the Ar—$C_{nitro}$ of the aryl moiety.

$^{19}$F-NMR (376 MHz, THF-d$_8$): δ (ppm)=−145.44−−145.66 (m, 2F, BF$_2$).

HRMS (ESI-TOF): m/z calcd. for $C_{19}H_{18}BBrF_2N_4O_2Na^+$ [M+Na]$^+$: 485.0566, found: 485.0548.

UV/Vis (DCM): $λ_{max}$ (nm) [log (ε/L mol$^{-1}$ cm$^{-1}$)]=518 [4.73].

2.21 2-Bromo-8-[4-(N-cyclohexylamino)-3-nitrophenyl]-4,4-difluoro-4-bora-3a,4a-diaza-s-indacene

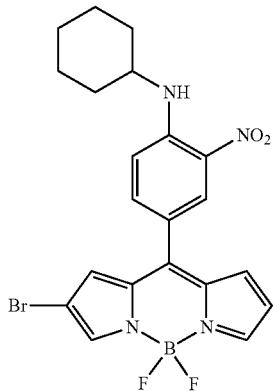

2-Bromo-8-[4-(N-cyclohexylamino)-3-nitrophenyl]-4,4-difluoro-4-bora-3a,4a-diaza-s-indacene was prepared according to the general synthetic procedure. 8-[4-(N-Cyclohexylamino)-3-nitrophenyl]-4,4-difluoro-4-bora-3a,4a-diaza-s-indacene (which was prepared according to the literature: [14]) (60 mg, 0.15 mmol) and NBS (65 mg, 0.37 mmol) were dissolved in 10 mL of DCM. The mixture was stirred for 3 h. The crude product was purified by column chromatography (silica gel, DCM/n-hexane=4/1, v/v) to obtain the product as a red solid (44 mg, 62%).

Mp: 207-213° C.

$^1$H-NMR (500 MHz, CD$_2$Cl$_2$): δ (ppm)=1.32-1.40 (m, 1H, CH$_{axial}$), 1.43-1.52 (m, 4H, CH$_{equat.}$), 1.67-1.72 (m, 1H, CH$_{equat.}$), 1.81-1.87 (m, 2H, CH$_{axial}$), 2.10-2.13 (m, 2H, CH$_{axial}$), 3.62-3.69 (m, 1H, CH), 6.66 (d, J=4.6 Hz, 1H, H$_{pyrrole}$), 6.99 (s, 1H, H$_{pyrrole}$), 7.08 (d, J=9.0 Hz, 1H, Ar—H$_{meta}$) 7.12 (d, J=4.4 Hz, 1H, H$_{pyrrole}$), 7.67 (dd, J=9.0, 2.2 Hz, 1H, Ar—H$_{ortho}$), 7.75 (s, 1H, H$_{pyrrole}$), 7.98 (s, 1H, H$_{pyrrole}$), 8.42-8.43 (m, 1H, NH), 8.46 (d, J=2.2 Hz, 1H, Ar—H$_{ortho}$).

$^{13}$C-NMR (126 MHz, CD$_2$Cl$_2$): δ (ppm)=24.9 (CH$_2$), 25.9 (CH$_2$), 32.96 (CH$_2$), 52.0 (CH), 106.0 (CBr), 115.4 (Ar—C$_{meta}$), 119.98 (C$_{pyrrole}$), 120.2*, 129.7 (C$_{pyrrole}$), 130.7 (Ar—C$_{ortho}$), 132.0 (C$_{pyrrole}$), 132.7*, 134.2 (C$_{pyrrole}$), 135.4 (C$_{pyrrole}$), 137.96 (Ar—C$_{ortho}$), 141.6 (C$_{pyrrole}$), 145.8 (Ar—C$_{para}$), 145.9 (C$_{pyrrole}$), 146.6 (C$_{meso}$). *These signals could not be assigned exactly to the corresponding carbon atoms. They belong to the Ar—C$_{ipso}$ and the Ar—C$_{nitro}$ of the aryl moiety.

$^{19}$F-NMR (376 MHz, CD$_2$Cl$_2$): δ (ppm)=−145.01-−145.23 (m$_c$, 2F, BF$_2$).

HRMS (ESI-TOF): m/z calcd. for C$_{21}$H$_{19}$BBrF$_2$N$_4$O$_2^-$ [M−H]$^-$: 487.0758, found: 487.0747.

UV/Vis (DCM): λ$_{max}$ (nm) [log (ε/L mol$^{-1}$ cm$^{-1}$)]=518 [4.55].

2.22 2-Bromo-8-[3-nitro-4-(N-prop-2-enylamino)phenyl]-4,4-difluoro-4-bora-3a,4a-diaza-s-indacene

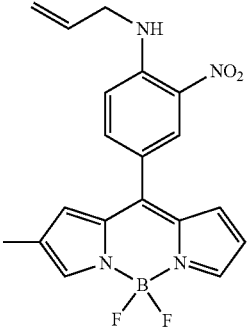

2-Bromo-8-[3-nitro-4-(N-prop-2-enylamino)phenyl]-4,4-difluoro-4-bora-3a,4a-diaza-s-indacene was prepared according to the general synthetic procedure. 8-[3-Nitro-4-(N-prop-2-enylamino)phenyl]-4,4-difluoro-4-bora-3a,4a-diaza-s-indacene (which was prepared according to the literature: [15]) (95 mg, 0.26 mmol) and NBS (115 mg, 0.65 mmol) were dissolved in 10 mL of DCM. The mixture was stirred for 3 h. The crude product was purified by column chromatography (silica gel, DCM/n-hexane=4/1, v/v) to obtain the product as a red solid (35 mg, 30%).

Mp: 160-162° C.

$^1$H-NMR (500 MHz, THF-d8): δ (ppm)=4.16-4.18 (m, 2H, CH$_2$), 5.23-5.26 (m, 1H, H$_2$C=CH—), 5.32-5.37 (m, 1H, H$_2$C=CH—), 6.01 (ddt, J=17.2, 10.1, 4.9 Hz, 1H, H$_2$C=CH—), 6.67 (d, J=4.5 Hz, 1H, H$_{pyrrole}$), 7.06 (s, 1H, H$_{pyrrole}$), 7.16-7.18 (m, 2H, H$_{pyrrole}$+Ar—H$_{meta}$), 7.79 (dd, J=9.0, 2.2 Hz, 1H, Ar—H$_{ortho}$), 7.89 (s, 1H, H$_{pyrrole}$), 8.06 (s, 1H, H$_{pyrrole}$), 8.50 (d, J=2.2 Hz, 1H, Ar—H$_{ortho}$), 8.66 (t, J=6.2 Hz, 1H, NH).

$^{13}$C-NMR (126 MHz, THF-d8): δ (ppm)=46.7 (CH$_2$), 106.4 (CBr), 116.1 (Ar—C$_{meta}$), 117.1 (H$_2$C=CH—), 120.5 (C$_{pyrrole}$), 121.4*, 130.1 (C$_{pyrrole}$), 130.97 (Ar—C$_{ortho}$), 133.25 (C$_{pyrrole}$), 133.33*, 134.8 (H$_2$C=CH—), 135.0 (C$_{pyrrole}$), 136.2 (C$_{pyrrole}$), 138.5 (Ar—C$_{ortho}$), 142.6 (C$_{pyrrole}$), 146.4 (Ar—C$_{para}$), 147.1 (C$_{pyrrole}$), 147.9 (C$_{meso}$). *These signals could not be assigned exactly to the corresponding carbon atoms. They belong to the Ar—C$_{ipso}$ and the Ar—C$_{nitro}$ of the aryl moiety.

$^{19}$F-NMR (376 MHz, THF-d8): δ (ppm)=−145.43-−145.66 (m$_c$, 2F, BF$_2$).

HRMS (ESI-TOF): m/z calcd. for C$_{18}$H$_{14}$BBrF$_2$N$_4$O$_2$Na$^+$ [M+Na]$^+$: 469.0253, found: 469.0262.

UV/Vis (DCM): λ$_{max}$ (nm) [log (ε/L mol$^{-1}$ cm$^{-1}$)]=519 [4.64].

2.23 2-Bromo-[4-(N-6-methoxy-6-oxohexylamino)-3-nitrophenyl]-4,4-difluoro-4-bora 3a,4a-diaza-s-indacene

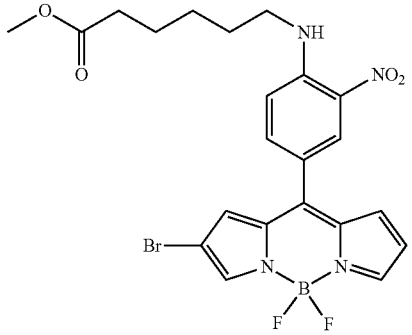

2-Bromo-8-[4-(N-6-methoxy-6-oxohexylamino)-3-nitrophenyl]-4,4-difluoro-4-bora-3a,4a-diaza-s-indacene was prepared according to the general synthetic procedure. 8-[4-(N-6-Methoxy-6-oxohexylamino)-3-nitrophenyl]-4,4-difluoro-4-bora-3a,4a-diaza-s-indacene (which was prepared according to the literature: [14]) (90 mg, 0.20 mmol) and NBS (87 mg, 0.49 mmol) were dissolved in 10 mL of DCM. The mixture was stirred for 3 h. The crude product was purified by column chromatography (silica gel, DCM) to obtain the product as a red solid (35 mg, 30%).

M.P. (° C.): 77-80.

$^1$H-NMR (500 MHz, THF-d8): δ (ppm)=1.48-1.54 (m, 2H, $CH_2$), 1.67-1.71 (m, 2H, $CH_2$), 1.77-1.83 (m, 2H, $CH_2$), 2.33 (t, J=7.4 Hz, 2H, CH), 3.50-3.53 (m, 2H, $CH_2$), 3.60 (s, 3H, Me), 6.68 (d, J=4.3 Hz, 1H, $H_{pyrrole}$), 7.07 (s, 1H, $H_{pyrrole}$), 7.18 (d, J=4.3 Hz, 1H, $H_{pyrrole}$), 7.23 (d, J=9.0 Hz, 1H, Ar—$H_{meta}$), 7.80 (dd, J=8.9, 2.2 Hz, 1H, Ar—$H_{ortho}$), 7.89 (s, 1H, $H_{pyrrole}$), 8.06 (s, 1H, $H_{pyrrole}$), 8.49 (d, J=2.2 Hz, 1H, Ar—$H_{ortho}$), 8.49-8.52 (m, 1H, NH).

$^{13}$C-NMR (126 MHz, THF-d8): δ (ppm)=25.6 ($CH_2$), 27.5 ($CH_2$), 29.6 ($CH_{12}$), 34.4 ($CH_2$), 43.9 ($CH_2$), 51.5 (Me), 106.3 (CBr), 115.7 (Ar—$C_{meta}$), 120.5 ($C_{pyrrole}$), 121.1*, 130.1 ($C_{pyrrole}$), 131.1 (Ar—$C_{ortho}$), 133.1 ($C_{pyrrole}$), 133.2*, 134.99 ($C_{pyrrole}$), 136.2 ($C_{pyrrole}$), 138.7 (Ar—$C_{ortho}$), 142.5 ($C_{pyrrole}$), 146.5 (Ar—$C_{para}$), 147.0 ($C_{pyrrole}$), 147.99 ($C_{meso}$), 173.8 (CO). *These signals could not be assigned exactly to the corresponding carbon atoms. They belong to the Ar—$C_{ipso}$ and the Ar—$C_{nitro}$ of the aryl moiety.

$^{19}$F-NMR (376 MHz, THF-d8): δ (ppm)=−145.42-−145.64 ($m_c$, 2F, $BF_2$).

HRMS (ESI-TOF): m/z calcd. for $C_{22}H_{22}BBrFN_4O_4^+$ [M−F]$^+$: 517.0888, found: 517.0894, m/z calcd. for $C_{22}H_{22}BBrF_2N_4O_4Na^+$ [M+Na]$^+$: 557.0778, found: 557.0809, m/z calcd. for $C_{22}H_{22}BBrF_2N_4O_4K^+$ [M+K]$^+$: 573.0517, found: 573.0542, m/z calcd. for $C_{44}H_{44}B_2Br_2F_4N_8O_8Na^+$ [2M+Na]$^+$: 1093.1668, found: 1093.1669.

UV/Vis (DCM): $\lambda_{max}$ (nm) [log (ε/L mol$^{-1}$ cm$^{-1}$)]=517 [4.74].

2.24 2-Bromo-8-[4-(N-prop-2-ynylamino)-2,3,5,6-tetrafluorophenyl]-4,4-difluoro-4-bora-3a,4a-diaza-s-indacene

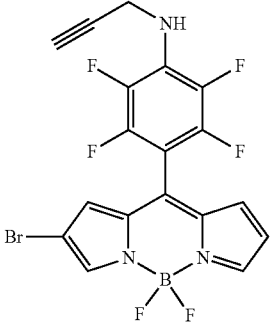

2-Bromo-8-[4-(N-prop-2-ynylamino)-2,3,5,6-tetrafluorophenyl]-4,4-difluoro-4-bora-3a,4a-diaza-s-indacene was prepared according to the general synthetic procedure. 8-[4-(N-prop-2-ynylamino)-2,3,5,6-tetrafluorophenyl]4,4-difluoro-4-bora-3a,4a-diaza-s-indacene (which was prepared according to the literature: [13]) (100 mg, 0.25 mmol) and NBS (113 mg, 0.64 mmol) were dissolved in 10 mL of DCM. The mixture was stirred for 1.5 h. The crude product was purified by column chromatography (silica gel, DCM/n-hexane=1/1, v/v) to obtain the product as a green solid (75 mg, 63%).

Mp: 80-82° C.

$^1$H NMR (500 MHz, THF-d$_6$): δ (ppm)=2.74 (t, J=2.4 Hz, 1H, CH), 4.22-4.24 (m, 2H, $CH_2$), 6.36 (s, 1H, NH), 6.67 (d, J=4.3 Hz, 1H, $H_{pyrrole}$), 7.07 (s, 1H, $H_{pyrrole}$), 7.15 (d, J=4.2 Hz, 1H, $H_{pyrrole}$), 7.94 (s, 1H, $H_{pyrrole}$), 8.13 (s, 1H, $H_{pyrrole}$).

$^{13}$C NMR (126 MHz, THF-d$_6$): δ (ppm)=35.3 ($CH_2$), 73.3 (CH), 81.6 (C), 99.97 (t, $J_{C-F}$=18.3 Hz, Ar—$C_{ipso}$), 107.1-107.2 (m, CBr), 121.5 ($C_{pyrrole}$), 130.4 ($C_{pyrrole}$), 130.9-131.1 (m, Ar—$C_{para}$), 132.7 ($C_{meso}$), 133.6 ($C_{pyrrole}$), 135.6 ($C_{pyrrole}$), 137.4 ($C_{pyrrole}$), 138.63 (dd, $J_{C-F}$=235.0, 22.2 Hz, Ar—$C_{meta}$), 144.5 ($C_{pyrrole}$), 138.63 (dd, $J_{C-F}$=235.0, 22.2 Hz), 145.91 (dd, $J_{C-F}$=246.2, 12.2 Hz, Ar—$C_{ortho}$), 149.6 ($C_{pyrrole}$).

$^{19}$F NMR (376 MHz, CDCl$_3$): δ (ppm)=−142.07 (d, J=17.7 Hz, 2H, $CF_{meta}$), −145.46-−145.68 ($m_c$, 2F, $BF_2$), −159.92 (d, J=17.9 Hz, 2F, $CF_{ortho}$).

HRMS (ESI-TOF): m/z calcd. for $C_{18}H_9BBrFN_3Na^+$ [M+Na]$^+$: 493.9869, found: 493.9886.

UV/Vis (DCM): $\lambda_{max}$ (nm) [log (ε/L mol$^{-1}$ cm$^{-1}$)]=389 [4.05], 536 [4.63].

2.25 2-Bromo-8-(4-butyloxy-2,3,5,6-tetrafluorophenyl)]-4,4-difluoro-4-bora-3a,4a-diaza-s-indacene

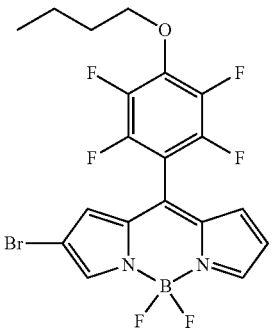

2-Bromo-8-(4-butyloxy-2,3,5,6-tetrafluorophenyl)]-4,4-difluoro-4-bora-3a,4a-diaza-s-indacene was prepared according to the general synthetic procedure. 8-(4-Butyloxy-2,3,5,6-tetrafluorophenyl)]-4,4-difluoro-4-bora-3a,4a-diaza-s-indacene (100 mg, 0.24 mmol) and NBS (108 mg, 0.61 mmol) were dissolved in 10 mL of DCM. The mixture was stirred for 1 h. The crude product as purified by column chromatography (silica gel, DCM/n-hexane=1/2, v/v) to obtain the product as a reddish-green solid (63 mg, 53%).

Mp: 114-116° C.

$^1$H NMR (500 MHz, THF-$d_6$): δ (ppm)=1.01 (t, J=7.4 Hz, 1H, Me), 152-1.59 (m, 2H, $CH_2$), 1.80-1.85 (m, 2H, $CH_2$), 4-40 (t, J=6.4 Hz, 2H, $CH_2$), 6.69 (d, J=4.4 Hz, 1H, $H_{pyrrole}$), 7.07 (s, 1H, $H_{pyrrole}$), 7.15 (d, J=4.4 Hz, 1H, $H_{pyrrole}$), 8.01 (s, 1H, $H_{pyrrole}$), 8.19 (s, 1H, $H_{pyrrole}$).

$^{13}$C NMR (126 MHz, THF-$d_6$): δ (ppm)=14.2 (Me), 19.9 ($CH_2$), 33.0 ($CH_2$), 76.4 ($CH_2$), 106.2-106.5 (m, Ar—$C_{ipso}$), 107.6-107.7 (m, CBr), 121.9 ($C_{pyrrole}$), 128.9 (Ar—$C_{para}$), 130.3 ($C_{pyrrole}$), 131.3 ($C_{meso}$), 133.6 ($C_{pyrrole}$), 135.4 ($C_{pyrrole}$), 137.2 ($C_{pyrrole}$), 141.26 (d $J_{C-F}$=70.4, 13.8 Hz, Ar—$C_{ortho}$), 144.3 ($C_{pyrrole}$), 138.63 (dd, $J_{C-F}$=235.0, 22.2 Hz), 145.91 (dd, $J_{C-F}$=253.0, 10.5 Hz, Ar—$C_{ortho}$), 150.5 ($C_{pyrrole}$).

$^{19}$F NMR (376 MHz, $CDCl_3$): δ (ppm)=−141.26 (d, J=19.1 Hz, 2F, $CF_{meta}$), −145.42−−145.64 (m$_c$, 2F, $BF_2$), −157.18 (d, J=17.3 Hz, 2F, $CF_{ortho}$).

HRMS (ESI-TOF): m/z calcd. for $C_{19}H_{14}BBrF_6N_2ONa^+$ [M+Na]$^+$: 513.0179, found: 513.0196, m/z calcd. for $C_{19}H_{14}BBrF_6N_2OK^+$ [M+K]$^+$: 530.9898, found: 530.9988.

UV/Vis (DCM): $\lambda_{max}$ (nm) [log (ε/L mol$^{-1}$ cm$^{-1}$)]=368 [4.11], 536 [4.71].

2.25 2-Bromo-8-[4-(prop-2-enyloxy)-2,3,5,6-tetrafluorophenyl]-4,4-difluoro-4-hora-3a,4a-diaza-s-indacene

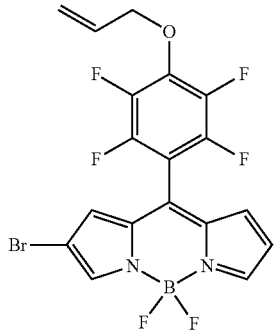

2-Bromo-8-[4-(prop-2-enyloxy)-2,3,5,6-tetrafluorophenyl]-4,4-difluoro-4-bora-3a,4a-diaza-s-indacene was prepared according to the general synthetic procedure. 8-[4-(Prop-2-enyloxy)-2,3,5,6-tetrafluorophenyl]-4,4-difluoro-4-bora-3a,4a-diaza-s-indacene (which was prepared according to the literature: [7]) (100 mg, 0.25 mmol) and NBS (112 mg, 0.63 mmol) were dissolved in 10 mL of DCM. The mixture was stirred for 1 h. The crude product was purified by column chromatography (silica gel, DCM/n-hexane=1/1, v/v) to obtain the product as a reddish-green solid (37 mg, 31%).

Mp: 101-103° C.

$^1$H NMR (500 MHz, THF-$d_6$): δ (ppm)=4.89 (d, J=5.9 Hz, 2H, $CH_2$), 5.34 (dd, J=10.4, 1.1 Hz, 1H, —HC=$CH_2$), 5.48 (dd, J=17.1, 1.5 Hz, 1H, —HC=CH), 6.11 (ddt, J=16.6, 10.9, 5.9 Hz, 1H, —HC=$CH_2$), 6.70 (d, J=4.3 Hz, 1H, $H_{pyrrole}$), 7.06 (s, 1H, $H_{pyrrole}$), 7.13 (d, J=4.3 Hz, 1H, $H_{pyrrole}$), 8.01 (s, 1H, $H_{pyrrole}$), 8.19 (s, 1H, $H_{pyrrole}$).

$^{13}$C NMR (126 MHz, THF-$d_6$): δ (ppm)=76.7 ($CH_2$), 106.74 (t, $J_{C-F}$=18.5 Hz, Ar—$C_{ipso}$), 107.6-107.7 (m, CBr), 119.98 (—HC=$CH_2$), 121.9 ($C_{pyrrole}$), 1303 ($C_{pyrrole}$), 131.2 ($C_{meso}$), 133.5 ($C_{pyrrole}$), 133.7 (—HC=$CH_2$), 135.4 ($C_{pyrrole}$), 137.2 ($C_{pyrrole}$), 140.36 (dd, $J_{C-F}$=8.1, 3.4 Hz, Ar—$C_{para}$), 142.60 (dd, $J_{C-F}$=242.4, 13.7 Hz, Ar—$C_{meta}$), 145.4 ($C_{pyrrole}$), 145.82 (dd, $J_{C-F}$=248.9, 19.3 Hz, Ar—$C_{ortho}$), 150.6 ($C_{pyrrole}$).

$^{19}$F NMR (376 MHz, $CDCl_3$): δ (ppm)=−141.18 (d, J=18.1 Hz, 2F, $CF_{meta}$), −145.45−−145.67 (m$_c$, 2F, $BF_2$), −156.46 (d, J=18.3 Hz, 2F, $CF_{ortho}$).

HRMS (ESI-TOF): m/z calcd. for $C_{18}H_{10}BBrF_4N_2ONa^+$ [M+Na]$^+$: 498.9845, found: 498.9851.

UV/Vis (DCM): $\lambda_{max}$ (nm)) [log (ε/L mol$^{-1}$ cm$^{-1}$)]=366 [4.05], 537 [4.66].

2.26 2-Bromo-8-[4-(prop-2-ynyloxy)-2,3,5,6-tetrafluoro-phenyl]-4,4-difluoro-4-bora-3a,4a-diaza-s-indacene

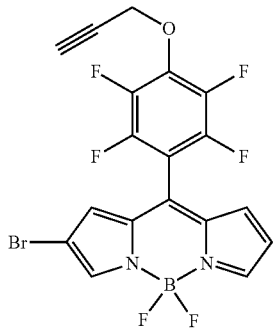

2-Bromo-8-[4-(prop-2-ynyloxy)-2,3,5,6-tetrafluoro-phenyl]-4,4-difluoro-4-bora-3a,4a-diaza-s-indacene was prepared according to the general synthetic procedure. 8-[4-(Prop-2-ynyloxy)-2,3,5,6-tetrafluoro-phenyl]-4,4-difluoro-4-bora-3a,4a-diaza-s-indacene (which was prepared according to the literature: [7]) (100 mg, 0.25 mmol) and NBS (113 mg, 0.64 mmol) were dissolved in 10 mL of DCM. The mixture was stirred for 1 h. The crude product was purified by column chromatography (silica gel, DCM/un-hexane=1/1, v/v) to obtain the product as a reddish-green solid (41 ng, 34%).

Mp: 139-141° C.

$^{1}$H NMR (500 MHz, THF-d$_6$): δ (ppm)=3.25 (t, J=2.4 Hz, 1H, CH), 5.06 (d, J=2.4 Hz, 2H, CH$_2$), 6.70 (d, J=4.3 Hz, 1H, H$_{pyrrole}$), 7.07 (s, 1H, H$_{pyrrole}$), 7.14 (d, J=4.2 Hz, 1H, H$_{pyrrole}$), 8.02 (s, 1H, H$_{pyrrole}$), 8.20 (s, 1H, H$_{pyrrole}$).

$^{13}$C NMR (126 MHz, THF-d$_6$): δ (ppm)=63.1 (CH$_2$), 78.2 (CH), 79.4 (C), 107.5-107.8 (m, CBr+Ar—C$_{ipso}$), 121.97 (C$_{pyrrole}$), 130.3 (C$_{pyrrole}$), 131.0 (C$_{meso}$), 133.5 (C$_{pyrrole}$), 135.3 (C$_{pyrrole}$), 137.1 (C$_{pyrrole}$), 139.1-139.3 (m, Ar—C$_{para}$), 142.92 (dd, J$_{C—F}$=248.7, 10.8 Hz, Ar—C$_{meta}$), 145.5 (C$_{pyrrole}$), 145.76 (dd, J$_{C—F}$=248.0, 13.2 Hz, Ar—C$_{ortho}$), 150.7 (C$_{pyrrole}$).

$^{19}$F NMR (376 MHz, CDCl$_3$): δ (ppm)=−140.98 (d, J=19.7 Hz, 2F, CF$_{meta}$), −145.43--−145.65 (m$_c$, 2F, BF$_2$), −155.64 (d, J=17.3 Hz, 2F, CF$_{ortho}$).

HRMS (ESI-TOF): m/z calcd. for C$_{18}$H$_8$BBrF$_6$N$_2$ONa$^+$ [M+Na]$^+$: 496.9689. found: 496.9686, m/z calcd. for C$_{18}$H$_8$BBrF$_6$N$_2$OK$^+$ [M+K]$^+$: 512.9428, found: 512.9428, m/z calcd. for C$_{36}$H$_{16}$B$_2$Br$_2$F$_2$N$_4$O$_2$Na$^+$ [2M+Na]$^+$: 968.9506, found: 8.9496.

UV/Vis (DCM): λ$_{max}$ (nm)([log (ε/L mol$^{-1}$ cm$^{-1}$)]=367 [4.09], 537 [4.73].

2.27 2-Bromo-8-[4-(N-butylamino)-3-nitrophenyl]-1,3,5,7-tetramethyl-4,4-difluoro-4-bora-3a,4a-diaza-s-indacene 8-[4-(N-Butylamino)-3-nitrophenyl]-1,3,5,7-tetramethyl-4,4-difluoro-4-bora-3a,4a-diaza-s-indacene (118 mg, 0.27 mmol) was dissolved in 5 mL of DCM. A solution of NBS (47 mg, 0.27 mmol) in 5 mL DCM was added dropwise and the mixture was stirred for 2 h at room temperature. Afterwards, the mixture was diluted with EtOAc and washed with water several times. The organic layer was dried with Na$_2$SO$_4$, filtrated and evaporated to dryness. The crude product was purified by column chromatography (silica gel, n-hexane/EtOAc=9/1, v/v) to obtain the product as a light orange solid (41 mg, 29%).

$^{1}$H-NMR (500 MHz, THF-d$_8$): δ (ppm)=1.01 (t, J=7.4 Hz, 3H, Me$_{butyl}$), 1.47-1.55 (m, 2H, CH$_2$), 1.57 (s, 3H, Me), 1.59 (s, 3H, Me), 1.74-1.79 (m, 2H, CH$_2$), 2.52 (s, 3H, Me), 2.53 (s, 3H, Me), 3.42-3.46 (m, 2H, CH$_2$), 6.14 (s, 1H, H$_{pyrrole}$), 7.24 (d, J=8.8 Hz, 1H, Ar—H$_{meta}$), 7.43 (dd, J=8.8, 2.1 Hz, 1H, Ar—H$_{ortho}$), 8.16 (d, J=2.1 Hz, 1H, Ar—H$_{ortho}$), 8.22 (t, J=4.7 Hz, 1H, NH).

$^{13}$C-NMR (126 MHz, THF-d$_8$): δ (ppm)=13.6 (Me), 14.3 (Me$_{butyl}$), 14.5 (Me), 14.9 (Me), 15.7 (Me), 21.3 (CH$_2$), 32.1 (CH$_2$), 43.8 (CH$_{42}$), 110.8-110.9 (m, CBr), 116.3 (Ar—C$_{meta}$), 121.7*, 1233 (CH$_{pyrrole}$), 127.8 (Ar—C$_{ortho}$), 131.2 (C$_{pyrrole}$), 133.1* 133.8 (C$_{pyrrole}$), 136.8 (Ar—C$_{ortho}$), 138.7 (C$_{pyrrole}$), 141.5 (C$_{pyrrole}$), 145.9 (C$_{meso}$), 146.8 (Ar—C$_{para}$), 151.9 (C$_{pyrrole}$), 154.7 (C$_{pyrrole}$). *These signals could not be assigned exactly to the corresponding carbon atoms. They belong to the Ar—C$_{ipso}$ and the Ar—C$_{nitro}$ of the aryl moiety.

$^{19}$F-NMR (376 MHz, THF-d$_8$): δ (ppm)=−146.53--−146.77 (m$_c$, 2F, BF$_2$).

HRMS (ESI-TOF): m/z calcd. for C$_3$H$_2$BBrF$_2$N$_4$O$_2$Na$^+$ [M+Na]$^+$: 541.1192, found: 541.1222, m/z calcd. for C$_{23}$H$_{26}$BBrF$_2$N$_4$O$_2$K$^+$ [M+K]$^+$: 559.0911, found: 559.0948 m/z calcd. for C$_{46}$H$_{52}$B$_2$Br$_2$F$_4$N$_8$O$_4$Na$^+$ [2M+Na]$^+$: 1061.2472, found: 1061.2518.

Example 3

Cell Tests of Selected Compounds in the HT 29 and Other Cell Lines

The photosensitizing activity was determined in the following cell lines:
HT29 (human colon adenocarcinoma cell line)
L929 (mouse fibroblast cell line)
A431 (human epidermoid carcinoma cell line)
A253 (submaxillary salivary gland, epidermoid cell line)

CAL-27 (human tongue squamous cell carcinoma cell line)

J774A.1 (Mouse BALB/c monocyte macrophage).

The cell lines were grown in DMEM (c.c.pro GmbH) supplemented with 10% heat-inactivated fetal calf serum (FCS, c.c.pro GmbH), 1% penicillin (10000 IU) and streptomycin (10000 µg/ml, c.c.pro GmbH). Cells were kept as a monolayer culture in a humidified incubator (5% $CO_2$ in air at 37° C.).

A photosensitizer stock solution (2 mM) was performed in DMSO and was kept in the dark at 4° C. Further dilution was performed in DMEM medium without phenol red supplemented with 10% FCS to reach a final photosensitizer concentration of 2 or 10 µM, respectively.

After seeding the cells in micro plates, the cells were incubated with fresh medium (DMEM without phenol red) containing 10% FCS with 2 or 10 µM of the photosensitizer for 24 h before light exposure. Before photosensitization, cells were washed, cell culture medium was exchanged with DMEM without phenol red and 10% FCS, then irradiated at room temperature with white light source at a fixed fluence rate of about 100 mW/$cm^2$ (50 J/$cm^2$). Following irradiation, cells were incubated in a humidified incubator (5% $CO_2$ in air at 37° C.) for 24 h until cell viability assay.

The cell viability was assessed by the XTT assay. 500 mg XTT (sodium 3'-[phenyl-aminocarbonyl)-3,4-tetrazolium]-bis(4-methoxy-6-nitro)benzene sulfonic acid, Applichem GmbH) is dissolved in 500 ml PBS-Buffer (without $Ca^{2+}$ and $Mg^2$) and sterile filtered. Solution was stored in the dark at −20° C. until use. A sterile solution containing PMS (N-methyl dibenzopyrazine methyl sulfate, Applichem GmbH) was needed as an activation reagent for the XTT. 0.383 mg PMS was dissolved in 1 ml PBS-Buffer. The solution should be stored frozen and should not be exposed to light. The XTT reagent solution was thawed in a 37° C. water bath and the activation solution (PMS) was added immediately prior to use. To prepare a reaction solution sufficient for one micro plate (96 wells), 0.1 ml activation solution (PMS) was given to 5 ml XTT reagent. The medium in the micro plate was exchanged with RPMI without phenol red and 10% FCS (100 µl) prior adding 50 µl XTT reaction solution per well. The micro plate was incubated for 2-3 hours at 37° C. and 5% $CO_2$ until an orange dye was formed. The micro plate has been shaken gently to evenly distribute the dye in the wells.

The absorbance of the samples was measured with a microplate reader (infinite 200, Tecan Group Ltd.) at a wavelength of 490 nm.

Figure 2:
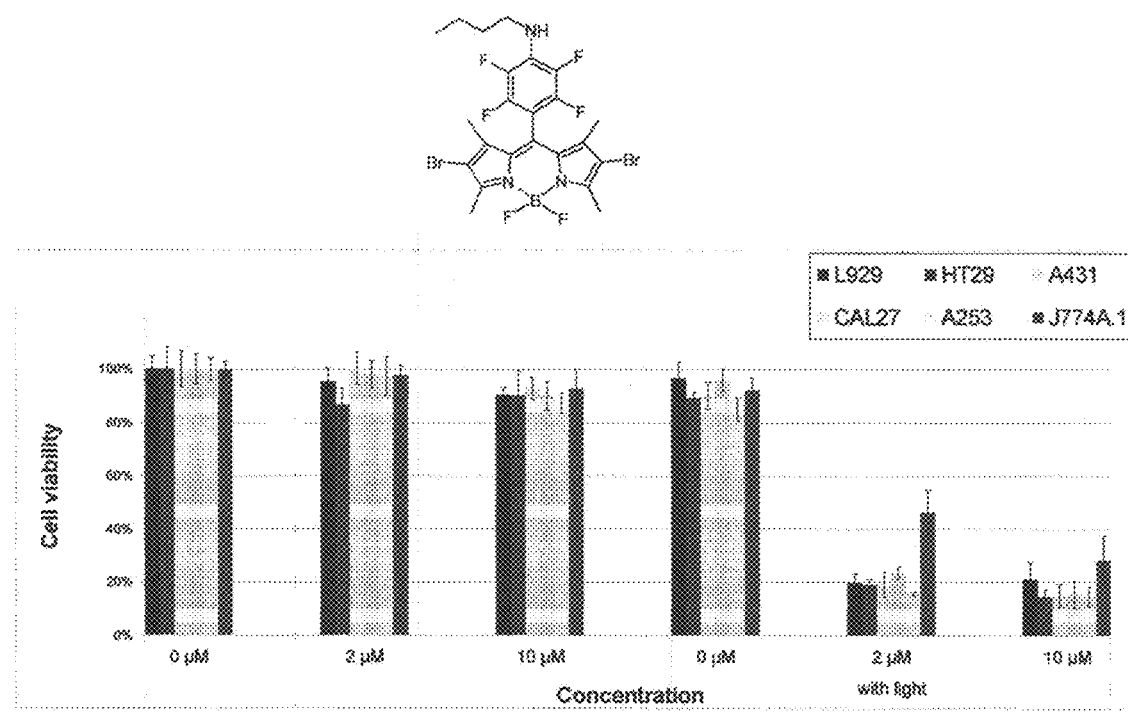
FIG. 2 shows the results of cell tests of 1,3,5,7-Tetramethyl-2,6-dibromo-8(4-N-butylamino-2,3,5,6-tetra-fluorophenyl)-boron dipyrromethene.
Figure 3:
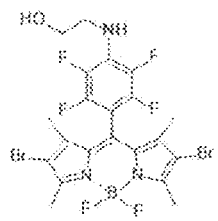
FIG. 3 shows the results of cell tests of 1,3,5,7-Tetramethyl-2,6-dibromo-8-(4-(2-hydroxyethylamino)-2,3,5,6-tetrafluorophenyl)boron dipyrromethene.
Figure 3:
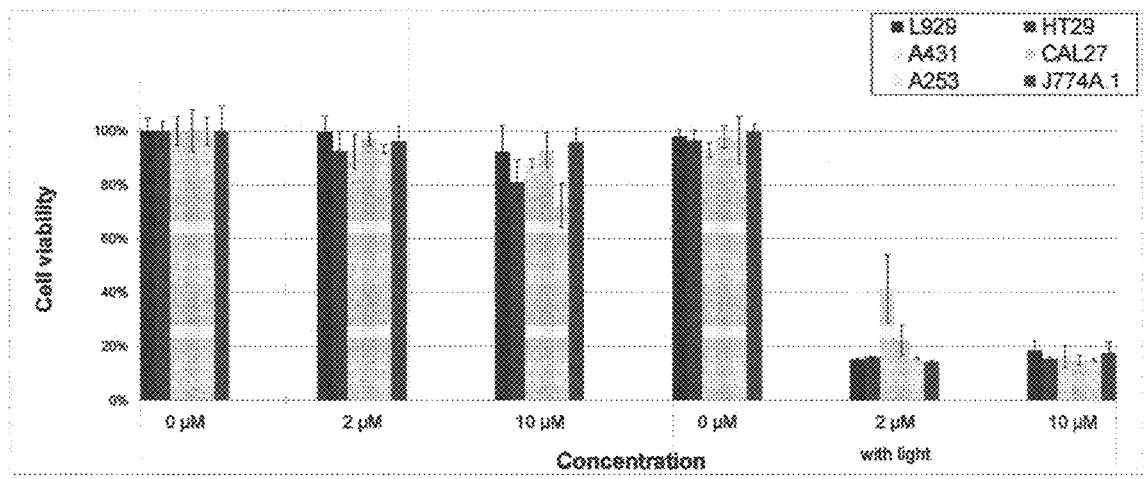
Figure 4:
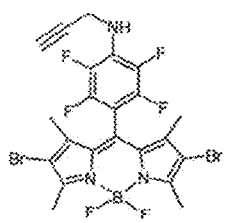
FIG. 4 shows the results of cell tests of 1,3,5,7-Tetramethyl-2,6-dibromo-8-(4-N-propargylamino-2,3,5,6-tetrafluorophenyl)-boron dipyrromethene.
Figure 4:
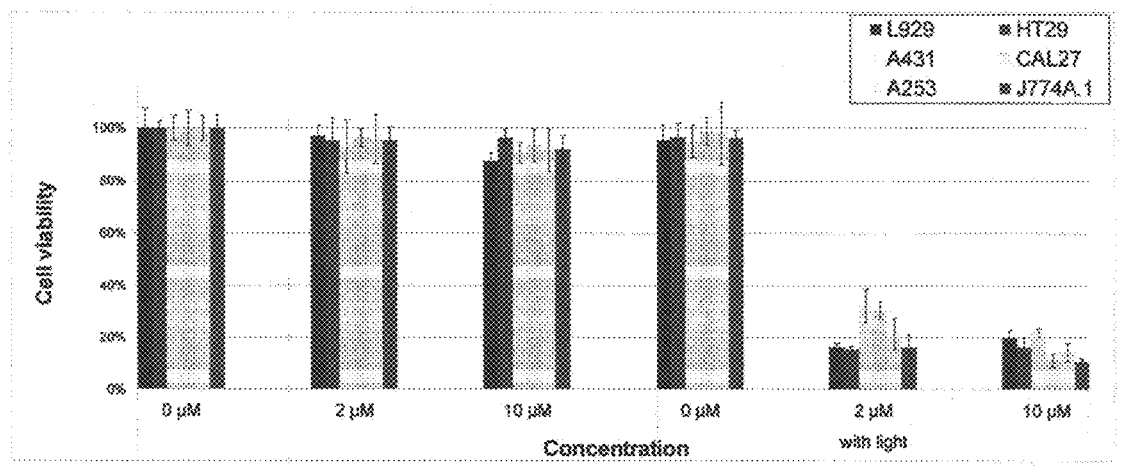
Figure 5:
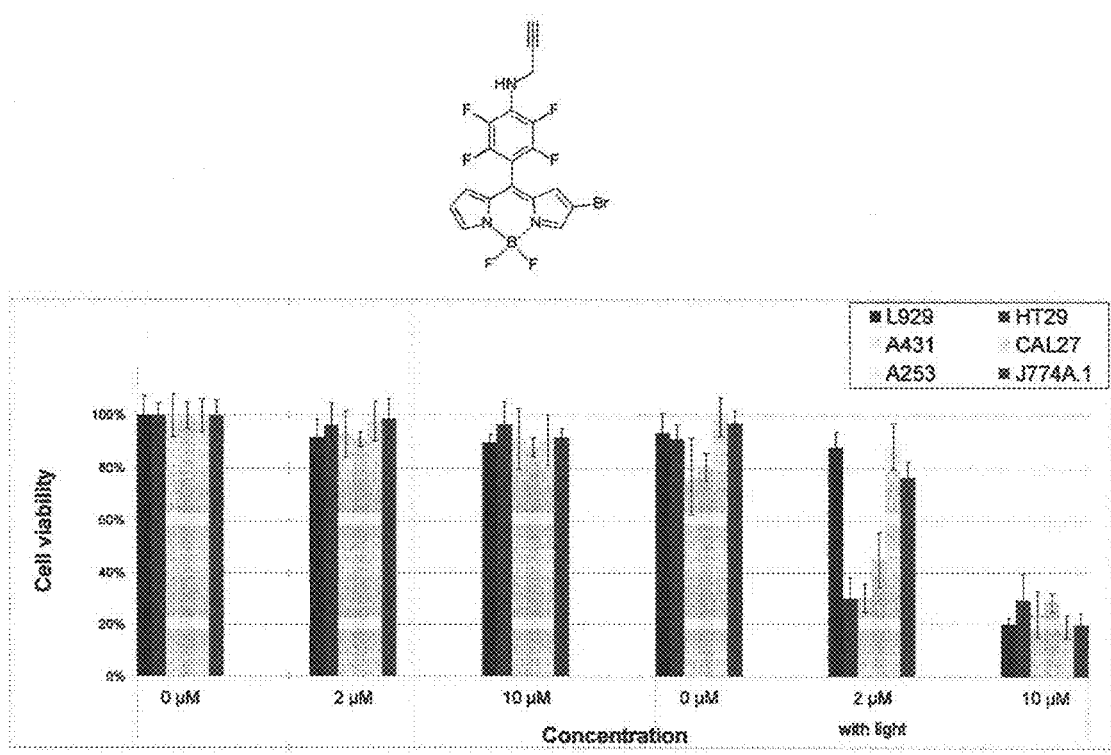
FIG. 5 shows the results of cell tests of 2-Bromo-8-(4-N-propargylamino-2,3,5,6-tetrafluorophenyl)-boron dipyrromethene.
Figure 6:
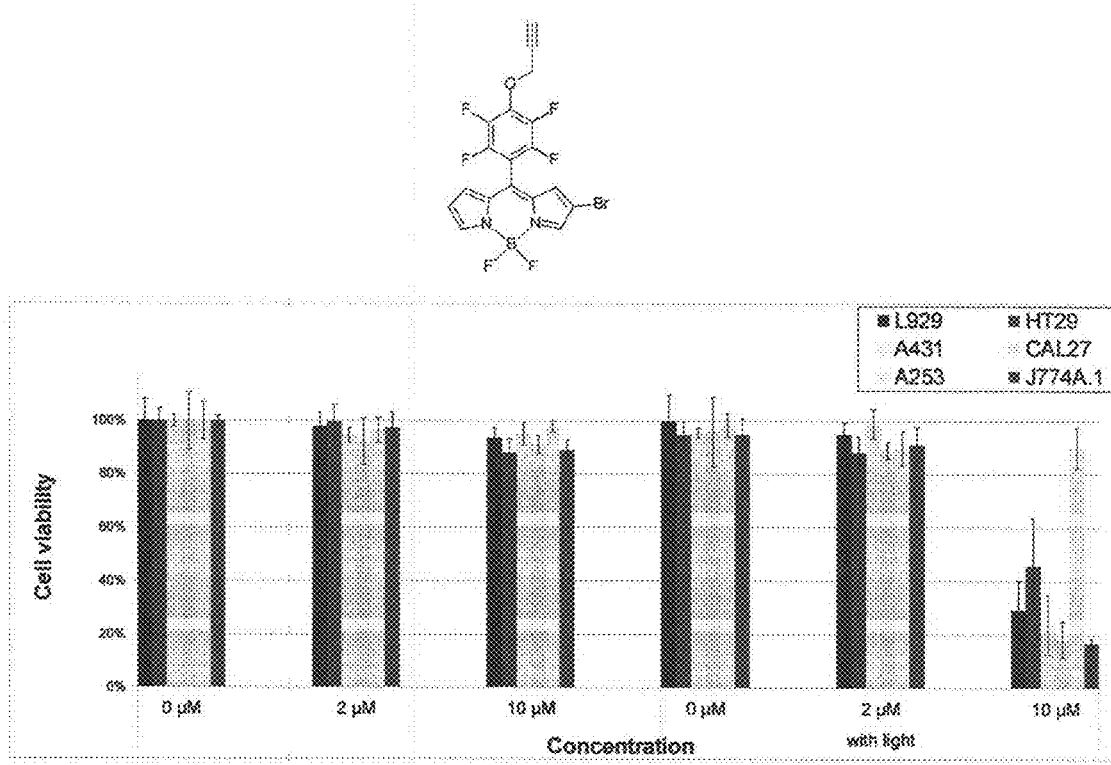
FIG. 6 shows the results of cell tests of 2-Bromo-8-(4-N-propargyloxy-2,3,5,6-tetrafluorophenyl)-boron dipyrromethene.
Figure 7:
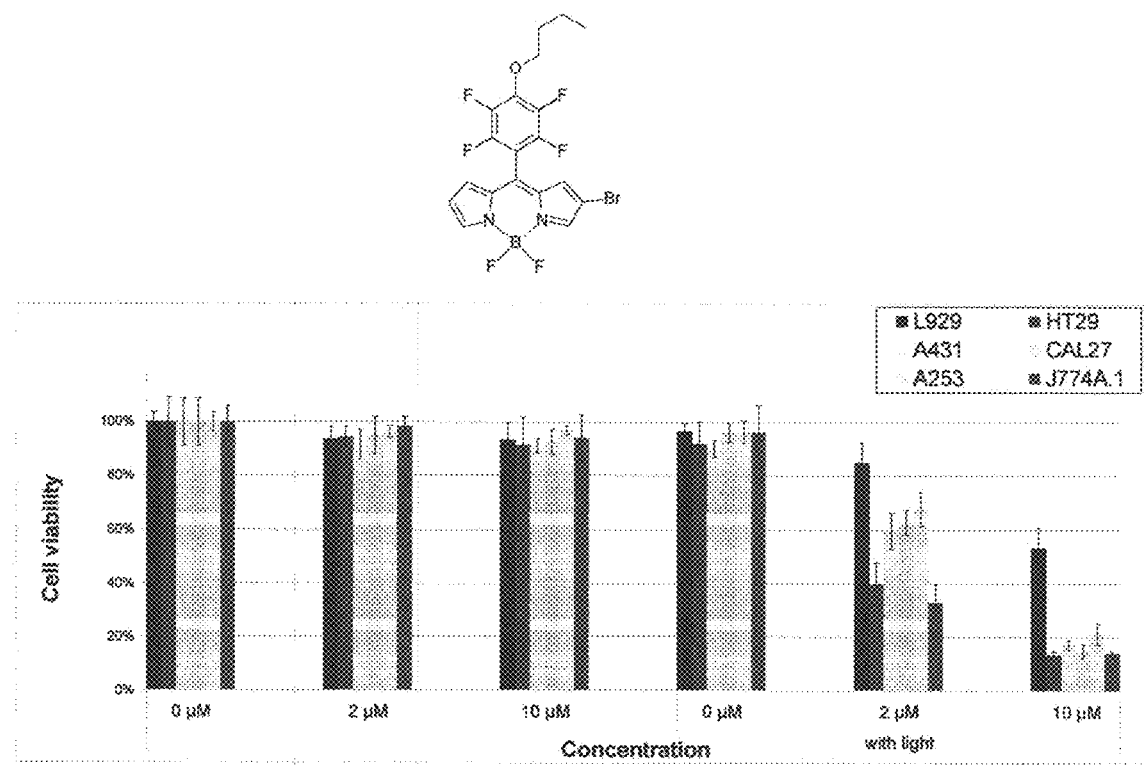
FIG. 7 shows the results of cell tests of 2-Bromo-8-(4-butyloxy-2,3,5,6-tetrafluorophenyl)-boron dipyrromethene.
Figure 8:
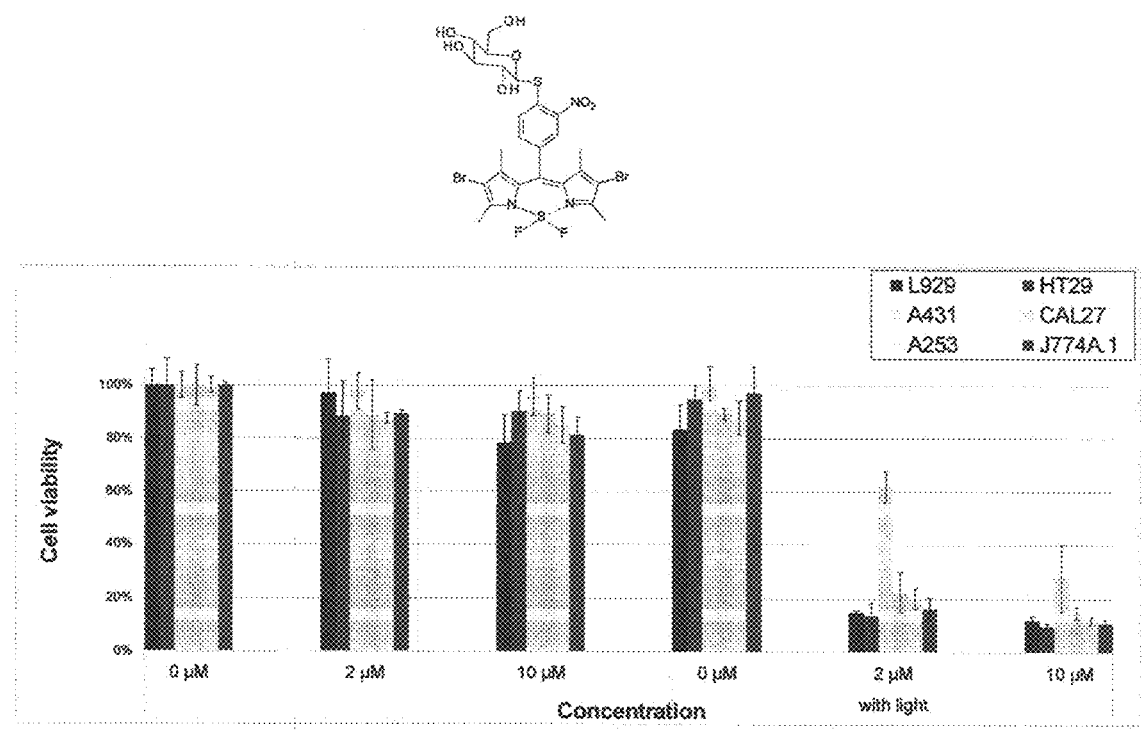
FIG. 8 shows the results of cell tests of 1,3,5,7-Tetramethyl-2,6-dibromo-8-[4-(β-D-glucosylthio)-3-nitrophenyl]-boron dipyrromethene.
Figure 9:
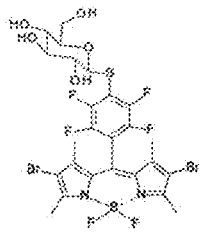
FIG. 9 shows the results of cell tests of 1,3,5,7-Tetramethyl-2,6-dibromo-8-[4-(β-D-glucosylthio)-2,3,5,6-tetrafluorophenyl]-boron dipyrromethene.
Figure 9:
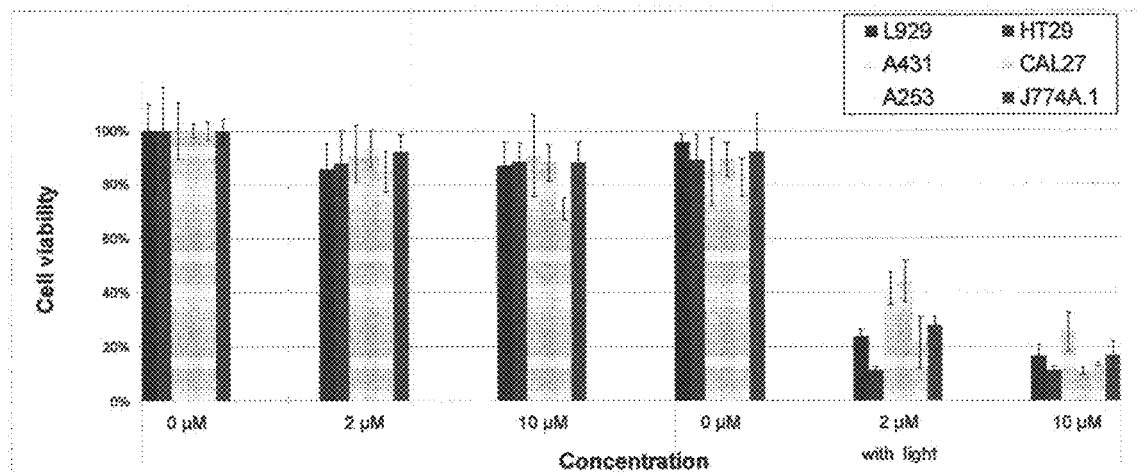
Figure 10:
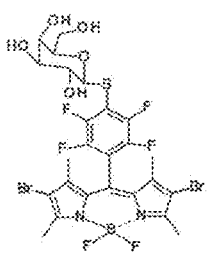
FIG. 10 shows the results of cell tests of 1,3,5,7-Tetramethyl-2,6-dibromo-8-[4-(β-D-galactosylthio)-2,3,5,6-tetrafluorophenyl]-boron dipyrromethene.
Figure 10:
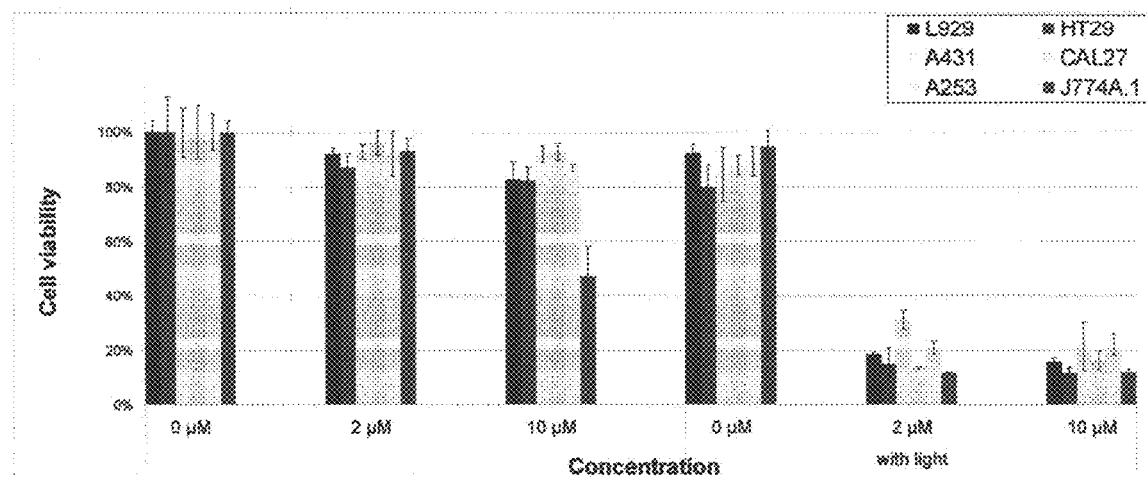
Figure 11:
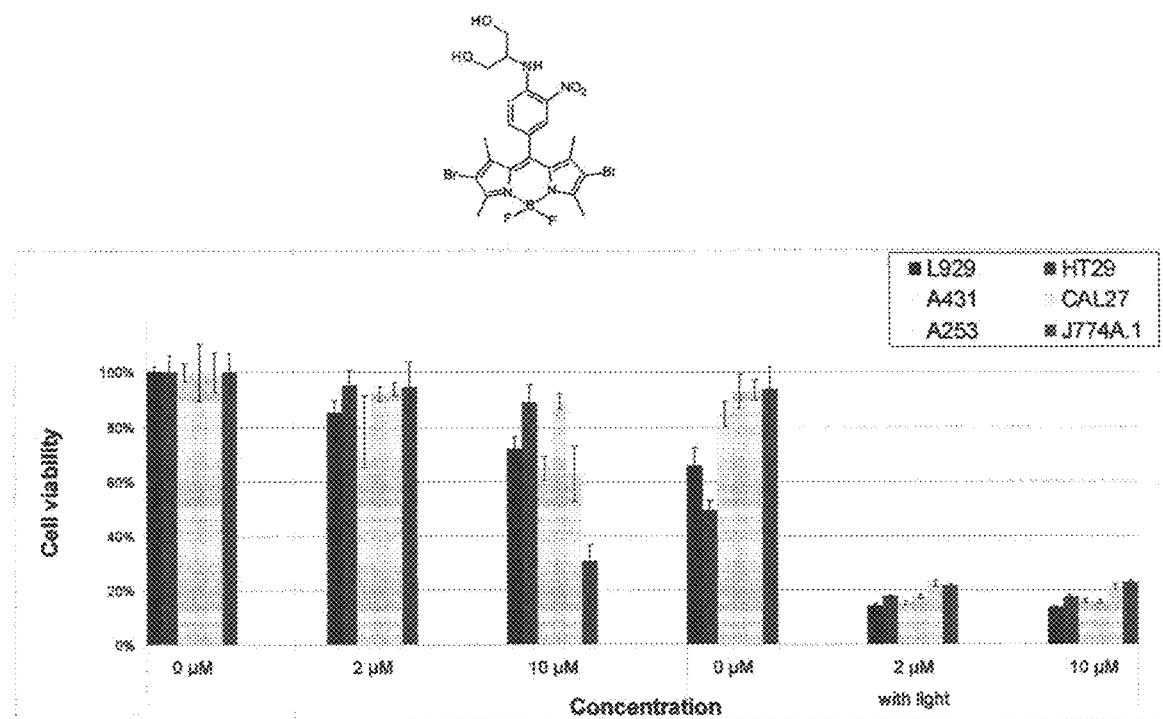
FIG. 11 shows the results of cell tests of 1,3,5,7-Tetramethyl-2,6-dibromo-8(4-(1-hydroxymethyl)-hydroxy-ethylamino-3-nitrophenyl)-boron dipyrromethene.
Figure 12:
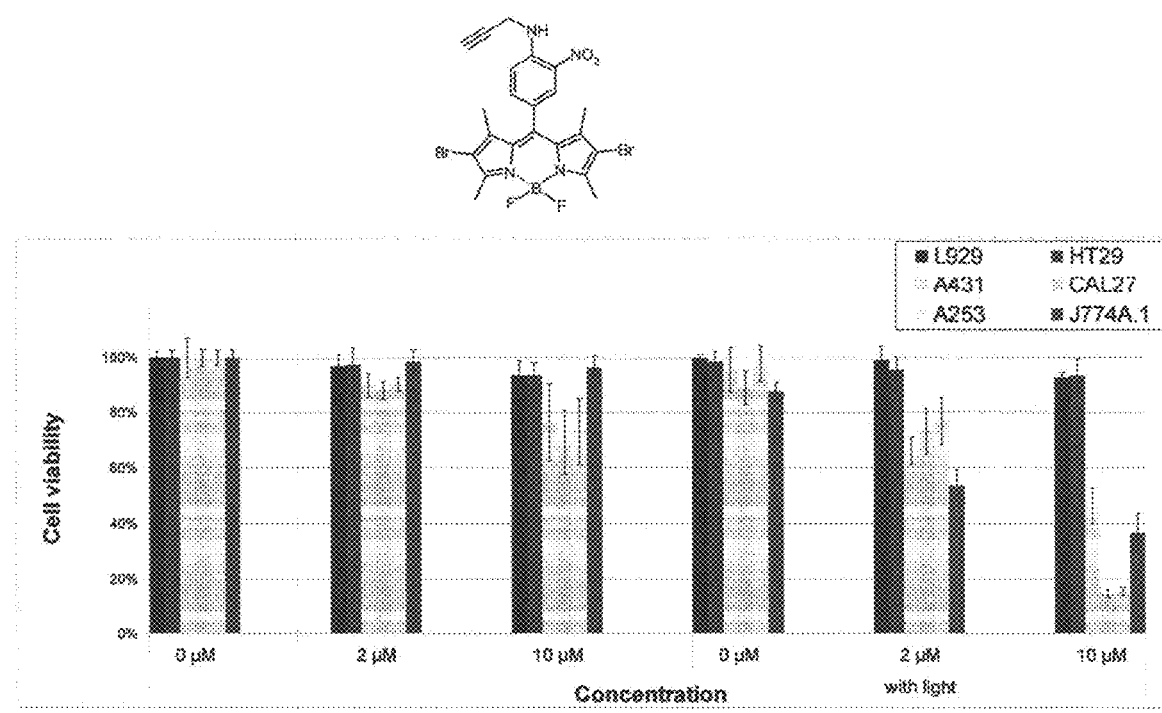
FIG. 12 shows the results of cell tests of 1,3,5,7-Tetramethyl-2,6-dibromo-8-(4-propargylamino-3-nitro-phenyl)-boron dipyrromethene.

The examples 3.1 to 3.12 (shown in FIGS. 1 to 12 respectively) illustrate the photodynamic activity ('with light' means phototoxicity) of selected compounds which am subject of the present invention. It is to be noted that the compounds are also active against the macrophage cell line J774A.1. As macrophages are relevant in inflammatory processes, the compounds of the present invention may also be applied in the diagnosis and treatment of inflammatory diseases, like arthritis or otitis media.

Example 4

Antibacterial Testing

The organisms studied were *Staphylococcus aureus* DSM 11729, Gram-positive and *Pseudomonas aeruginosa* DSM 1117, Gram-negative.

Cultures cells are suspended in sterile phosphate-buffered saline (PBS) or sterile PBS supplemented with 10% sterile horse blood serum. The bacterial suspensions are placed into sterile black well plates with clear bottoms. Concentrations of photosensitizer used in the study were as follows: 100 µM, 10 µM and 1 µM.

After an incubation time period of 30 minutes, the samples are exposed to white light, with a power density and irradiation time resulting in an energy fluency of about 100 J/$cm^2$. Control plates contained no photosensitizer and are not exposed to laser light. The control samples for dark toxicity are only exposed to photosensitizer without any illumination.

After irradiation, the samples are removed and suspended again in the culture media. The numbers of colony-forming units (CFU/ml) are enumerated after an adequate incubation time period.

Figure 13:
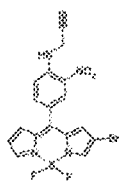
FIG. 13 shows the antibacterial effect of 2-Bromo-8-(4-N-propargylamino-3-nitrophenyl)-boron dipyrromethene against Staphylococcus aureus.
Figure 13:
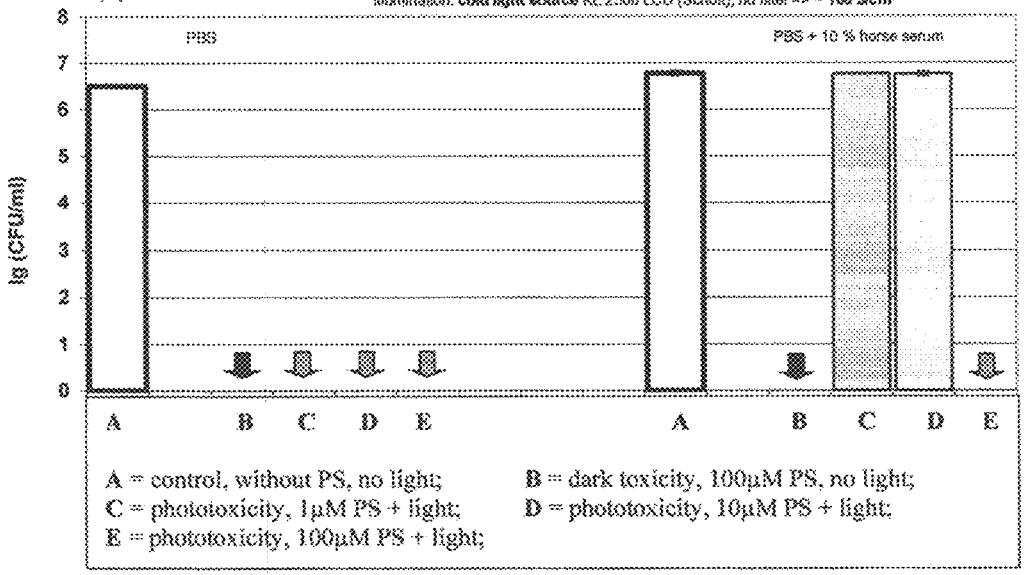
Figure 14:
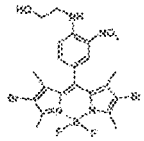
FIG. 14 shows the antibacterial effect of 1,3,5,7-Tetramethyl-2,6-dibromo-8-(4-N-hydroxy-ethylamino-3-nitrophenyl)-boron dipyrromethene against Staphylococcus aureus.
Figure 14:
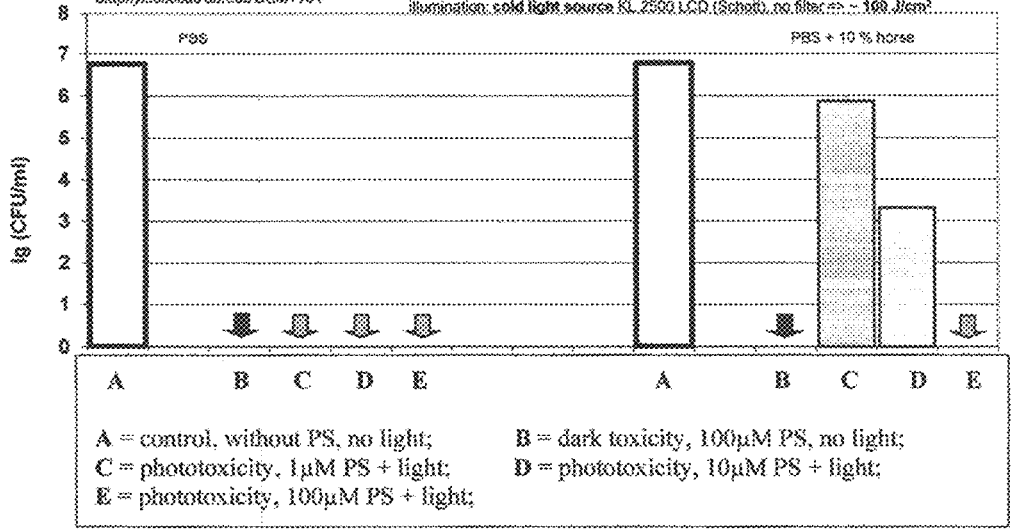
Figure 15:
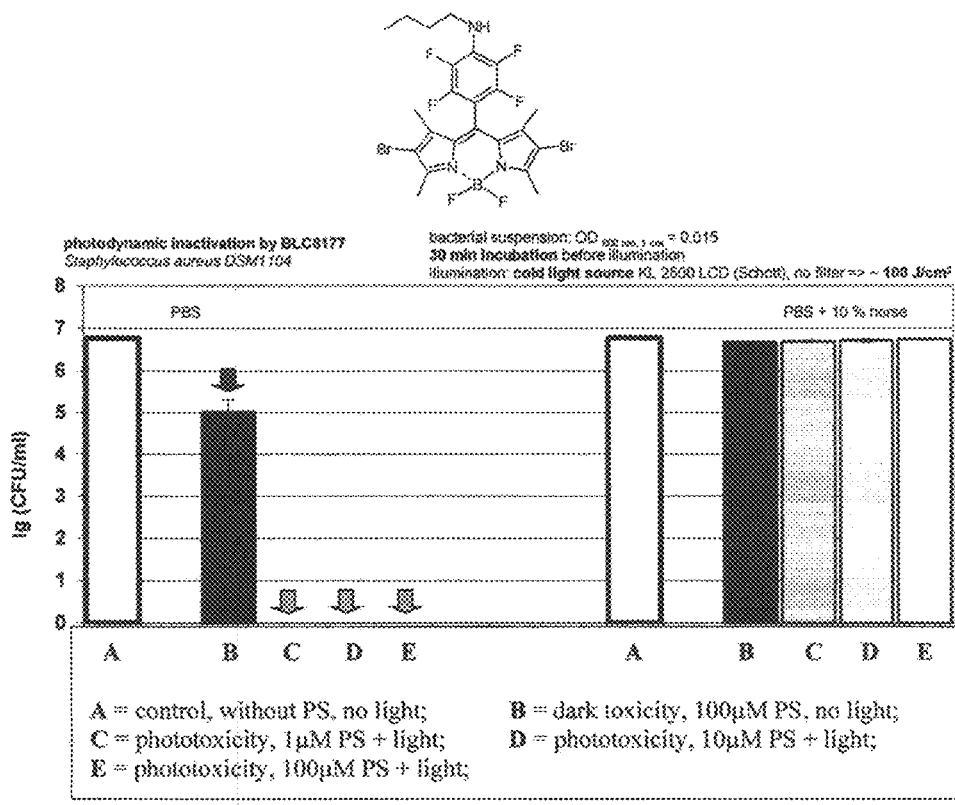
FIG. 15 shows the antibacterial effect of 1,3,5,7-Tetramethyl-2,6-dibromo-8-(4-N-butylamino-2,3,5,6-tetrafluorophenyl)-boron dipyrromethene against Staphylococcus aureus.
Figure 16:
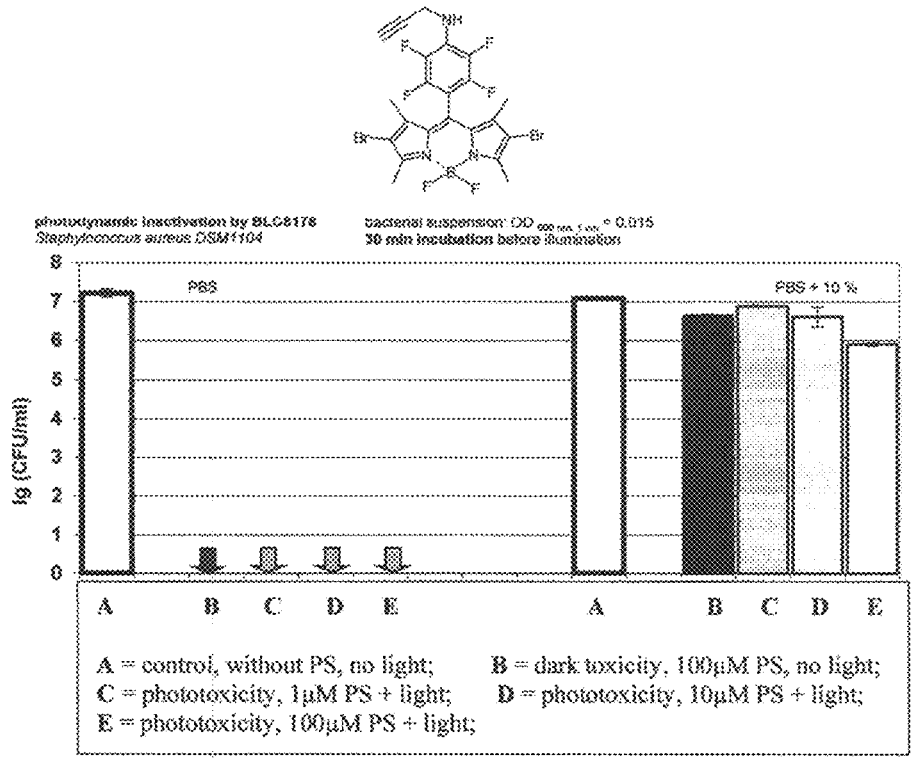
FIG. 16 shows the antibacterial effect of 1,3,5,7-Tetramethyl-2,6-dibromo-8-(4-N-propargylamino-2,3,5,6-tetrafluorophenyl)-boron dipyrromethene against Staphylococcus aureus.
Figure 17:
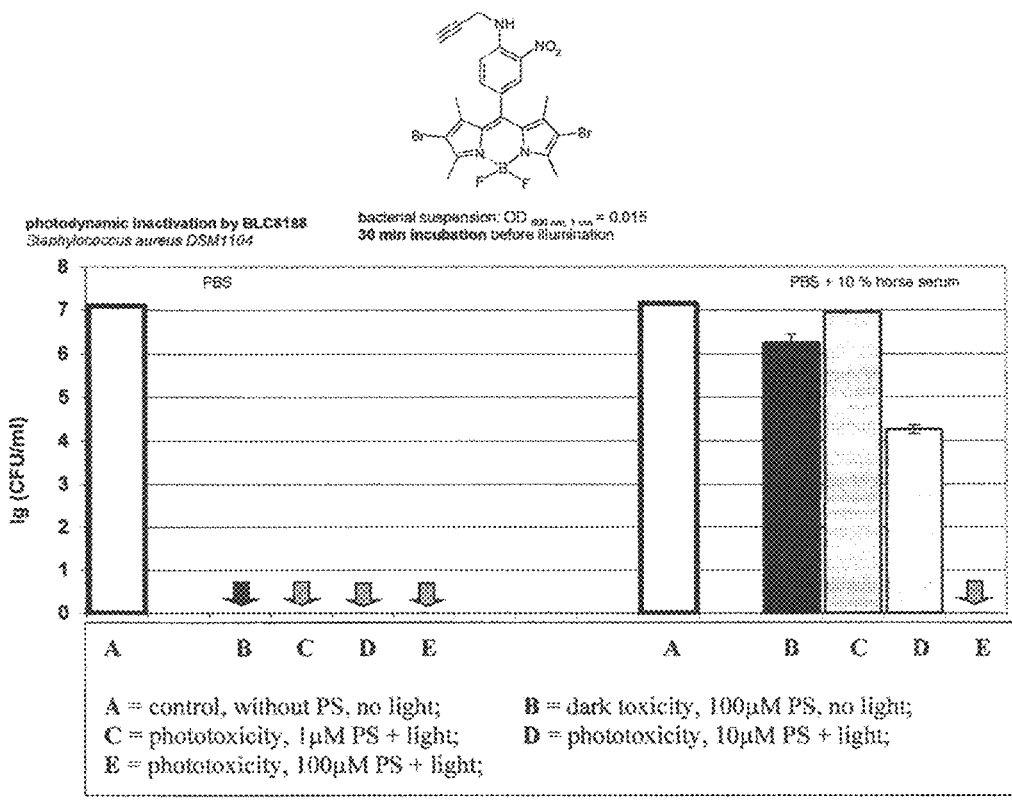
FIG. 17 shows the antibacterial effect of 1,3,5,7-Tetramethyl-2,6-dibromo-8(4-propargylamino-3-nitrophenyl)-boron dipyrromethene against Staphylococcus aureus.
Figure 18:
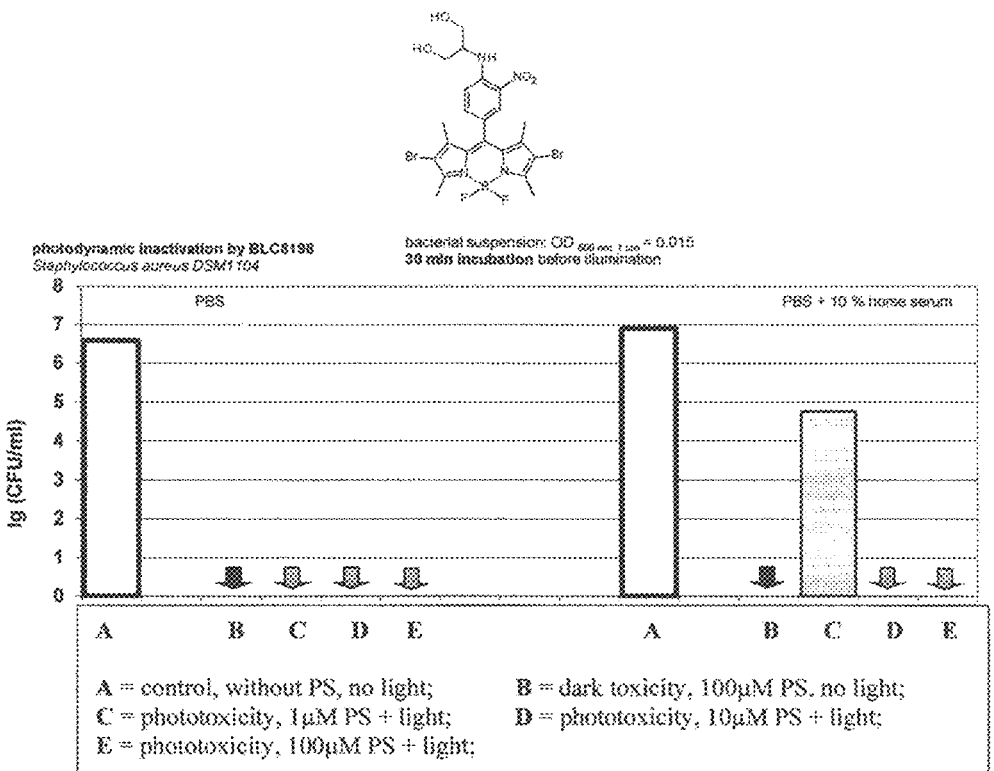
FIG. 18 shows the antibacterial effect of 1,3,5,7-Tetramethyl-2,6-dibromo-8-(4-(1-hydroxy-methyl)hydroxyethyl-amino-3-nitrophenyl)-boron dipyrromethene against Staphylococcus aureus.
Figure 19A:
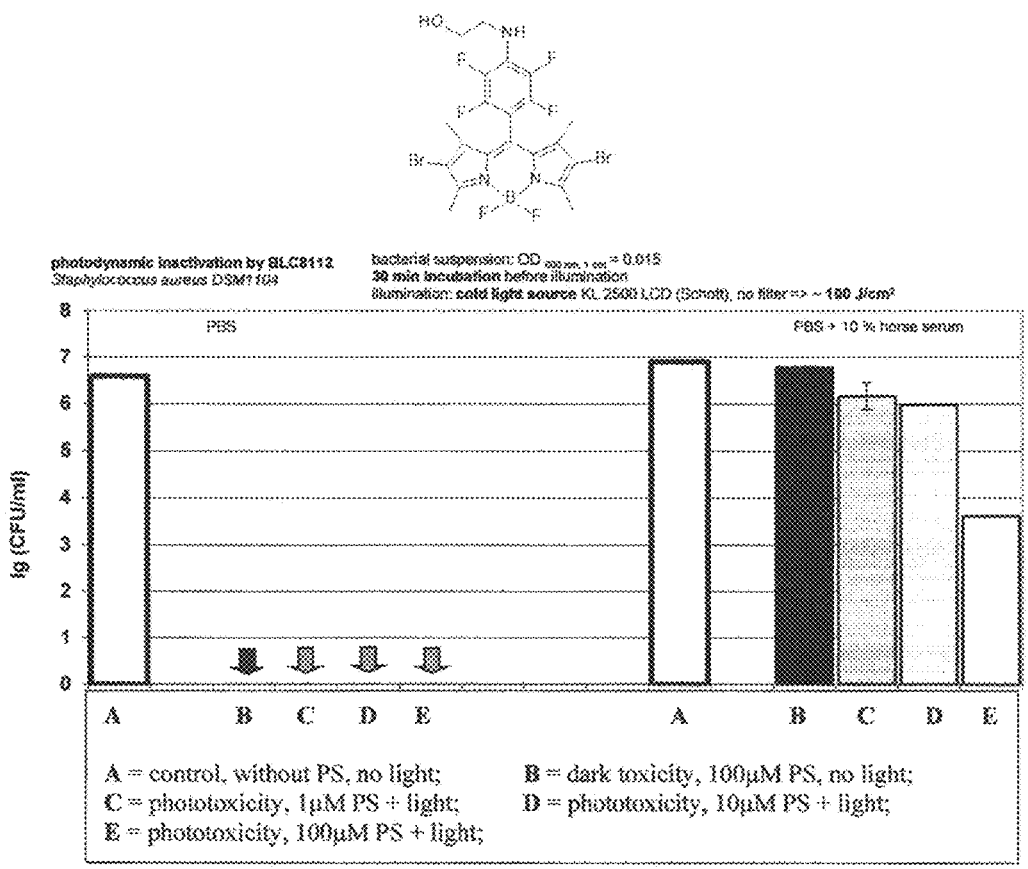
FIGS. 19A and B show the antibacterial effect of 1,3,5,7-Tetramethyl-2,6-dibromo-8-(4-(2-hydroxy-ethylamino)-2,3,5,6-tetrafluorophenyl)-boron dipyrromethene against Staphylococcus aureus and Pseudomonas aeruginosa, respectively.
Figure 19B:
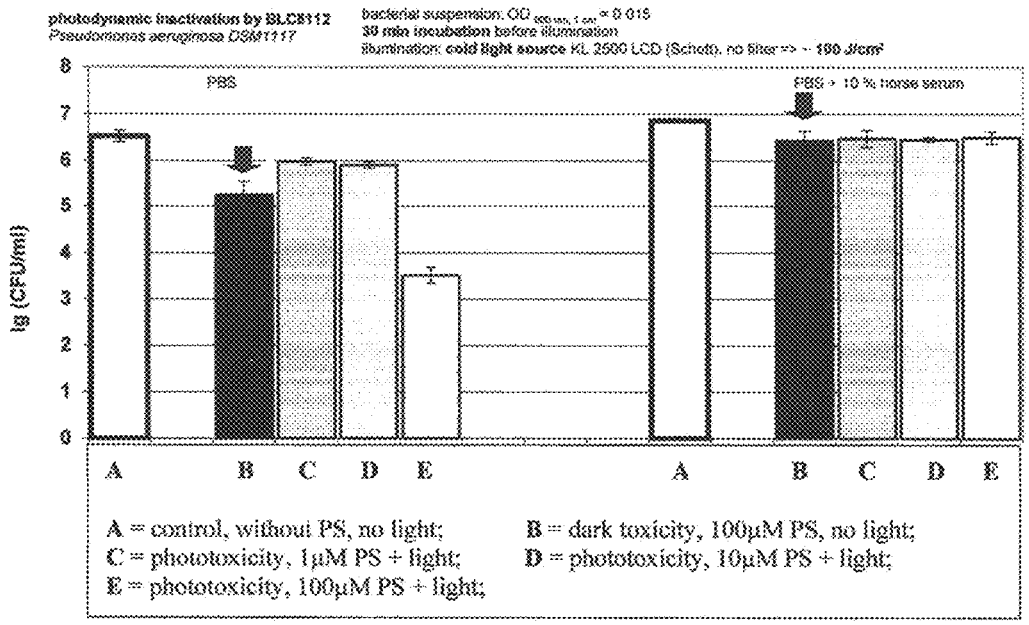
Figure 20A:
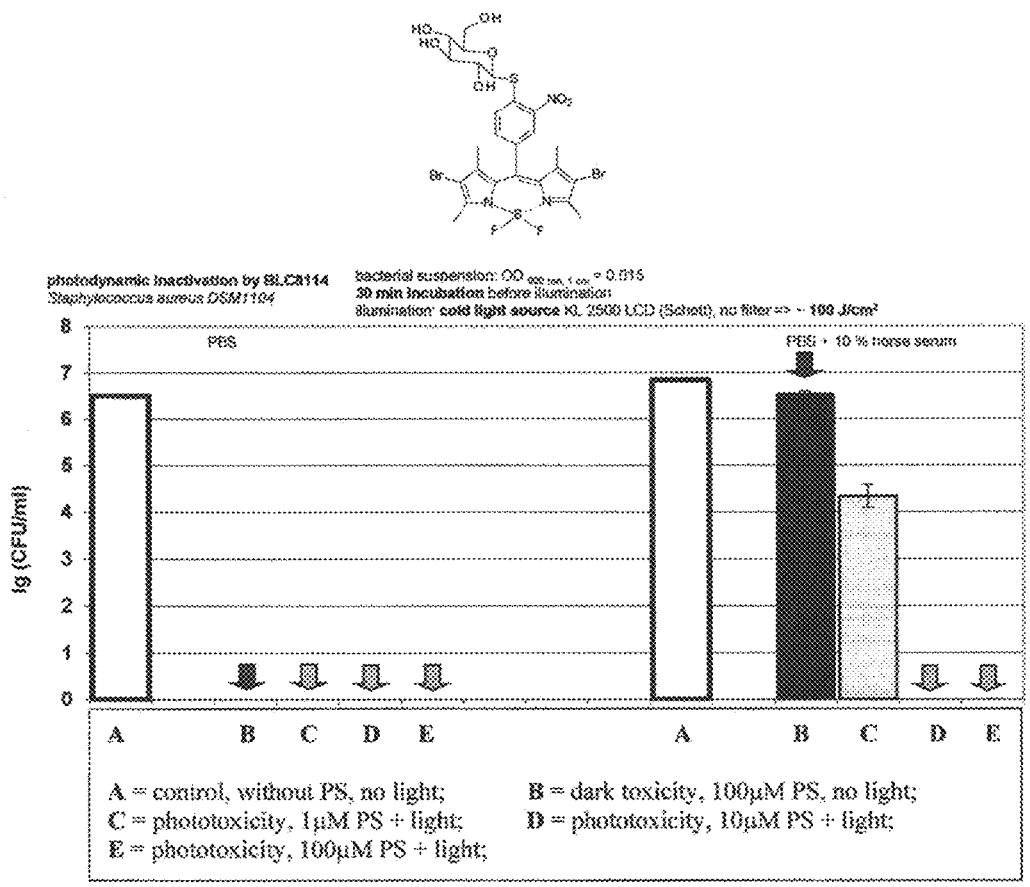
FIGS. 20A and B show the antibacterial effect of 1,3,5,7-Tetramethyl-2,6-dibromo-8-[4-(β-D-glucosylthio)-3-nitrophenyl]-boron dipyrromethene against Staphylococcus aureus and Pseudomonas aeruginosa, respectively.
Figure 20B:
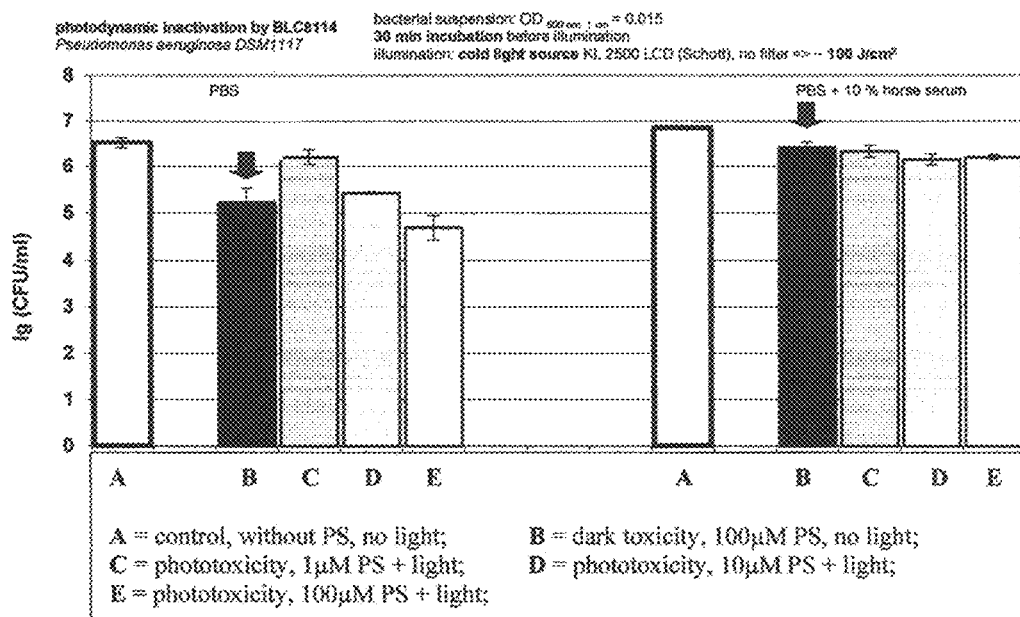
Figure 21A:
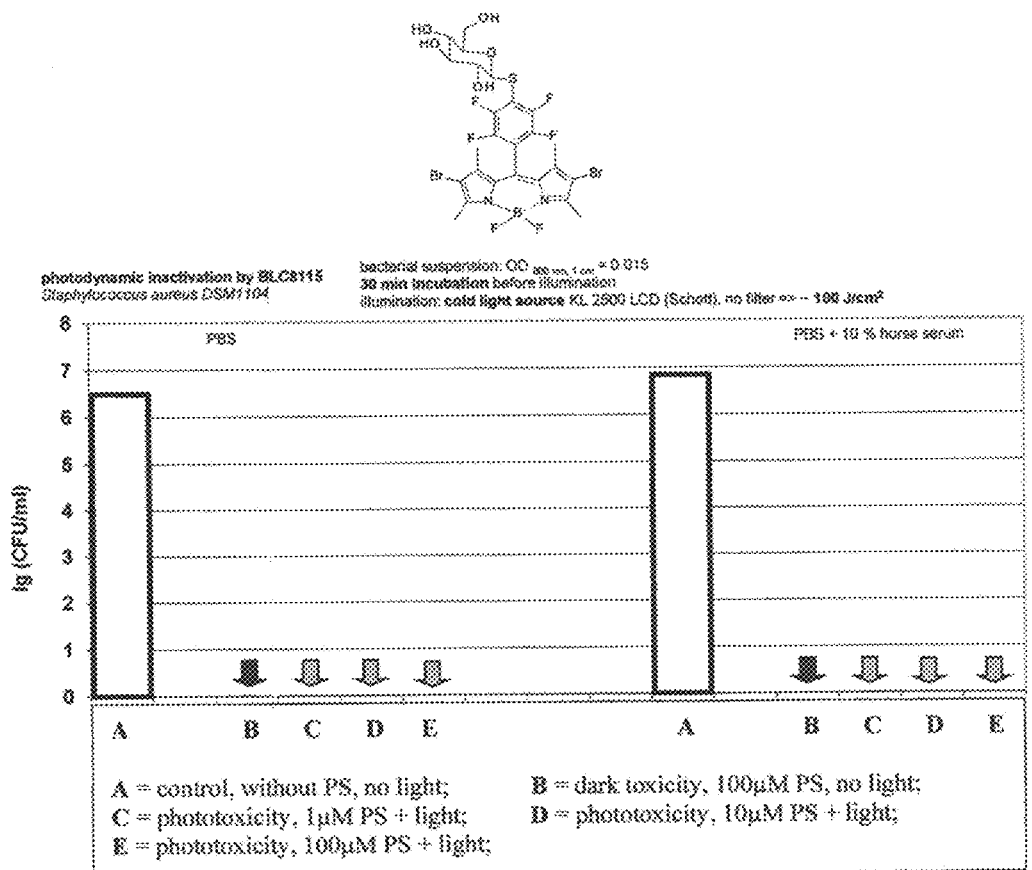
FIGS. 21A and B show the antibacterial effect of 1,3,5,7-Tetramethyl-2,6-dibromo-8-[4-(β-D-glucosylthio)-2,3,5,6-tetrafluorophenyl]-boron dipyrromethene against Staphylococcus aureus and Pseudomonas aeruginosa, respectively.
Figure 21B:
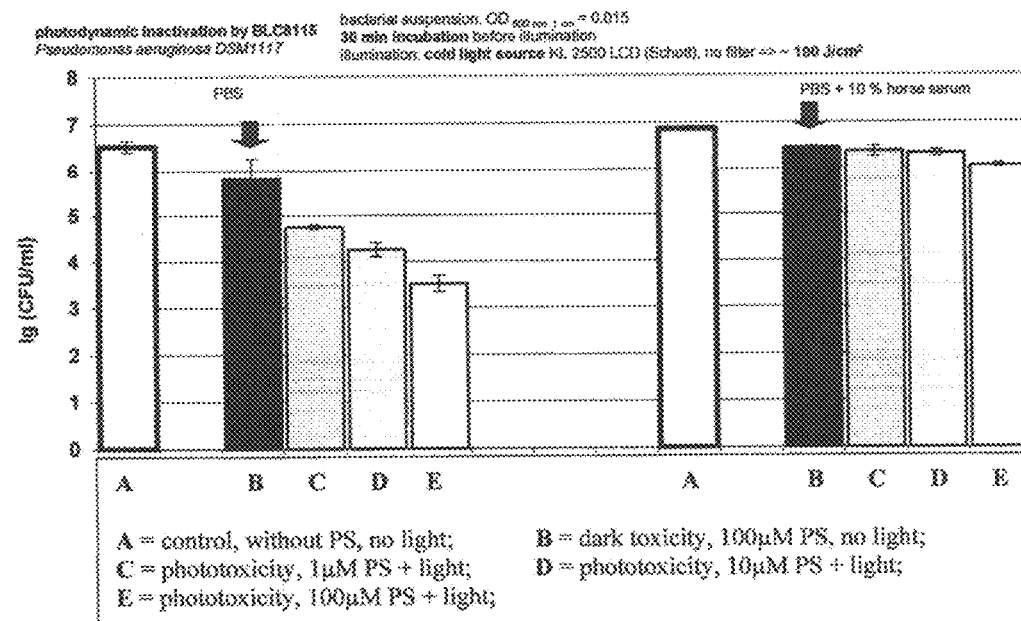
Figure 22A:
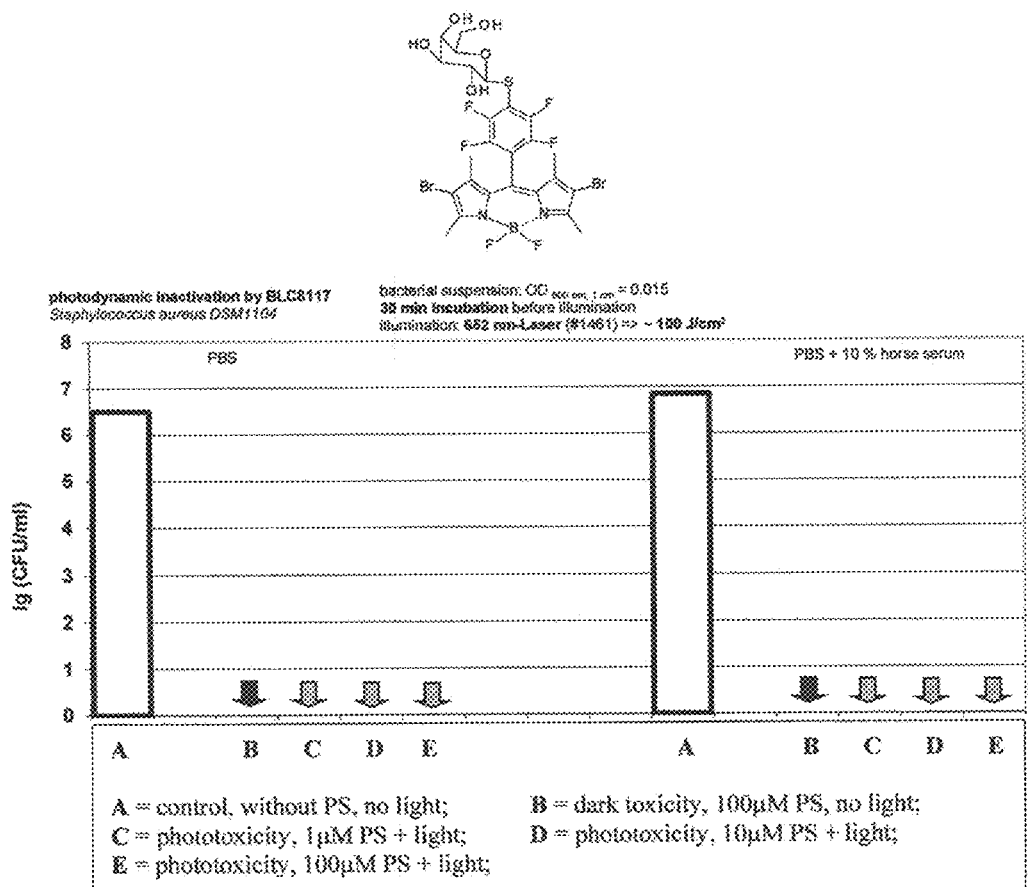
FIGS. 22A and B show the antibacterial effect of 1,3,5,7-Tetramethyl-2,6-dibromo-8-[4-(β-D-galactosylthio)-2,3,5,6-tetrafluorophenyl]-boron dipyrromethene against Staphylococcus aureus and Pseudomonas aeruginosa, respectively.
Figure 22B:
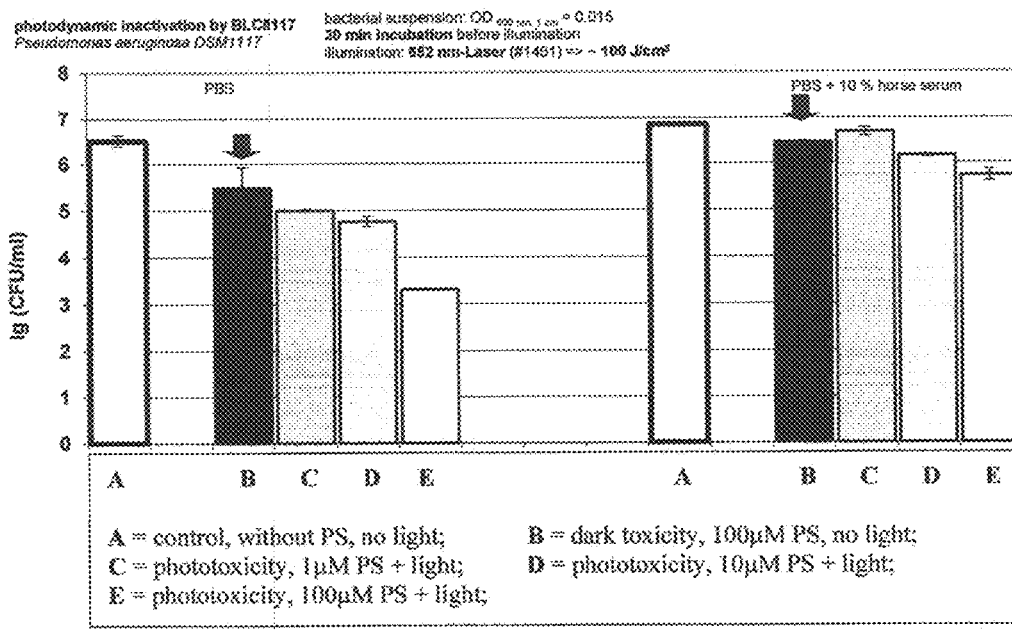
Figure 23A:
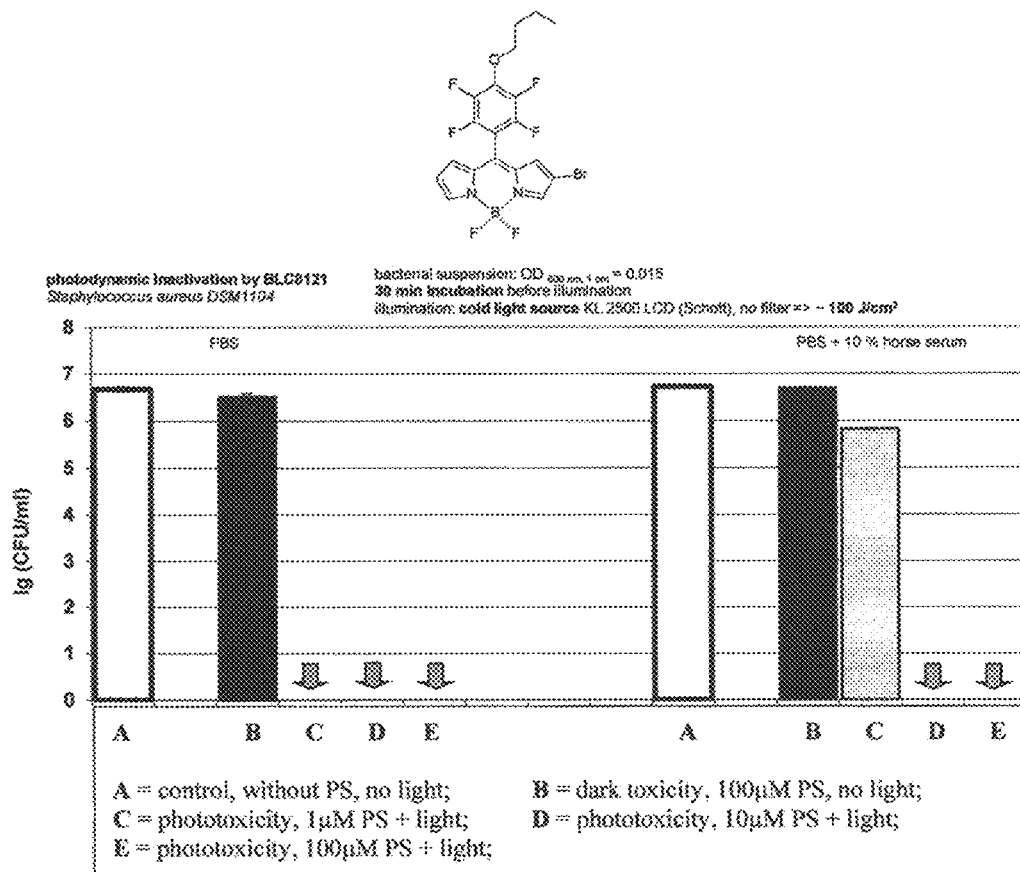
FIGS. 23A and B show the antibacterial effect of 2-Bromo-8-(4-butyloxy-2,3,5,6-tetrafluorophenyl)-boron dipyrromethene against Staphylococcus aureus and Pseudomonas aeruginosa, respectively.
Figure 23B:
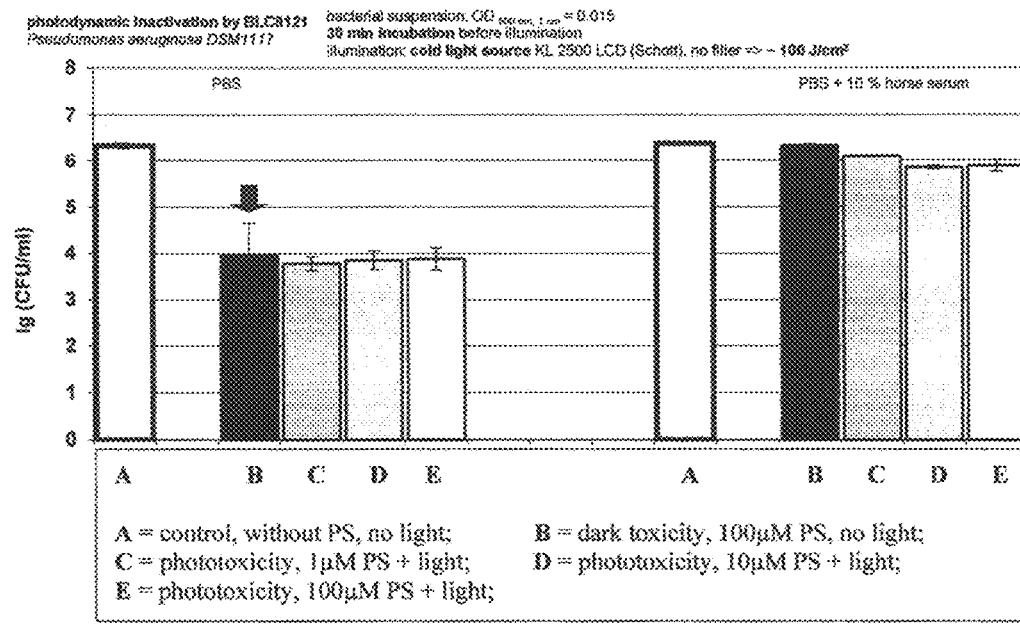

The FIGS. 13 to 24 of examples 4.1 to 4.11 illustrate the effect of boron dipyrromethenes according to the present invention against bacteria, the Gram-positive germ *Staphylococcus aureus* as well as the Gram-negative *Pseudomonas aeruginosa*. As can be seen from the examples, selected compounds (4.1, 4.2, 4.4 to 4.10) show a high antibacterial activity against *S. aureus* even in the absence of light (in the highest tested concentration of 100 µmol) exemplifying their principal suitability for a systemic treatment, especially since the compounds are on the other hand non-toxic to cells in the absence of light (cf. example 3). Also, some compounds may be specifically active against bacteria, whereat they exhibit only a low toxicity in cells (cf. example 4.5 in comparison with 3.12). For examples 4.1, 4.2, and 4.5 to 4.11 antibacterial activity is also observed in the presence of complex media (serum addition). Examples 4.7 to 4.11 illustrate the antibacterial effect of compounds according to the present invention against the Gram-negative germ *P. aeruginosa*. Also, example 4.1 and 4.11 illustrate the strong antibacterial activity of compounds according to the present invention which carry just one bromine atom.

Having described preferred embodiments of the invention with reference to the accompanying examples, it is to be understood that the invention is not limited to the precise embodiments, and that various changes and modifications may be effected therein by skilled in the art without departing from the scope of the invention as defined in the appended claims.

REFERENCES

[1] B. W. Henderson, T. J. Dougherty, Photodynamic therapy, basic principles and clinical applications. New York: Marcel Dekker, 1992.

[2] J. G. Moser, Photodynamic tumor therapy. 2nd and 3rd generation photosensitizers, Amsterdam: Harwood Academic Publishers, 1998.

[3] J. W. Kleinovink, P. B. van Driel, T. J. Snoeks, N. Prokopi, M. F. Fransen, L. J. Cruz, L. Mezzanotte, A. Chan, C. W. Löwik, F. Ossendorp, «Combination of Photodynamic Therapy and Specific Immunotherapy Efficiently Eradicates Established Tumors», Clin. Cancer Res., no 22, pp. 1459-1468, 2016.

[4] T. Maisch, «Strategies to optimize photosensitizers for photodynamic inactivation of bacteria», J. Photochem. Photobiol. B, 150, pp. 2-10, 2015.

[5] A. Treibs, F. H. Kreuzer, «Difluorboryl-Komplexe von Di- und Tripyrrylmethen», Justus Liebigs Ann. Chem., 718, pp. 208-223, 1968.

[6] C.-H. Lee, J. S. Lindsey, «One-Flask Synthesis of Meso-Substituted Dipyrromethanes and Their Application in the Synthesis of Trans-Substituted Porphyrin Building Blocks», Tetrahedron, vol. 50, p. 11427-11440, 1994.

[7] H. R. A. Golf, H.-U. Reissig, A. Wiehe, «Nucleophilic Substitution on (Pentafluorophenyl)dipyrromethane: A New Route to Building Blocks for Functionalized BODIPYs and Tetrapyrroles», Org. Lett., 17, pp. 982-985, 2015.

[8] G. Vives, C. Giansante, R. Bofinger, G. Raffy, A. Del Guerzo, B. Kauffmann, P. Batat, G. Jonusauskasc, N. D. McClenaghan, «Facile functionalization of a fully fluorescent perfluorophenyl BODIPY: photostable thiol and amine conjugates», Chem. Commun., 47, pp. 10425-10427, 2011.

[9] D. Prasannan, D. Raghav, S. Sujatha, H. Hareendrakrishna, K. Rathinasamy, C Arunkumar, «Synthesis, structure, photophysical, electrochemical properties and antibacterial activity of brominated BODIPYs», RSC Adv., 6, pp. 80808-80824, 2016.

[10] L. Bonardi, G. Uhrich, R. Ziessel, «Tailoring the Properties of Boron-Dipyrromethene Dyes with Acetylenic Functions at the 2, 6, 8 and 4-B Substitution Positions», Org. Lett., 11, pp. 2183-2186, 2008.

[11] L. Wang, J.-W. Wang, A-j. Cui, X.-X. Cai, Y. Wan, Q. Chen, M.-Y. Hea W. Zhang, «Regioselective 2,6-dihalogenation of BODIPYs in 1,1,1,3,3,3-hexafluoro-2-propanol and preparation of novel meso-alkyl polymeric BODIPY dyes», RSC Adv., 3, pp. 9219-9222, 2013.

[12] R. Klingenburg, C. B. W. Start, A. Wiehe, «Nucleophilic Thioglycosylation of Pentafluorophenyl-Substituted Porphyrinoids: Synthesis of Glycosylated Calix[n]phyrin and [28]Hexaphyrin Systems, Org. Lett., 21, pp. 5417-5420, 2019.

[13] C. S. Gutsche, M. Ortwerth, S. Grife, K. J. Flanagan, M. O. Senge, H.-U. Reissig, N. Kulak, A. Wiehe, «Nucleophilic Aromatic Substitution on Penta¬fluoro¬phenyl-Substituted Dipyranes and Tetrapyrroles as a Route to Multifunctionalized Chromophores for Potential Application in Photodynamic Therapy», Chem. Eur. J. 22, pp. 13953-13964, 2016.

[14] B. F. Hohlfeld, K. J. Flanagan, N. Kulak, M. O. Senge, M. Christmann, A. Wiehe, «Synthesis of Porphyrinoids, BODIPYs, and (Dipyrrinato)-ruthenium(II) Complexes from Prefunctionalized Dipyrromethanes», Eur. J. Org. Chem., pp. 4020-4033, 2019.

[15] C. S. Gutsche, B. F. Hohlfeld, K. J. Flanagan, M. O. Senge, N. Kulak, A. Wiehe, «Sequential Nucleophilic Substitution of the α-Pyrrole and p-ArylPositions of meso-Pentafluorophenyl-Substituted BODIPYs», Eur. J. Org. Chem., pp. 3187-3196, 2017.

What is claimed is:

1. A boron dipyrromethene compound based on the formulas 1, 2, 3 or 4:

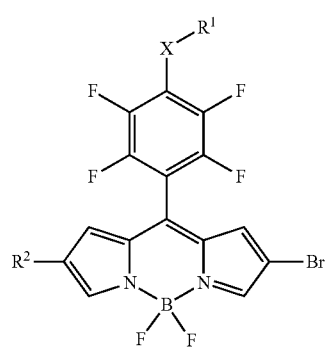

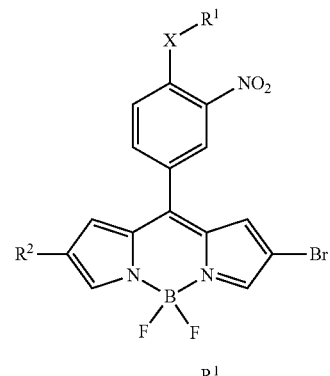

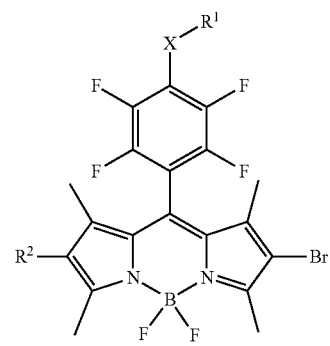

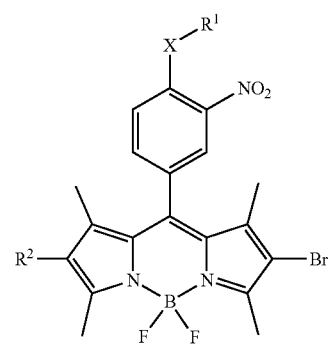

Wherein:
X is at least one of O, NH or S;
$R^1$ is at least one of a carbohydrate moiety, a short alkyl chain with 3 to 6 carbon atoms, propargyl, HO—$CH_2$—$CH_2$—, $CH(CH_2OH)_2$, $CH_2$—CH(OH)—$CH_2OH$, or CH(OH)—CH(OH)—$CH_3$; and
$R^2$ is at least one of hydrogen or a bromine substituent (atom).

2. A pharmaceutical composition comprising a compound according to claim 1 or a pharmaceutically acceptable derivative thereof as an active ingredient.

3. The pharmaceutical composition of claim 2, wherein the compound is conjugated to a targeting agent.

4. The pharmaceutical composition of claim 3, wherein the targeting agent is a peptide.

5. A pharmaceutical composition comprising a compound according to claim 1.

6. A method of treating a subject having a condition, selected from the group consisting of tumors, dermatological disorders, viral infections, bacterial infections, otorhinolaryngology disorders, ophthalmological disorders and urological disorders, comprising administering to the subject a therapeutically effective amount of the compound of claim 1.

7. The method of claim 6 wherein the condition comprises a tumor.

8. The method of claim 6 further comprising administering photodynamic therapy to the subject.

9. The method of claim 7 further comprising administering photodynamic therapy to the subject.

10. A method of treating a subject having arthritis comprising administering to the subject a therapeutically effective amount of the compound of claim 1, further comprising administering photodynamic therapy to the subject.

11. A method of diagnosing arthritis in a subject comprising administering to the subject an effective amount of the compound of claim 1 and performing fluorescence diagnosis on the subject.

* * * * *